United States Patent
Bazin-Lee et al.

(10) Patent No.: US 11,458,151 B2
(45) Date of Patent: Oct. 4, 2022

(54) TOLL-LIKE RECEPTOR LIGANDS

(71) Applicant: INIMMUNE CORPORATION, Missoula, MT (US)

(72) Inventors: Helene Bazin-Lee, Stevensville, MT (US); George Ettenger, Missoula, MT (US); Juhienah Khalaf, Hamilton, MT (US); Kendal T. Ryter, Hamilton, MT (US)

(73) Assignee: INIMMUNE CORPORATION, Missoula, MT (US)

( * ) Notice: Subject to any disclaimer, the term of this patent is extended or adjusted under 35 U.S.C. 154(b) by 39 days.

(21) Appl. No.: 16/968,835

(22) PCT Filed: Feb. 12, 2019

(86) PCT No.: PCT/US2019/017669
§ 371 (c)(1),
(2) Date: Aug. 10, 2020

(87) PCT Pub. No.: WO2019/157509
PCT Pub. Date: Aug. 15, 2019

(65) Prior Publication Data
US 2021/0023106 A1 Jan. 28, 2021

Related U.S. Application Data

(60) Provisional application No. 62/629,513, filed on Feb. 12, 2018.

(51) Int. Cl.
| *A61K 31/7008* | (2006.01) |
| *A61K 39/35* | (2006.01) |
| *A61K 39/39* | (2006.01) |
| *C07H 15/12* | (2006.01) |
| *C07H 15/26* | (2006.01) |
| *A61K 45/06* | (2006.01) |
| *A61K 39/00* | (2006.01) |

(52) U.S. Cl.
CPC .......... *A61K 31/7008* (2013.01); *A61K 39/35* (2013.01); *A61K 39/39* (2013.01); *C07H 15/12* (2013.01); *C07H 15/26* (2013.01); *A61K 45/06* (2013.01); *A61K 2039/57* (2013.01)

(58) Field of Classification Search
CPC .... C07H 15/12; C07H 15/26; A61K 31/7008; A61K 31/7028; A61K 39/39
See application file for complete search history.

(56) References Cited

U.S. PATENT DOCUMENTS

| | | |
|---|---|---|
| 5,530,113 A | 6/1996 | Christ et al. |
| 6,005,099 A | 12/1999 | Davies et al. |
| 6,113,918 A | 9/2000 | Johnson et al. |
| 6,303,347 B1 | 10/2001 | Johnson et al. |
| 6,355,257 B1 | 3/2002 | Johnson et al. |
| 6,525,028 B1 | 2/2003 | Johnson et al. |
| 6,699,846 B2 | 3/2004 | Elliott et al. |
| 6,764,840 B2 | 7/2004 | Johnson et al. |
| 6,800,613 B2 | 10/2004 | Persing et al. |
| 6,911,434 B2 | 6/2005 | Baldridge et al. |
| 7,063,967 B2 | 6/2006 | Johnson et al. |
| 7,129,219 B2 | 10/2006 | Johnson et al. |
| 7,232,900 B2 | 6/2007 | Johnson et al. |
| 7,288,640 B2 | 10/2007 | Johnson et al. |
| 7,501,399 B2 | 3/2009 | Johnson et al. |
| 7,541,020 B2 | 6/2009 | Johnson et al. |
| 7,820,627 B2 | 10/2010 | Jiang et al. |
| 7,829,542 B2 | 11/2010 | Baldridge et al. |
| 7,902,159 B2 | 3/2011 | Persing et al. |
| 7,960,522 B2 | 6/2011 | Johnson et al. |
| 7,960,523 B2 | 6/2011 | Johnson |
| 8,097,593 B1 | 1/2012 | Jiang et al. |
| 8,273,361 B2 | 9/2012 | Reed et al. |
| 8,318,697 B2 | 11/2012 | Persing et al. |
| 8,722,064 B2 | 5/2014 | Reed et al. |
| 2003/0105032 A1 | 6/2003 | Persing et al. |
| 2005/0192250 A1 | 9/2005 | Baldridge et al. |
| 2009/0227781 A1* | 9/2009 | Miyake ................ C07D 317/26 536/53 |
| 2011/0053871 A1* | 3/2011 | Egan .................. A61K 31/7008 435/375 |
| 2015/0017191 A1 | 1/2015 | Fox et al. |
| 2016/0022719 A1 | 1/2016 | Johnson et al. |
| 2017/0071967 A1 | 3/2017 | Dutta et al. |

(Continued)

FOREIGN PATENT DOCUMENTS

| WO | 2008128997 A1 | 10/2008 |
| WO | 2010118334 A1 | 10/2010 |
| WO | 2013132043 A1 | 9/2013 |

(Continued)

OTHER PUBLICATIONS

Intellectual Property Office of Singapore Search Report and Written Opinion for Application No. 11202007688Y dated Nov. 25, 2021 (9 pages).

(Continued)

*Primary Examiner* — Leigh C Maier
(74) *Attorney, Agent, or Firm* — Michael Best & Friedrich LLP

(57) ABSTRACT

Toll-like receptor (TLR) ligands having an allose-based core are stable in aqueous formulation and are useful in treating, preventing, or reducing susceptibility to diseases or conditions mediated by TLRs, such as cancer, infectious disease, allergy, autoimmune disease, sepsis, and ischemia reperfusion.

23 Claims, 15 Drawing Sheets

(56) References Cited

U.S. PATENT DOCUMENTS

2017/0072033 A1  3/2017  Dutta et al.

FOREIGN PATENT DOCUMENTS

| WO | 2016109880 A1 | 7/2016 |
| WO | 2017021792 A1 | 2/2017 |

OTHER PUBLICATIONS

Adamou et al., "Identification and Characterization of a Novel Family of Pneumococcal Proteins That Are Protective against Sepsis", Infect, and Immun., 2001, vol. 69, No. 2, pp. 949-958.

Bazin et al., "The 'Ethereal' nature of TLR4 agonism and antagonism in the AGP class of lipid A mimetics", Bioorg Med Chem Lett, 2008, vol. 18, No. 20, pp. 5350-5354.

Bethe et al., "The cell wall-associated serine protease PrtA: a highly conserved virulence factor of *Streptococcus pneumoniae*", FEMS Micro Biol. Lett., 2001, vol. 205, No. 1, pp. 99-104.

Bowen et al., "Selective TRIF-dependent signaling by a synthetic toll-like receptor 4 agonist", Sci. Signal, 2012, vol. 5, No. 211, 22 pages.

Brown et al., "Immunization with Components of Two Iron Uptake ABC Transporters Protects Mice Against Systemic *Streptococcus pneumoniae* Infection", Infect and Immun, 2001, vol. 69, No. 11, pp. 6702-6706.

Bryant et al., "The molecular basis of the host response to lipopolysaccharide", Nat Rev Microbiol, 2010, vol. 8, No. 1, pp. 8-14.

Cluff, "Monophosphoryl Lipid A (Mpl) as an Adjuvant for Anti-Cancer Vaccines: Clinical Results", Lipid A in Cancer Therapy, 2009, 14 pages.

Cullen et al., "A link between the assembly of flagella and lipooligosaccharide of the Gram-negative bacterium *Campylobacter jejuni*", PNAS, 2010, vol. 107, No. 11, pp. 5160-5165.

Dale, "Multivalent group A streptococcal vaccine designed to optimize the immunogenicity of six tandem M protein fragments", Vaccine, 1999, vol. 17, pp. 193-200.

Dale, "Recombinant, octavalent group A streptococcal M protein vaccine", Vaccine, vol. 14, No. 10, 1996, pp. 944-948.

DeMarco et al., "From agonist to antagonist: structure and dynamics of innate immune glycoprotein MD-2 upon recognition of variably acylated bacterial endotoxins", Mol Immunol, 2011, vol. 49, No. 1-2, pp. 124-133.

Feng et al., "Macrophages eat cancer cells using their own calreticulin as a guide: Roles of TLR and Btk", PNAS, 2015, vol. 112, No. 7, pp. 2145-2150.

Hoskins et al., "Genome of the Bacterium *Streptococcus pneumoniae* Strain R6", J. Bacterial, 2001, vol. 183, No. 19, pp. 5709-5717.

International Search Report and Written Opinion for Application No. PCT/US19/17669 dated Jun. 14, 2019 (15 pages).

Jomma et al., "Immunization with the iron uptake ABC transporter proteins PiaA and PiuA prevents respiratory infection with *Streptococcus pneumoniae*", Vaccine, vol. 24, 2006, pp. 5133-5139.

Khalaf et al., "Characterization of TRIF selectivity in the AGP class of lipid A mimetics: role of secondary lipid chains", Bioorg Med Chem Lett, 2015, vol. 25, No. 3, pp. 547-553.

LeMieux et al., "RrgA and RrgB are Components of a Multisubunit Pilus Encoded by the *Streptococcus pneumoniae* HrA Pathogenicity Islet", Infect. Imm., 2006, vol. 74, pp. 2453-2456.

Muroi et al., "Structural regions of MD-2 that determine the agonist-antagonist activity of lipid Iva", J Biol Chem, 2006, vol. 281, No. 9, pp. 5484-5491.

Park et al., "The structural basis of lipopolysaccharide recognition by the TLR4-MD-2 complex", Nature, vol. 458, 2009, pp. 1191-1196.

Plante et al., "Intranasal Immunization with Gonococcal Outer Membrane Prepartions Reduces the Duration of Vaginal Colonization of Mice", J Injectious Disease, 2000, vol. 182, pp. 848-855.

Price et al., "Immunogenicity of Gonococcal Transferrin Binding Proteins during Natural Infections", Infection and Immunity, 2004, vol. 72, No. 1, pp. 277-283.

Whalen et al., "PiuA and PiaA, iron uptake lipoproteins of *Streptococcus pneumoniae*, elicit serotype independent antibody responses following human pneumococcal septicaemia", FEMS Immunol. Med. Microbial., 2005, vol. 43, pp. 73-80.

Zhu et al., "DNA Immunization of mice with a plasmid encoding Neisseria gonorrhea PorB protein by intramuscular injection and epidermal particle bombardment", Vaccine, 2004, vol. 22, pp. 660-669.

Eurasian Patent Office Action for Application No. 202091931 dated Jul. 9, 2021 (14 pages including English translation and amended claims).

European Patent Office Extended Search Report for Application No. 19751710.5 dated Nov. 3, 2021 (7 pages).

* cited by examiner

TOLL-LIKE RECEPTOR LIGANDS

RELATED APPLICATIONS

This application is a U.S. national stage entry of International Patent Application No. PCT/US2019/017669, filed on Feb. 12, 2019, which claims priority to U.S. provisional application No. 62/629,513, filed Feb. 12, 2018, the entire contents of each of which are fully incorporated herein by reference.

STATEMENT OF GOVERNMENT INTEREST

This invention was made with government support under grant number 1R43AI136081-01A1 awarded by the National Institutes of Health. The government has certain rights in the invention.

TECHNICAL FIELD

The present invention relates to Toll-like receptor ligands useful in the treatment of diseases or conditions mediated by Toll-like receptors.

BACKGROUND

Gram-negative bacteria have long been known to illicit immunological responses through Toll-like receptors (TLRs). Distinct structural components that are unique to these pathogens have been linked to potent innate and adaptive immune responses. There is significant interest in developing agonists and antagonists of TLRs since the pharmacological manipulation of innate immune responses may lead to more effective vaccines and novel therapeutic approaches to autoimmune, allergic, atopic, malignant and infectious diseases.

The first microbial product discovered to be a Toll-like receptor agonist was the LPS derived lipid A, a highly conserved glucosamine based bacterial membrane component specific to grain negative bacteria, which activates Toll-like receptor 4 (TLR-4). Although lipid A is a potent immunomodulatory agent, its medicinal use is limited due to its extreme toxicity, including the induction of systemic inflammatory response syndrome. The toxic effects of lipid A can be ameliorated by selective chemical modification of lipid A to produce monophosphoryl lipid A compounds (MPL immunostimulant; GlaxoSmithKline). MPL immunostimulant and related compounds have adjuvant activity when used in vaccine formulations with protein and carbohydrate antigens for enhancing humoral and/or cell-mediated immunity to the antigens. The heterogeneity, low potency and poor stability of MPL and other naturally sourced or synthetic TLR4 ligands has hindered their use in many indications.

Thus, there is a need for improved TLR ligands with improved potency, stability, and/or purity.

SUMMARY

The present invention provides compounds or a pharmaceutically acceptable salt thereof and the methods, compositions and kits disclosed herein for treating or preventing a disease or condition mediated by Toll-like receptors. The TLR ligands of the invention have a novel allose-based scaffold with remarkable stability in aqueous formulation. In one aspect, the invention provides compounds of formula (I), or a pharmaceutically acceptable salt thereof,

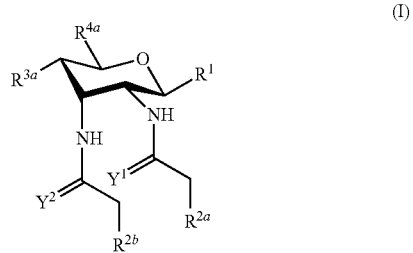

(I)

wherein:
$R^1$ is

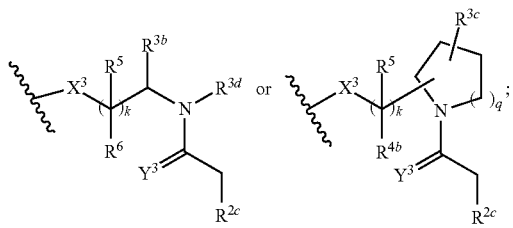

$R^{2a}$, $R^{2b}$, and $R^{2c}$ are each independently $C_{4-22}$alkyl, —$X^1$—$C_{3-21}$alkyl, —$CH_2$—$X^1$—$C_{2-20}$alkyl, or —$CH(R^{10})$($R^{11}$);

$R^{10}$, at each occurrence, is independently $C_{1-21}$alkyl, —$X^1$—$C_{2-20}$alkyl, or —$CH_2$—$X^1$—$C_{1-19}$alkyl;

$R^{11}$, at each occurrence, is independently $C_{3-17}$alkyl, —$X^2$—$C_{2-16}$alkyl, —$CH_2$—$X^2$—$C_{1-15}$alkyl, —$X^2$—$C(=Y^4)C_{1-15}$alkyl, —$CH_2$—$C(=Y^4)C_{1-15}$alkyl, —$X^2$—$C(=Y^4)C_{1-15}$alkylene-$Z^1$—$C_{1-15}$alkyl, —$CH_2$—$C(=Y^4)C_{1-15}$alkylene-$Z^1$—$C_{1-15}$alkyl, —$C_{3-17}$alkylene-$Z^1$—$C_{1-15}$alkyl, —$X^2$—$C_{2-16}$alkylene-$Z^1$—$C_{1-15}$alkyl, —$CH_2$—$X^2$—$C_{1-15}$alkylene-$Z^1$—$C_{1-15}$alkyl, —$X^2$—$C(=Y^4)C_{1-15}$alkyl-$Z^2$, or —$X^2$—$C_{2-16}$alkylene-$Z^2$;

$R^{3a}$, $R^{3b}$, and $R^{3c}$ are each independently $CO_2H$, —$OSO_3H$, —$OP(O)(OH)_2$, —$C_{1-6}$alkylene-$CO_2H$, —$C_{1-6}$alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, —$C_{1-6}$haloalkylene-$P(O)(OH)_2$, H, or an ester of the $CO_2H$, —$OSO_3H$, —$OP(O)(OH)_2$, —$C_{1-6}$alkylene-$CO_2H$, —$C_{1-6}$alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, or —$C_{1-6}$haloalkylene-$P(O)(OH)_2$;

$R^{3d}$ is $CO_2H$, —$SO_3H$, —$P(O)(OH)_2$, —$C_{1-6}$alkylene-$CO_2H$, —$C_{1-6}$alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, —$C_{1-6}$haloalkylene-$P(O)(OH)_2$, H, $C_{1-6}$alkyl, $C_{1-6}$haloalkyl, $C_{3-8}$cycloalkyl, or an ester of the $CO_2H$, —$OSO_3H$, —$OP(O)(OH)_2$, —$C_{1-6}$alkylene-$CO_2H$, —$C_{1-6}$alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, or —$C_{1-6}$haloalkylene-$P(O)(OH)_2$;

$R^{4a}$ is $CO_2H$, $CH_2OSO_3H$, $CH_2CO_2H$, $CH_2P(O)(OH)_2$, $CH_2H$, H, or an ester of the $CO_2H$, $CH_2SO_3H$, $CH_2CO_2H$, or $CH_2P(O)(OH)_2$;

$R^{4b}$, at each occurrence, is independently $CO_2H$, $CH_2SO_3H$, $CH_2CO_2H$, $CH_2P(O)(OH)_2$, $CH_2OH$, H, or an ester of the $CO_2H$, $CH_2SO_3H$, $CH_2CO_2H$, or $CH_2P(O)(OH)_2$;

$R^5$ and $R^6$, at each occurrence, are independently H, $C_{1-6}$alkyl, $C_{1-6}$haloalkyl, —O—$C_{1-6}$alkyl, or —$C_{1-6}$alkylene-OH;

$X^1$ and $X^2$, at each occurrence, are independently O, S, or NH;

$X^3$ is O, S, NH, or $CH_2$;

$Y^1$, $Y^2$, and $Y^3$ are independently O, S, NH, or $H_2$;

$Y^4$, at each occurrence, is independently O, S, or NH;

$Z^1$, at each occurrence, is independently phenylene or 5- to 6-membered heteroarylene, the phenylene and heteroarylene being optionally substituted with 1-4 substituents independently selected from $C_{1-4}$alkyl, $C_{1-4}$haloalkyl, $-OC_{1-4}$alkyl, $-OC_{1-4}$haloalkyl, cyano, and halogen;

$Z^2$, at each occurrence, is independently phenyl or a 5- to 6-membered heteroaryl, wherein $Z^2$ is optionally substituted with 1-5 substituents independently selected from $C_{1-4}$alkyl, $C_{1-4}$haloalkyl, $-OC_{1-4}$alkyl, $-OC_{1-4}$haloalkyl, cyano, and halogen; and k and q are each independently an integer from 0-4.

Another aspect of the present invention provides pharmaceutical compositions comprising a pharmaceutically acceptable carrier and the compound of formula (I), or a pharmaceutically acceptable salt thereof.

Another aspect of the invention provides a method of treating, preventing, or reducing the susceptibility to a disease or condition mediated by a Toll-like receptor comprising administering to a subject, in need thereof, a therapeutically effective amount of a compound of formula (I), or a pharmaceutically acceptable salt or a pharmaceutical composition thereof.

Another aspect of the invention provides a method of eliciting or enhancing, or modifying an immune response in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility to cancer in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility to an infectious disease in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility to an allergy in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility to an autoimmune condition in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility in a subject to bacterial, viral, prion infection, autoimmunity, cancer or allergy comprising administering to a subject in need thereof a therapeutically effective amount of the compound of formula (I), or a pharmaceutically acceptable salt or a pharmaceutical composition thereof.

Another aspect of the invention provides a method of treating or preventing or reducing the susceptibility to autoimmunity, allergy, ischemia reperfusion or sepsis in a subject comprising administering to a subject in need thereof a therapeutically effective amount of the compound of formula (I), or a pharmaceutically acceptable salt or a pharmaceutical composition thereof.

In another aspect, the invention provides compounds of formula (I), or a pharmaceutically acceptable salt thereof, for use in treating a disease or condition mediated by a Toll-like receptor.

In another aspect, the invention provides the use of a compound of formula (I), or a pharmaceutically acceptable salt thereof, for the manufacture of a medicament for the treatment a disease or condition mediated by a Toll-like receptor.

The invention also provides kits comprising compounds of formula (I).

DETAILED DESCRIPTION

1. Definitions

Figure 1A:
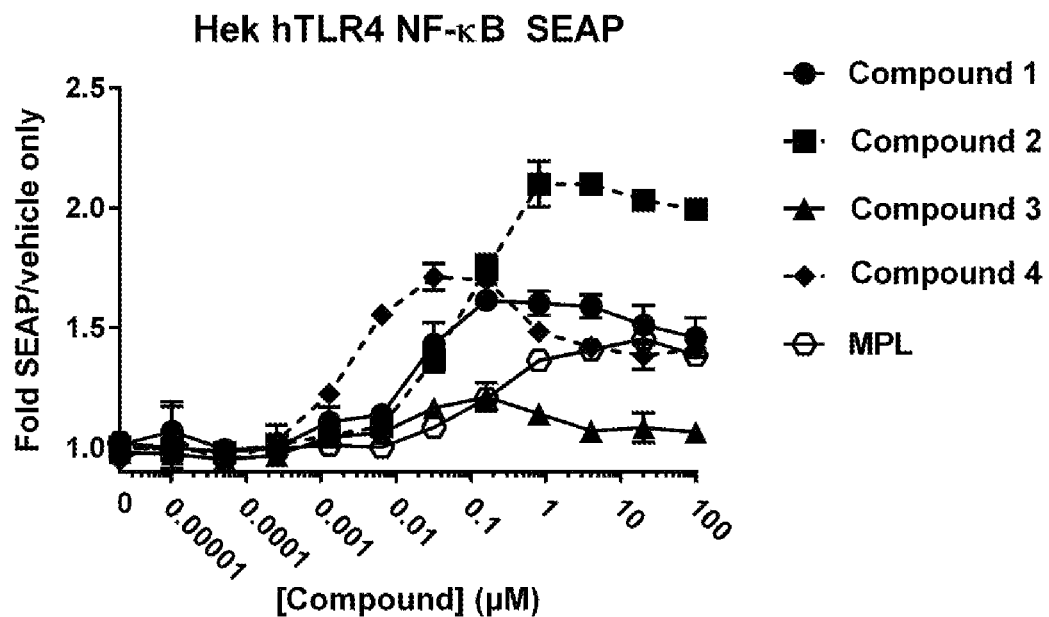
FIGS. 1A, 1B, and 1C show hTLR4 activation by representative compounds. Hek hTLR4-expressing cells also containing an NF-κB driven SEAP reporter were stimulated with the indicated concentration of the indicated compound for 18 hours followed by assessment of the cellular supernatant for SEAP. Results depict the average OD values over the average OD value for vehicle treated cells (±SD) of technical duplicates.

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" as used herein, means a straight or branched chain saturated hydrocarbon. Representative examples of alkyl include, but are not limited to, methyl, ethyl, npropyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —$CH_2$—, —$CH_2CH_2$—, —$CH_2CH_2CH_2$—, —$CH_2CH(CH_3)CH_2$—, and $CH_2CH(CH_3)CH(CH_3)CH_2$—.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

The term "heteroaryl," as used herein, means an aromatic heterocycle, i.e., an aromatic ring that contains at least one heteroatom selected from O, N, or S. A heteroaryl may contain from 5 to 12 ring atoms. A heteroaryl may be a 5- to 6-membered monocyclic heteroaryl or an 8- to 12-membered bicyclic heteroaryl. A 5-membered monocyclic heteroaryl ring contains two double bonds, and one, two, three, or four heteroatoms as ring atoms. Representative examples of 5-membered monocyclic heteroaryls include, but are not limited to, furanyl, imidazolyl, isoxazolyl, isothiazolyl, oxadiazolyl, oxazolyl, pyrazolyl, pyrrolyl, tetrazolyl, thiadiazolyl, thiazolyl, thienyl, and triazolyl. A 6-membered heteroaryl ring contains three double bonds, and one, two, three or four heteroatoms as ring atoms. Representative examples of 6-membered monocyclic heteroaryls include, but are not limited to, pyridinyl, pyridazinyl, pyrimidinyl, pyrazinyl, and triazinyl. The bicyclic heteroaryl is an 8- to 12-membered ring system having a monocyclic heteroaryl fused to an aromatic, saturated, or partially saturated carbocyclic ring, or fused to a second monocyclic heteroaryl ring. Representative examples of bicyclic heteroaryl include, but are not limited to, benzofuranyl, benzoxadiazolyl, 1,3-benzothiazolyl, benzimidazolyl, benzothienyl, indolyl, indazolyl, isoquinolinyl, naphthyridinyl, oxazolopyridine, quinolinyl, thienopyridinyl, 5,6,7,8-tetrahydroquinolinyl, and 6, 7-dihydro-5H-cyclopenta[b Jpyridinyl. The heteroaryl groups are connected to the parent molecular moiety through any substitutable carbon atom or any substitutable nitrogen atom contained within the groups.

The term "cycloalkyl" as used herein, means a monocyclic all-carbon ring containing zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such abridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and spiro heterocycle groups are connected to the parent molecular moiety through any substitutable carbon atom or any substitutable nitrogen atom contained within the group.

The term "oxo" as used herein refers to an oxygen atom bonded to the parent molecular moiety. An oxo may be attached to a carbon atom or a sulfur atom by a double bond. Alternatively, an oxo may be attached to a nitrogen atom by a single bond, i.e., an N-oxide.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

Compounds of the invention have the stereochemical configurations around the core sugar as specifically shown in formula (I). Apart from the core sugar stereochemistry, stereocenters located in any substituent appended to the core sugar include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterioinc forms of the compounds or salts of formula I where appropriate.

2. Compounds

A first aspect of the invention provides compounds of formula (I), or a pharmaceutically acceptable salt thereof, wherein $R^1$, $R^{2a}$, $R^{2b}$, $R^{3a}$, $R^{4a}$, $Y^1$, and $Y^2$ are as defined herein.

$R^{2a}$, $R^{2b}$, and $R^{2c}$ may be independently $C_{4-22}$alkyl, —$X^1$—$C_{3-21}$alkyl, —$CH_2$—$X^1$—$C_{2-20}$alkyl, or —$CH(R^{10})(R^{11})$. $R^{10}$, at each occurrence, is independently $C_{1-21}$alkyl, —$X^1$—$C_{2-20}$alkyl, or —$CH_2$—$X^1$—$C_{1-19}$alkyl. $R^{11}$, at each occurrence, is independently $C_{3-17}$alkyl, —$X^2$—$C_{2-16}$alkyl, —$CH_2$—$X^2$—$C_{1-15}$alkyl, —$X^2$—$C(=Y^4)C_{1-15}$alkyl, —$CH_2$—$C(=Y^4)C_{1-15}$alkyl, —$X^2$—$C(=Y^4)C_{1-15}$alkylene-$Z^1$—$C_{1-15}$alkyl, —$CH_2$—$C(=Y^4)C_{1-15}$alkylene-$Z^1$—$C_{1-15}$alkyl, —$C_{3-17}$alkylene-$Z^1$—$C_{1-15}$alkyl, —$X^2$—$C_{2-16}$alkylene-$Z^1$—$C_{1-15}$alkyl, —$CH_2$—$X^2$—$C_{1-15}$alkylene-$Z^1$—$C_{1-15}$alkyl, —$X^2$—$C(=Y^4)C_{1-15}$alkylene-$Z^2$, or —$X^2$—$C_{2-16}$alkylene-$Z^2$. $X^1$ and $X^2$, at each occurrence, are independently O, S, or NH. $Y^4$, at each occurrence, is O, S, or NH. $Z^1$, at each occurrence, is independently phenylene or 5- to 6-membered heteroarylene, the phenylene and heteroarylene being optionally substituted with 1-4 substituents independently selected from $C_{1-4}$alkyl, $C_{1-4}$haloalkyl, —$OC_{1-4}$alkyl, —$OC_{1-4}$haloalkyl, cyano, and halogen. $Z^2$, at each occurrence, is independently phenyl or a 5- to 6-membered heteroaryl, wherein $Z^2$ is optionally substituted with 1-5 substituents independently selected from $C_{1-4}$alkyl, $C_{1-4}$haloalkyl, —$OC_{1-4}$alkyl, —$OC_{1-4}$haloalkyl, cyano, and halogen. Independent occurrences of $X^1$, $X^2$, $Y^4$, $Z^1$, $Z^2$, $R^{10}$, and $R^{11}$ at $R^{2a}$, $R^{2b}$, and $R^{2c}$ may be the same or different according to the definitions provided herein. Likewise, the alkyl and alkylene groups in $R^{2a}$, $R^{2b}$, $R^{2c}$, $R^{10}$, and $R^{11}$ may have the same or different number of carbon atoms at each occurrence. The description of embodiments pertaining to variables $X^1$, $X^2$, $Y^4$, $Z^1$, $Z^2$, $R^{10}$, and $R^{11}$ thus refer to embodiments having one or more occurrence of the recited variable definitions. Each separate occurrence, however, may have the same or different definition.

In some embodiments, $R^{2a}$, $R^{2b}$, and $R^{2c}$ are each independently —$CH(R^{10})(R^{11})$.

In some embodiments, $R^{10}$ is $C_{1-21}$alkyl, such as $C_{1-19}$alkyl or $C_{3-21}$alkyl (e.g., $C_{11}$alkyl, such as straight chain $C_{11}$alkyl).

In some embodiments, $R^{10}$, at each occurrence, is independently $C_{1-21}$alkyl, such as $C_{1-19}$alkyl or $C_{3-21}$alkyl (e.g., $C_{8-14}$alkyl, $C_{10-12}$alkyl, or $C_{11}$alkyl, such as straight chain $C_{11}$alkyl). The independent $C_{1-21}$alkyl may be the same or different (e.g., different chain lengths and/or branched versus straight chain).

In some embodiments, $R^{11}$, at each occurrence, is independently —$X^2$—$C(=Y^4)C_{1-15}$alkyl (e.g., —O—$C(=O)C_{1-15}$alkyl, such as —O—$C(=O)C_9$alkyl). The independent —$X^2$—$C(=Y^4)C_{1-15}$alkyl may be the same or different (e.g., different chain lengths and/or branched versus straight chain and/or O, S, or NH at $X^2$ and $Y^4$). For example, one instance of $R^{11}$ may be —$X^2$—$C(=Y^4)C_9$ alkyl and the other instances —X²—C(=Y⁴)C₁₀ alkyl. Or all three instances of R¹¹ may be different.

In some embodiments, R¹¹, at each occurrence, is independently —X²—C₂₋₁₆alkyl (e.g., —O—C₂₋₁₆alkyl such as —O—C₁₀alkyl). The independent —X²—C₂₋₁₆alkyl may be the same or different (e.g., different chain lengths and/or branched versus straight chain and/or O, S, or NH at X²). For example, one instance of R¹¹ may be —X²—C₁₀alkyl and the other instances —X²—C₁₁alkyl. Or all three instances of R¹¹ may be different.

In some embodiments, R¹¹, at each occurrence, is independently —X²—C(=Y⁴)C₁₋₁₅alkylene-Z² (e.g., —O—C(=O)C₁₋₁₅alkylene-Z² such as —O—C(=O)C₇alkylene-Z²). The independent —X²—C(=Y⁴)C₁₋₁₅alkylene-Z² may be the same or different (e.g., different chain lengths and/or branched versus straight chain and/or O, S, or NH at X² and Y⁴). For example, one instance of R¹¹ may be —X²—C(=Y⁴)C₇alkylene-Z² and the other instances —X²—C(=Y⁴)C₈alkylene-Z². Or all three instances of R¹¹ may be different.

In some embodiments, R¹¹, at one occurrence (e.g., at R²ᵇ) is —X²—C(=Y⁴)C₁₋₁₅alkylene-Z² (e.g., —O—C(=O)C₁₋₁₅alkylene-Z² such as —O—C(=O)C₇alkylene-Z²) and the other two occurrences of R¹¹ (e.g., at R²ᵃ and R²ᶜ) are independently —X²—C(=Y⁴)C₁₋₁₅alkyl (e.g., —O—C(=O)C₁₋₁₅alkyl, such as —O—C(=O)C₉alkyl) or other options for R.

In some embodiments, R¹¹, at each occurrence, is independently —X²—C₂₋₁₆alkylene-Z² (e.g., —O—C₂₋₁₆alkylene-Z² such as —O—C₈₋₉alkylene-Z²). The independent —X²—C₂₋₁₆alkylene-Z² may be the same or different (e.g., different chain lengths and/or branched versus straight chain and/or O, S, or NH at X²). For example, one instance of R¹¹ may be —X²—C₈alkylene-Z² and the other instances —X²—C₉alkylene-Z². Or all three instances of R¹¹ may be different.

In some embodiments, R¹¹, at one occurrence (e.g., at R²ᵇ) is —X²—C₂₋₆alkylene-Z² (e.g., —O—C₂₋₁₆alkylene-Z² such as —O—C₈₋₉alkylene-Z²) and the other two occurrences of R¹¹ (e.g., at R²ᵃ and R²ᶜ) are independently —X²—C₂₋₁₆alkyl (e.g., —O—C₂₋₁₆alkyl such as —O—C₁₀alkyl) or other options for R¹¹.

For example, in embodiments having at least one occurrence of —CH(R¹⁰)(R¹¹), at least one occurrence of R¹⁰ and R¹¹ may be defined as follows. R¹⁰ may be C₁₋₁₉alkyl and R¹¹ is —X²—C(=Y⁴)C₁₋₁₅alkyl. R¹⁰ may be C₁₋₁₉alkyl and R¹¹ is —CH₂—C(=Y⁴)C₁₋₁₅alkyl. R¹⁰ may be C₁₋₁₉alkyl and R¹¹ is C₃₋₁₇alkyl. R¹⁰ may be C₁₋₁₉alkyl and R¹¹ is —X²—C₂₋₁₆alkyl. R¹⁰ may be C₁₋₁₉alkyl and R¹¹ is X²—C(=Y⁴)C₁₋₁₅alkylene-Z¹—C₁₋₁₅alkyl. R¹ may be C₁₋₁₉alkyl and R¹¹ is —CH₂—C(=Y⁴)C₁₋₁₅alkylene-Z¹—C₁₋₁₅alkyl. R¹⁰ may be C₁₋₁₉alkyl and R¹¹ is X²—C₂₋₁₆alkylene-Z¹—C₁₋₁₅alkyl. R¹⁰ may be C₁₋₁₉alkyl and R¹¹ is —X²—C(=Y⁴)C₁₋₁₅alkylene-Z². R¹⁰ may be C₁₋₁₉alkyl and R¹¹ is —X²—C₂₋₁₆alkylene-Z².

R¹⁰ may be C₁₁alkyl and R¹¹ is —X²—C(=Y⁴)C₁₋₁₅alkyl (e.g., —O—C(=O)C₉alkyl) or —X²—C₂₋₁₆alkyl (e.g., —O—C₁₀alkyl). For example, —CH(R¹⁰)(R¹¹) may be

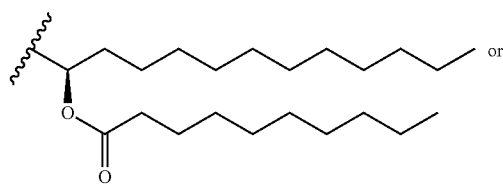

R¹⁰ may be C₁₁alkyl and R¹¹ is —X²—C(=Y⁴)C₁₋₁₅alkyl (e.g., —O—C(=O)C₉alkyl), —X²—C₂₋₁₆alkyl (e.g., —O—C₁₀alkyl), —X²—C(=Y⁴)C₁₋₁₅alkylene-Z² (e.g., —O—C(=O)C₇alkylene-Z²), or —X²—C₂₋₁₆alkylene-Z² (e.g., —O—C₈₋₉alkylene-Z²). For example, —CH(R¹⁰)(R¹¹) may be

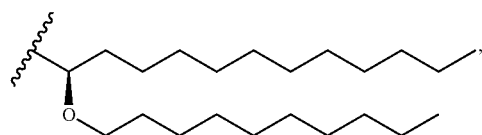

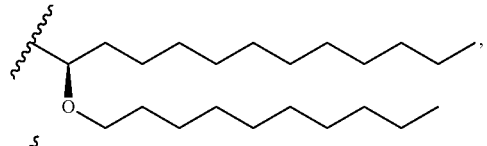

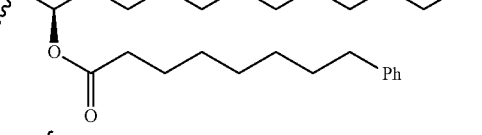

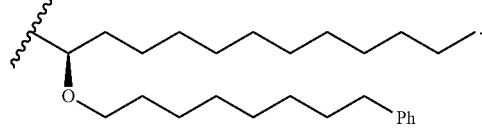

In further embodiments having at least one occurrence of —CH(R¹⁰)(R¹¹), at least one occurrence of R¹⁰ and R¹¹ may be defined as follows. R¹⁰ may be C₃₋₂₁alkyl and R¹¹ is —X²—C(=Y⁴)C₁₋₁₅alkylene-Z¹—C₁₋₁₅alkyl. In some embodiments, R¹⁰ may be C₃₋₂₁alkyl and R¹¹ is —CH₂—C(=Y⁴)C₁₋₁₅alkylene-Z¹—C₁₋₁₅alkyl. In some embodiments, R¹⁰ may be C₃₋₂₁alkyl and R¹¹ is —X²—C₂₋₁₆alkylene-Z¹—C₁₋₁₅alkyl. In some embodiments, R¹⁰ may be C₃₋₂₁alkyl and R¹¹ is —C₃₋₁₇alkylene-Z¹—C₁₋₁₅alkyl. In some embodiments, R¹⁰ may be C₃₋₂₁alkyl and R¹¹ is C₃₋₁₇alkyl. In some embodiments, R¹⁰ may be C₃₋₂₁alkyl and R¹¹ is —X²—C₂₋₁₆alkyl. In some embodiments, R¹⁰ may be C₃₋₂₁alkyl and R¹¹ is —CH₂—X²—C₁₋₁₅alkyl.

In further embodiments having at least one occurrence of —CH(R¹⁰)(R¹¹), at least one occurrence of R¹⁰ and R¹¹ may be defined as follows. R¹⁰ may be C₁₋₂₁alkyl and R¹¹ is —X²—C(=Y⁴)C₁₋₁₅alkylene-Z¹—C₁₋₁₅alkyl. R¹¹ may be C₁₋₂₁alkyl and R¹¹ is —CH₂—C(=Y⁴)C₁₋₁₅alkylene-Z¹—C₁₋₁₅alkyl. R¹⁰ may be C₁₋₂₁alkyl and R¹¹ is —X²—C₂₋₁₆alkylene-Z¹—C₁₋₁₅alkyl. R¹⁰ may be C₁₋₂₁alkyl and R¹¹ is —C₃₋₁₇alkylene-Z¹—C₁₋₁₅alkyl. R¹⁰ may be C₁₋₂₁alkyl and R¹¹ is C₃₋₁₇alkyl. R¹⁰ may be C₁₋₂₁alkyl and R¹¹ is —X²—C₂₋₁₆alkyl. R¹⁰ may be C₁₋₂₁alkyl and R¹¹ is —X²—C(=Y⁴)C₁₋₁₅alkyl. R¹⁰ may be C₁₋₂₁alkyl and R¹¹ is —CH₂—C(=Y⁴)C₁₋₁₅alkyl. R¹⁰ may be C₁₋₂₁alkyl and R¹¹ is —CH₂—X²—C₁₋₁₅alkylene-Z¹—C₁₋₁₅alkyl.

In other embodiments, $R^{10}$ may be —$X^1$—$C_{2-20}$alkyl. In further embodiments having at least one occurrence of —CH($R^{10}$)($R^{11}$), at least one occurrence of $R^{10}$ and $R^{11}$ may be defined as follows. $R^{10}$ may be —$X^1$—$C_{2-20}$alkyl and $R^{11}$ is —$X^2$—C(=$Y^4$)$C_{1-15}$alkylene-$Z^1$—$C_{1-15}$alkyl. $R^{10}$ may be —$X^1$—$C_{2-20}$alkyl and $R^{11}$ is —$CH_2$—C(=$Y^4$)$C_{1-15}$alkylene-$Z^1$—$C_{1-15}$alkyl. $R^{10}$ may be —$X^1$—$C_{2-20}$alkyl and $R^{11}$ is —$X^2$—$C_{2-16}$alkylene-$Z^1$—$C_{1-15}$alkyl. $R^{10}$ may be —$X^1$—$C_{2-20}$alkyl and $R^{11}$ is —$C_{3-17}$alkylene-$Z^1$—$C_{1-15}$alkyl. $R^{10}$ may be —$X^1$—$C_{2-20}$alkyl and $R^{11}$ is $C_{3-17}$alkyl. $R^{10}$ may be —$X^1$—$C_{2-20}$alkyl and $R^{11}$ is —$X^2$—$C_{2-16}$alkyl. $R^{10}$ may be —$X^1$—$C_{2-20}$alkyl and $R^{11}$ is —$CH_2$—$X^2$—$C_{1-15}$alkyl. $R^{10}$ may be —$X^1$—$C_{2-20}$alkyl and $R^{11}$ is —$X^2$—C(=$Y^4$)$C_{1-15}$alkyl. $R^{10}$ may be —$X^1$—$C_{2-20}$alkyl and $R^{11}$ is —$CH_2$—C(=$Y^4$)$C_{1-15}$alkyl. $R^{10}$ may be —$X^1$—$C_{2-20}$alkyl and $R^{11}$ is —$CH_2$—$X^2$—$C_{1-15}$alkylene-$Z^1$—$C_{1-15}$alkyl.

In other embodiments, $R^1$ may be —$CH_2$—$X^1$—$C_{1-19}$alkyl. In further embodiments having at least one occurrence of —CH($R^{10}$)($R^{11}$), at least one occurrence of $R^{10}$ and $R^{11}$ may be defined as follows. For example, $R^{10}$ may be —$CH_2$—$X^1$—$C_{1-19}$alkyl and $R^{11}$ is $C_{3-17}$alkyl. $R^{10}$ may be —$CH_2$—$X^1$—$C_{1-19}$alkyl and $R^{11}$ is —$CH_2$—$X^2$—$C_{1-15}$alkyl. $R^{10}$ may be —$CH_2$—$X^1$—$C_{1-19}$alkyl and $R^{11}$ is —$X^2$—$C_{2-16}$alkyl. $R^{10}$ may be —$CH_2$—$X^1$—$C_{1-19}$alkyl and $R^{11}$ is —$X^2$—C(=$Y^4$)$C_{1-15}$alkyl. $R^{10}$ may be —$CH_2$—$X^1$—$C_{1-19}$alkyl and $R^{11}$ is —$CH_2$—C(=$Y^4$)$C_{1-15}$alkyl. $R^{10}$ may be —$CH_2$—$X^1$—$C_{1-19}$alkyl and $R^{11}$ is —$X^2$—C(=$Y^4$)$C_{1-15}$alkylene-$Z^1$—$C_{1-15}$alkyl. $R^{10}$ may be —$CH_2$—$X^1$—$C_{1-19}$alkyl and $R^{11}$ is —$CH_2$—C(=$Y^4$)$C_{1-15}$alkylene-$Z^1$—$C_{1-15}$alkyl. $R^{10}$ may be —$CH_2$—$X^1$—$C_{1-19}$alkyl and $R^{11}$ is —$C_{3-17}$alkylene-$Z^1$—$C_{1-15}$alkyl. $R^{10}$ may be —$CH_2$—$X^1$—$C_{1-19}$alkyl and $R^{11}$ is —$X^2$—$C_{2-16}$alkylene-$Z^1$—$C_{1-15}$alkyl. $R^{10}$ may be —$CH_2$—$X^1$—$C_{1-19}$alkyl and $R^{11}$ is —$CH_2$—$X^2$—$C_{1-15}$alkylene-$Z^1$—$C_{1-15}$alkyl.

In some embodiments, $R^{10}$ is $C_{1-19}$alkyl and $R^{11}$ is —$X^2$—C(=$Y^4$)$C_{1-15}$alkyl. In other embodiments, $R^{10}$ is $C_{1-19}$alkyl and $R^{11}$ is —$CH_2$—C(=$Y^4$)$C_{1-15}$alkyl. In other embodiments, $R^{10}$ is $C_{1-19}$alkyl and $R^{11}$ is $C_{3-17}$alkyl. In other embodiments, $R^{10}$ is $C_{1-19}$alkyl and $R^{11}$ is —$X^2$—$C_{2-16}$alkyl. In other embodiments, $R^{10}$ is $C_{1-19}$alkyl and $R^{11}$ is $X^2$—C(=$Y^4$)$C_{1-15}$alkylene-$Z^1$—$C_{1-15}$alkyl. In other embodiments, $R^{10}$ is $C_{1-19}$alkyl and $R^{11}$ is —$CH_2$—C(=$Y^4$)$C_{1-15}$alkylene-$Z^1$—$C_{1-15}$alkyl. In other embodiments, $R^{10}$ is $C_{1-19}$alkyl and $R^{11}$ is $X^2$—$C_{2-16}$alkylene-$Z^1$—$C_{1-15}$alkyl. In other embodiments, $R^{10}$ is $C_{1-19}$alkyl and $R^{11}$ is —$X^2$—C(=$Y^4$)$C_{1-15}$alkylene-$Z^2$. In other embodiments, $R^{10}$ is $C_{1-19}$alkyl and $R^{11}$ is —$X^2$—$C_{2-16}$alkylene-$Z^2$.

In further embodiments, $R^{10}$ is $C_{11}$alkyl and $R^{11}$ is —$X^2$—C(=$Y^4$)$C_{1-15}$alkyl (e.g., —O—C(=O)$C_9$alkyl) or —$X^2$—$C_{2-16}$alkyl (e.g. —O—$C_{10}$alkyl). For example, —CH($R^{10}$)($R^{11}$) may be

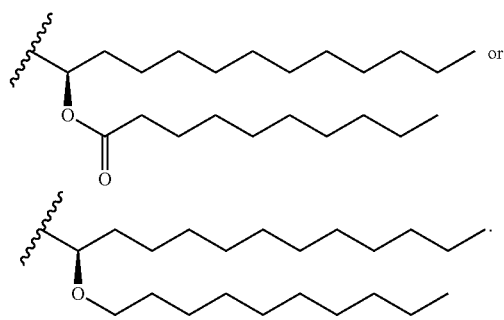

In further embodiments, $R^{10}$ is $C_{11}$alkyl and $R^{11}$ is —$X^2$—C(=$Y^4$)$C_{1-15}$alkyl (e.g., —O—C(=O)$C_9$alkyl), —$X^2$—$C_{2-16}$alkyl (e.g., —O—$C_{10}$alkyl), —$X^2$—C(=$Y^4$)$C_{1-15}$alkylene-$Z^2$ (e.g., —O—C(=O)$C_7$alkylene-$Z^2$), or —$X^2$—$C_{2-16}$alkylene-$Z^2$ (e.g., —O—$C_{8-9}$alkylene-$Z^2$). For example, —CH($R^{10}$)($R^{11}$) may be

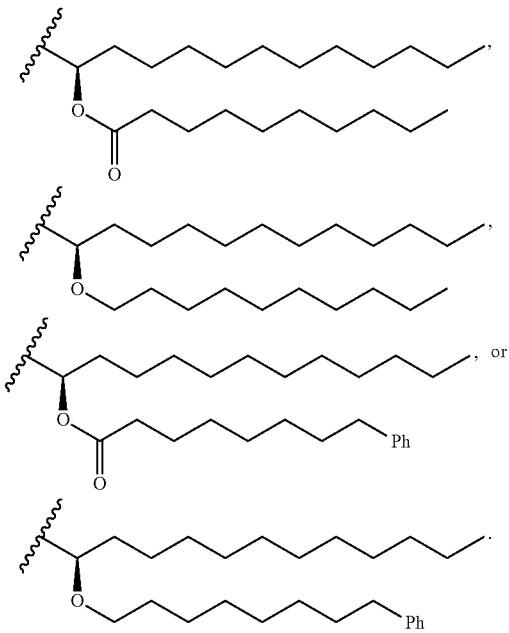

In some embodiments, $R^{10}$ is $C_{3-21}$alkyl and $R^{11}$ is —$X^2$—C(=$Y^4$)$C_{1-15}$alkylene-$Z^1$—$C_{1-15}$alkyl. In some embodiments, $R^{10}$ is $C_{3-21}$alkyl and $R^{11}$ is —$CH_2$—C(=$Y^4$)$C_{1-15}$alkylene-$Z^1$—$C_{1-15}$alkyl. In some embodiments, $R^{10}$ is $C_{3-21}$alkyl and $R^{11}$ is —$X^2$—$C_{2-16}$alkylene-$Z^1$—$C_{1-15}$alkyl. In some embodiments, $R^{10}$ is $C_{3-21}$alkyl and $R^{11}$ is —$C_{3-17}$alkylene-$Z^1$—$C_{1-15}$alkyl. In some embodiments, $R^{10}$ is $C_{3-21}$alkyl and $R^{11}$ is $C_{3-17}$alkyl. In some embodiments, $R^{10}$ is $C_{3-21}$alkyl and $R^{11}$ is —$X^2$—$C_{2-16}$alkyl. In some embodiments, $R^1$ is $C_{3-21}$alkyl and $R^{11}$ is —$CH_2$—$X^2$—$C_{1-15}$alkyl.

In some embodiments, $R^{10}$ is $C_{1-21}$alkyl and $R^{11}$ is —$X^2$—C(=$Y^4$)$C_{1-15}$alkylene-$Z^1$—$C_{1-15}$alkyl. In some embodiments, $R^1$ is $C_{1-21}$alkyl and $R^{11}$ is —$CH_2$—C(=$Y^4$)$C_{1-15}$alkylene-$Z^1$—$C_{1-15}$alkyl. In some embodiments, $R^{10}$ is $C_{1-21}$alkyl and $R^{11}$ is —$X^2$—$C_{2-16}$alkylene-$Z^1$—$C_{1-15}$alkyl. In some embodiments, $R^{10}$ is $C_{1-21}$alkyl and $R^{11}$ is —$C_{3-17}$alkylene-$Z^1$—$C_{1-15}$alkyl. In some embodiments, $R^{10}$ is $C_{1-21}$alkyl and $R^{11}$ is $C_{3-17}$alkyl. In some embodiments, $R^{10}$ is $C_{1-21}$alkyl and $R^{11}$ is —$X^2$—$C_{2-16}$alkyl. In some embodiments, $R^{10}$ is $C_{1-21}$alkyl and $R^{11}$ is —$CH_2$—$X^2$—$C_{1-15}$alkyl. In some embodiments, $R^{10}$ is $C_{1-21}$alkyl and $R^{11}$ is —$X^2$—C(=$Y^4$)$C_{1-15}$alkyl. In some embodiments, $R^{10}$ is $C_{1-21}$alkyl and $R^{11}$ is —$CH_2$—C(=$Y^4$)$C_{1-15}$alkyl. In some embodiments, $R^{10}$ is $C_{1-21}$alkyl and $R^{11}$ is —$CH_2$—$X^2$—$C_{1-15}$alkylene-$Z^1$—$C_{1-15}$alkyl.

In other embodiments, $R^{10}$ is —$X^1$—$C_{2-20}$alkyl. For example, in some embodiments, $R^{10}$ is —$X^1$—$C_{2-20}$alkyl and $R^{11}$ is —$X^2$—C(=$Y^4$)$C_{1-15}$alkylene-$Z^1$—$C_{1-15}$alkyl. In some embodiments, $R^{10}$ is —$X^1$—$C_{2-20}$alkyl and $R^{11}$ is —$CH_2$—C(=$Y^4$)$C_{1-15}$alkylene-$Z^1$—$C_{1-15}$alkyl. In some embodiments, $R^{10}$ is —$X^1$—$C_{2-20}$alkyl and $R^{11}$ is —$X^2$—$C_{2-16}$alkylene-$Z^1$—$C_{1-15}$alkyl. In some embodiments, $R^{10}$ is —$X^1$—$C_{2-20}$alkyl and $R^{11}$ is —$C_{3-17}$alkylene-$Z^1$—$C_{1-15}$alkyl. In some embodiments, $R^{10}$ is —$X^1$—$C_{2-20}$alkyl and $R^{11}$ is $C_{3-17}$alkyl. In some embodiments, $R^{10}$ is —$X^1$—$C_{2-20}$alkyl and $R^{11}$ is —$X^2$—$C_{2-16}$alkyl. In some embodiments, $R^{10}$ is —$X^1$—$C_{2-20}$alkyl and $R^{11}$ is —$CH_2$—$X^2$—$C_{1-15}$alkyl.

In some embodiments, $R^{10}$ is —$X^1$—$C_{2-20}$alkyl and $R^{11}$ is —$X^2$—C(=$Y^4$)$C_{1-15}$alkyl. In some embodiments, $R^{10}$ is —$X^1$—$C_{2-20}$alkyl and $R^{11}$ is —$CH_2$—C(=$Y^4$)$C_{1-15}$alkyl. In some embodiments, $R^{10}$ is —$X^1$—$C_{2-20}$alkyl and $R^{11}$ is —$CH_2$—$X^2$—$C_{1-15}$alkylene-$Z^1$—$C_{1-15}$alkyl.

In other embodiments, $R^{10}$ is —$CH_2$—$X^1$—$C_{1-19}$alkyl. For example, in some embodiments, $R^{10}$ is —$CH_2$—$X^1$—$C_{1-19}$alkyl and $R^{11}$ is $C_{3-17}$alkyl. In other embodiments, $R^{10}$ is —$CH_2$—$X^1$—$C_{1-19}$alkyl and $R^{11}$ is —$CH_2$—$X^2$—$C_{1-15}$alkyl.

In other embodiments, $R^{10}$ is —$CH_2$—$X^1$—$C_{1-19}$alkyl and $R^{11}$ is —$X^2$—$C_{2-16}$alkyl. In other embodiments, $R^{10}$ is —$CH_2$—$X^1$—$C_{1-19}$alkyl and $R^{11}$ is —$X^2$—C(=$Y^4$)$C_{1-15}$alkyl. In other embodiments, $R^{10}$ is —$CH_2$—$X^1$—$C_{1-19}$alkyl and $R^{11}$ is —$CH_2$—C(=$Y^4$)$C_{1-15}$alkyl. In other embodiments, $R^{10}$ is —$CH_2$—$X^1$—$C_{1-19}$alkyl and $R^{11}$ is —$X^2$—C(=$Y^4$)$C_{1-15}$alkylene-$Z^1$—$C_{1-15}$alkyl. In other embodiments, $R^{10}$ is —$CH_2$—$X^1$—$C_{1-19}$alkyl and $R^{11}$ is —$CH_2$—C(=$Y^4$)$C_{1-15}$alkylene-$Z^1$—$C_{1-15}$alkyl. In other embodiments, $R^{10}$ is —$CH_2$—$X^1$—$C_{1-19}$alkyl and $R^{11}$ is —$C_{3-17}$alkylene-$Z^1$—$C_{1-15}$alkyl. In other embodiments, $R^{10}$ is —$CH_2$—$X^1$—$C_{1-19}$alkyl and $R^{11}$ is —$X^2$—$C_{2-16}$alkylene-$Z^1$—$C_{1-15}$alkyl. In other embodiments, $R^{10}$ is —$CH_2$—$X^1$—$C_{1-19}$alkyl and $R^{11}$ is —$CH_2$—$X^2$—$C_{1-15}$alkylene-$Z^1$—$C_{1-15}$alkyl.

In some embodiments, $Y^4$ is O (e.g., —$X^2$—C(=O)$C_{1-15}$alkyl).

In some embodiments, $X^2$ is O (e.g., $R^{11}$ is —$C_{2-16}$alkyl, —O—C(=O)$C_{1-15}$alkyl).

In some embodiments, $Y^1$, $Y^2$, and $Y^3$ are O.

In some embodiments, $X^3$ is O.

$R^{3a}$, $R^{3b}$, and $R^{3c}$ are each independently $CO_2H$, —$OSO_3H$, —OP(O)(OH)$_2$, —$C_{1-6}$alkylene-$CO_2H$ (e.g., $CH_2CO_2H$), —$C_{1-6}$alkylene-$OSO_3H$ (e.g., $CH_2OSO_3H$), —$C_{1-6}$alkylene-OP(O)(OH)$_2$ (e.g., —$CH_2OP(O)(OH)_2$), —$OC_{1-6}$alkylene-P(O)(OH)$_2$ (e.g., —$OCH_2P(O)(OH)_2$), —$C_{1-6}$alkylene-P(O)(OH)$_2$ (e.g., $CH_2P(O)(OH)_2$), —$C_{1-6}$haloalkylene-P(O)(OH)$_2$ (e.g., $CF_2P(O)(OH)_2$), H, or an ester of the $CO_2H$, —$OSO_3H$, —OP(O)(OH)$_2$, —$C_{1-6}$alkylene-$CO_2H$, —$C_{1-6}$alkylene-$OSO_3H$, —$C_{1-6}$alkylene-OP(O)(OH)$_2$, —$OC_{1-6}$alkylene-P(O)(OH)$_2$, —$C_{1-6}$alkylene-P(O)(OH)$_2$, or —$C_{1-6}$haloalkylene-P(O)(OH)$_2$.

In some embodiments, $R^{3a}$ is —OP(O)(OH)$_2$.

In some embodiments, $R^{3a}$ is —$OSO_3H$.

In some embodiments, $R^{3a}$ is —$OCH_2P(O)(OH)_2$.

$R^{3d}$ is $CO_2H$, —$SO_3H$, —P(O)(OH)$_2$, —$C_{1-6}$alkylene-$CO_2H$ (e.g., —$CH_2CO_2H$), —$C_{1-6}$alkylene-$OSO_3H$ (e.g., —$CH_2OSO_3H$), —$C_{1-6}$alkylene-OP(O)(OH)$_2$ (e.g., —$CH_2OP(O)(OH)_2$), —$OC_{1-6}$alkylene-P(O)(OH)$_2$ (e.g., —$OCH_2P(O)(OH)_2$), —$C_{1-6}$alkylene-P(O)(OH)$_2$ (e.g., $CH_2P(O)(OH)_2$), —$C_{1-6}$haloalkylene-P(O)(OH)$_2$ (e.g., $CF_2P(O)(OH)_2$), H, $C_{1-6}$alkyl (e.g., methyl, ethyl, isopropyl, tert-butyl), $C_{1-6}$haloalkyl (e.g., trifluoromethyl, trifluoroethyl), $C_{3-8}$cycloalkyl (e.g., cyclopropyl, cyclobutyl, etc.), or an ester of the $CO_2H$, —$OSO_3H$, —OP(O)(OH)$_2$, —$C_{1-6}$alkylene-$CO_2H$, —$C_{1-6}$alkylene-$OSO_3H$, —$C_{1-6}$alkylene-OP(O)(OH)$_2$, —$OC_{1-6}$alkylene-P(O)(OH)$_2$, —$C_{1-6}$alkylene-P(O)(OH)$_2$, or —$C_{1-6}$haloalkylene-P(O)(OH)$_2$.

In some embodiments, $R^{4a}$ is $CH_2OH$.

In some embodiments, $R^1$ is

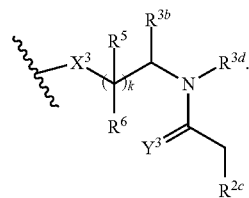

In further embodiments k is 1; $R^{3b}$ is hydrogen or COOH, or an ester thereof; and $R^{3d}$, $R^5$, and $R^6$ are each hydrogen In some embodiments, $R^1$ is

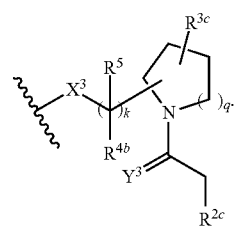

For example, $R^1$ may be

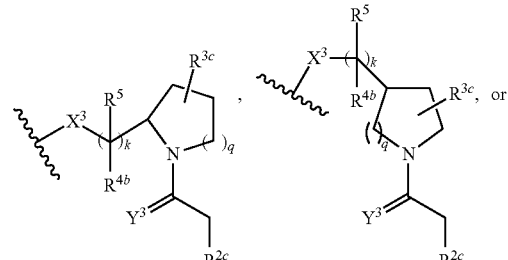

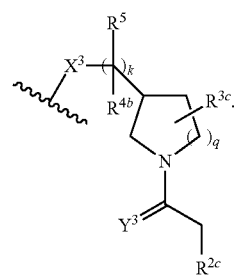

Particular examples of $R^1$ include

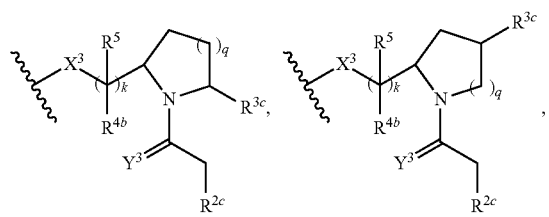

-continued

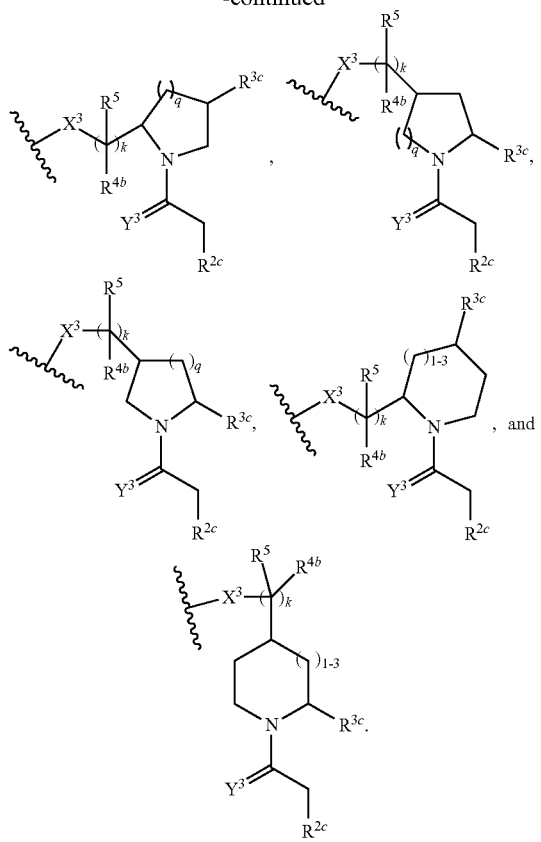

In the foregoing examples, are further embodiments where q is an integer from 1-4.

In other embodiments, $R^1$ is

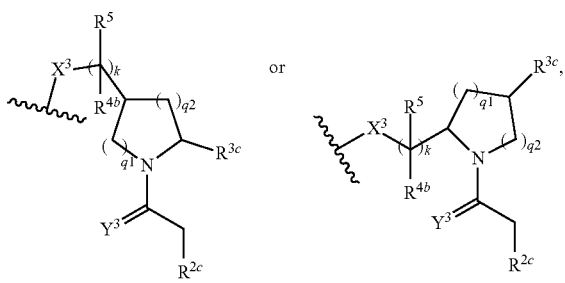

where q1 and q2 are integers from 0-4, provided that q1+q2 is an integer from 1-4.

In some embodiments, $R^1$ is

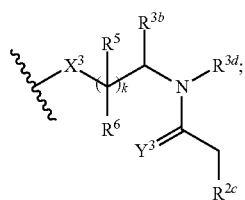

$R^{2a}$, $R^{2b}$, and $R^{2c}$ are each independently —CH($R^{10}$)($R^{11}$); $R^{10}$ is $C_{1-21}$alkyl; $R^{11}$, at each occurrence, is independently —$X^2$—$C_{2-16}$alkyl, —$X^2$—C(=$Y^4$)$C_{1-15}$alkyl, —$X^2$—C(=$Y^4$)$C_{1-15}$alkylene-$Z^2$, or —$X^2$—$C_{2-16}$alkylene-$Z^2$; $R^{3a}$ is —OSO$_3$H, —OP(O)(OH)$_2$, or —OC$_{1-6}$alkylene-P(O)(OH)$_2$; $R^{3b}$ is H, CO$_2$H, or an ester thereof; $R^{3d}$, $R^5$, and $R^6$ are each hydrogen; $Y^1$, $Y^2$, $Y^3$, and $Y^4$ are O; $X^2$ and $X^3$ are O; $R^{4a}$ is CH$_2$OH; and k is 1.

In some embodiments, $R^1$ is

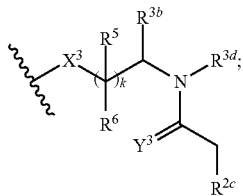

$R^{2a}$, $R^{2b}$, and $R^{2c}$ are each independently —CH($R^{10}$)($R^{11}$); $R^{10}$ is $C_{1-21}$alkyl; $R^{11}$, at each occurrence, is independently —$X^2$—$C_{2-16}$alkyl, —$X^2$—C(=$Y^4$)$C_{1-15}$alkyl, or —$X^2$—C(=$Y^4$)$C_{1-15}$alkylene-$Z^2$; $R^{3a}$ is —OSO$_3$H, —OP(O)(OH)$_2$, or —OC$_{1-6}$alkylene-P(O)(OH)$_2$; $R^{3b}$ is H, CO$_2$H, or an ester thereof; $R^{3d}$, $R^5$, and $R^6$ are each hydrogen; $Y^1$, $Y^2$, $Y^3$, and $Y^4$ are O; $X^2$ and $X^3$ are O; $R^{4a}$ is CH$_2$OH; and k is 1.

In some embodiments, $R^1$ is

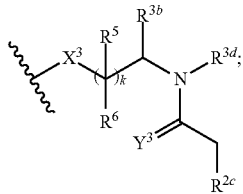

$R^{2a}$, $R^{2b}$, and $R^{2c}$ are each independently —CH($R^{10}$)($R^{11}$); $R^{10}$ is $C_{1-21}$alkyl; $R^{11}$ is —$X^2$—$C_{2-16}$alkyl or —$X^2$—C(=$Y^4$)$C_{1-15}$alkyl; $R^{3a}$ is —OSO$_3$H or —OP(O)(OH)$_2$; $R^{3b}$ is H, CO$_2$H, or an ester thereof; $R^{3d}$, $R^5$, and $R^6$ are each hydrogen; $Y^1$, $Y^2$, $Y^3$, and $Y^4$ are O; $X^2$ and $X^3$ are O; $R^{4a}$ is CH$_2$OH; and k is 1.

Compounds of formula (I) may have formula (I-a)

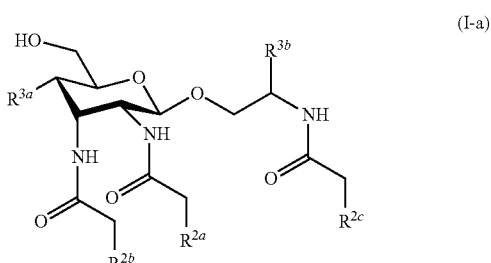

wherein $R^{2a}$, $R^{2b}$, $R^{2c}$, $R^{3a}$, and $R^{3b}$ are as defined herein. $R^{3a}$ may be —OP(O)(OH)$_2$, —OSO$_3$H, or —OCH$_2$—P(O)(OH)$_2$, wherein $R^{2a}$, $R^{2b}$, $R^{2c}$, and $R^{3b}$ are as defined herein. $R^{3a}$ may be —OP(O)(OH)$_2$, —OSO$_3$H, or —OCH$_2$—P(O)(OH)$_2$, wherein $R^{3b}$ is H, CO$_2$H, or an ester of the CO$_2$H, and $R^{2a}$, $R^{2b}$, and $R^{2c}$ are as defined herein. For example, $R^{2a}$, $R^{2b}$, and $R^{2c}$ may be —CH($R^{10}$)($R^{11}$), wherein $R^{10}$, at each occurrence, is independently $C_{1-21}$alkyl, —$X^1$—$C_{2-20}$alkyl, or —CH$_2$—$X^1$—$C_{1-19}$alkyl; $R^{11}$, at each occurrence, is independently $C_{3-17}$alkyl, —$X^2$—$C_{2-16}$alkyl, —CH$_2$—$X^2$—$C_{1-15}$alkyl, —$X^1$—C(=$Y^4$)$C_{1-15}$alkyl, —CH$_2$—C(=Y$^4$)C$_{1-15}$alkyl, —X$^2$—C(=Y$^4$)C$_{1-15}$alkylene-Z$^1$—C$_{1-15}$alkyl, —CH$_2$—C(=Y$^4$)C$_{1-15}$alkylene-Z$^1$—C$_{1-15}$alkyl, —C$_{3-17}$alkylene-Z$^1$—C$_{1-15}$alkyl, —X$^2$—C$_{2-16}$alkylene-Z$^1$—C$_{1-15}$alkyl, —CH$_2$—X$^2$—C$_{1-15}$alkylene-Z$^1$—C$_{1-15}$alkyl, —X$^2$—C(=Y$^4$)C$_{1-15}$alkylene-Z$^2$, or —X$^2$—C$_{2-16}$alkylene-Z$^2$; and X$^1$, X$^2$, Y$^4$, Z$^1$, and Z$^2$ are as defined herein. R$^{2a}$, R$^{2b}$, and R$^{2c}$ may be —CH(R$^{10}$)(R$^{11}$), wherein R$^{10}$, at each occurrence, is independently C$_{1-21}$alkyl, —X$^1$—C$_{2-20}$alkyl, or —CH$_2$—X$^1$—C$_{1-19}$alkyl; R$^{11}$, at each occurrence, is independently C$_{3-17}$alkyl, —X$^2$—C$_{2-16}$alkyl, —CH$_2$—X$^2$—C$_{1-15}$alkyl, —X$^1$—C(=Y$^4$)C$_{1-15}$alkyl, —CH$_2$—C(=Y$^4$)C$_{1-15}$alkyl, —X$^2$—C(=Y$^4$)C$_{1-15}$alkylene-Z$^1$—C$_{1-15}$alkyl, —CH$_2$—C(=Y$^4$)C$_{1-15}$alkylene-Z$^1$—C$_{1-15}$alkyl, —C$_{3-17}$alkylene-Z$^1$—C$_{1-15}$alkyl, —X$^2$—C$_{2-16}$alkylene-Z$^1$—C$_{1-15}$alkyl, —CH$_2$—X$^2$—C$_{1-15}$alkylene-Z$^1$—C$_{1-15}$alkyl, or —X$^2$—C(=Y$^4$)C$_{1-15}$alkylene-Z$^2$; and X$^1$, X$^2$, Y$^4$, Z$^1$, and Z$^2$ are as defined herein.

Compounds of formula (I) may have formula (II)

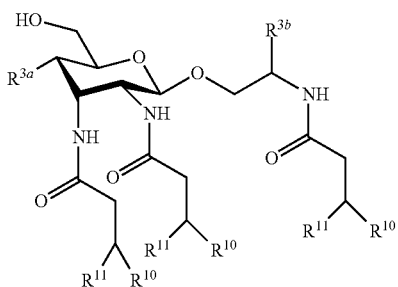

(II)

wherein R$^{10}$, at each occurrence, is independently C$_{1-21}$alkyl, —X$^1$—C$_{2-20}$alkyl, or —CH$_2$—X$^1$—C$_{1-19}$alkyl; R$^{11}$, at each occurrence, is independently C$_{3-17}$alkyl, —X$^2$—C$_{2-6}$alkyl, —CH$_2$—X$^2$—C$_{1-15}$alkyl, —X$^1$—C(=Y$^4$)C$_{1-15}$alkyl, —CH$_2$—C(=Y$^4$)C$_{1-15}$alkyl, —X$^2$—C(=Y$^4$)C$_{1-15}$alkylene-Z$^1$—C$_{1-15}$alkyl, —CH$_2$—C(=Y$^4$)C$_{1-15}$alkylene-Z$^1$—C$_{1-15}$alkyl, —C$_{3-17}$alkylene-Z$^1$—C$_{1-15}$alkyl, —X$^2$—C$_{2-16}$alkylene-Z$^1$—C$_{1-15}$alkyl, —CH$_2$—X$^2$—C$_{1-15}$alkylene-Z$^1$—C$_{1-15}$alkyl, —X$^2$—C(=Y$^4$)C$_{1-15}$alkylene-Z$^2$, or —X$^2$—C$_{2-16}$alkylene-Z$^2$; and R$^{3a}$, R$^{3b}$, X$^1$, X$^2$, Y$^4$, Z$^1$, and Z$^2$ are as defined herein. In some embodiments, R$^{10}$ is C$_{1-21}$alkyl; R$^{11}$, at each occurrence, is independently —O—C(=O)C$_{1-15}$alkyl, —O—C$_{2-16}$alkyl, —O—C(=O)C$_{1-15}$alkylene-Z$^2$, or —X$^2$—C$_{2-16}$alkylene-Z$^2$; R$^{3a}$, is —OP(O)(OH)$_2$, —OSO$_3$H, or —OCH$_2$—P(O)(OH)$_2$; R$^{3b}$ is H, CO$_2$H, or an ester of the CO$_2$H; and Z$^2$, at each occurrence, is independently phenyl or a 5- to 6-membered heteroaryl, wherein Z$^2$ is optionally substituted with 1-5 substituents independently selected from C$_{1-4}$alkyl, C$_{1-4}$haloalkyl, —OC$_{1-4}$alkyl, —OC$_{1-4}$haloalkyl, cyano, and halogen. In some embodiments, R$^{10}$ is C$_{1-21}$alkyl; R$^{11}$, at each occurrence, is independently —O—C(=O)C$_{1-15}$alkyl, —O—C$_{2-16}$alkyl, or —O—C(=O)C$_{1-15}$alkylene-Z$^2$; R$^{3a}$, is —OP(O)(OH)$_2$, —OSO$_3$H, or —OCH$_2$—P(O)(OH)$_2$; R$^{3b}$ is H, CO$_2$H, or an ester of the CO$_2$H; and Z$^2$, at each occurrence, is independently phenyl or a 5- to 6-membered heteroaryl, wherein Z$^2$ is optionally substituted with 1-5 substituents independently selected from C$_{1-4}$alkyl, C$_{1-4}$haloalkyl, —OC$_{1-4}$alkyl, —OC$_{1-4}$haloalkyl, cyano, and halogen. In some embodiments, R$^{10}$ is C$_{1-2}$alkyl; R$^{11}$, at each occurrence, is independently —O—C(=O)C$_{1-15}$alkyl, —O—C$_{2-16}$alkyl, or —O—C(=O)C$_{1-15}$alkylene-Z$^2$; R$^{3a}$, is —OP(O)(OH)$_2$, —OSO$_3$H, or —OCH$_2$—P(O)(OH)$_2$; R$^{3b}$ is H, CO$_2$H, or an ester of the CO$_2$H; and Z$^2$, at each occurrence, is independently phenyl optionally substituted with 1-5 substituents independently selected from C$_{1-4}$alkyl, C$_{1-4}$haloalkyl, —OC$_{1-4}$alkyl, —OC$_{1-4}$haloalkyl, cyano, and halogen.

In the embodiments herein are further embodiments wherein R$^{2a}$, R$^{2b}$, and R$^{2c}$ are each —CH(R$^{10}$)(R$^{11}$), each instance of R$^1$ is the same (e.g., C$_{1-21}$alkyl such as C$_{11}$alkyl), and each instance of R$^{11}$ is the same (e.g., —O—C(=O)C$_{1-15}$alkyl such as —O—C(=O)C$_9$alkyl, —O—C$_{2-16}$alkyl such as —O—C$_{10}$alkyl, —O—C(=O)C$_{1-15}$alkylene-Z$^2$ such as —O—C(=O)C$_7$alkylene-Z$^2$). In other embodiments, each occurrence of R$^1$ is the same (e.g., C$_{1-21}$alkyl such as C$_{11}$alkyl), and R$^{11}$ is not the same in all occurrences (e.g., R$^{11}$ at R$^{2b}$ is —O—C(=O)C$_{1-15}$alkylene-Z$^2$ such as —O—C(=O)C$_7$alkylene-Z$^2$, and R$^{11}$ at R$^{2a}$ and R$^{2c}$ is —O—C(=O)C$_{1-15}$alkyl such as —O—C(=O)C$_9$alkyl).

The esters at R$^{3a}$, R$^{3b}$, R$^{3c}$, R$^{3d}$, R$^{4a}$, and R$^{4b}$ include alkyl esters (e.g., C$_{1-6}$alkyl esters), haloalkyl esters (e.g., C$_{1-6}$haloalkyl esters), and aryl esters (e.g., optionally substituted phenyl or naphthyl esters).

In some embodiments, the compound of formula (I) is

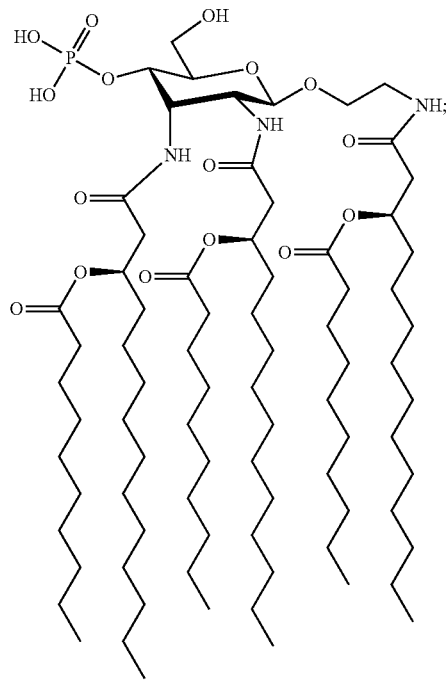

-continued
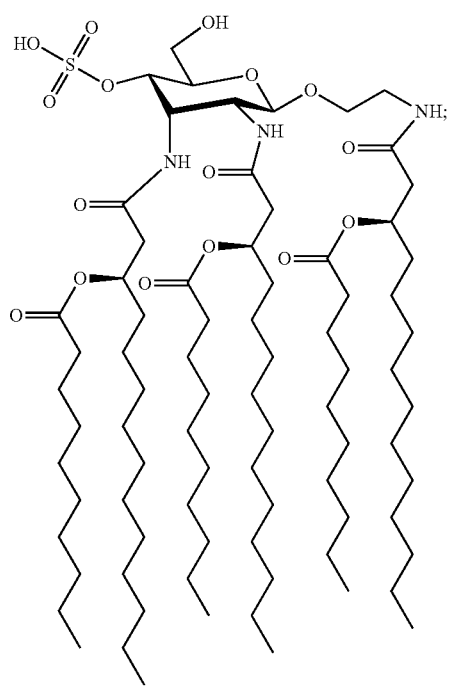
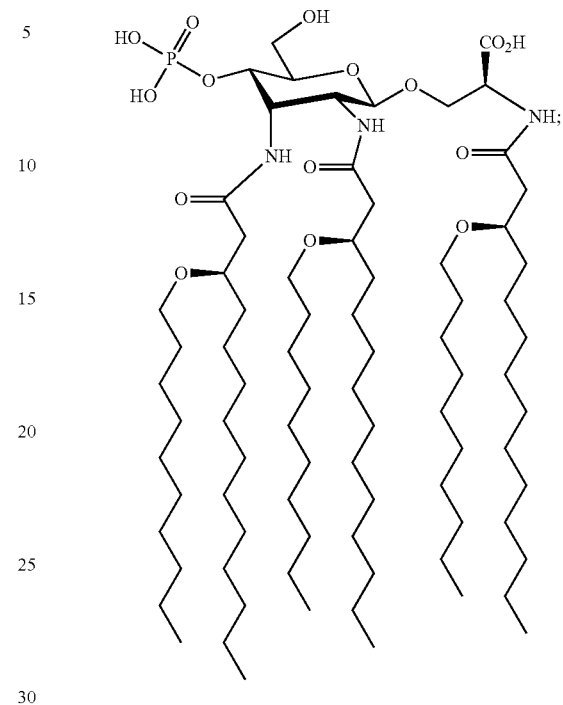
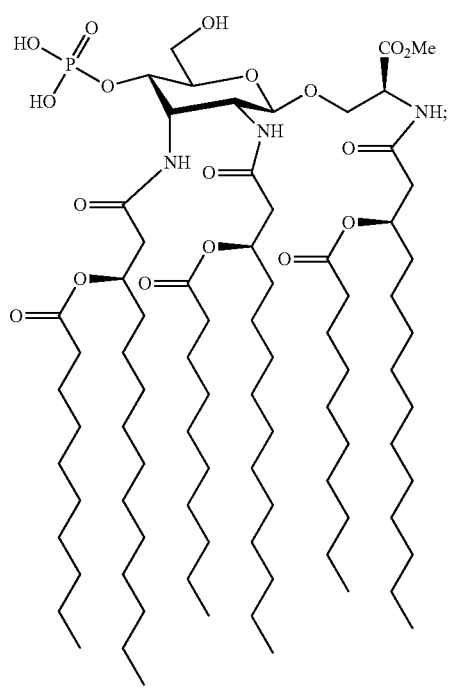
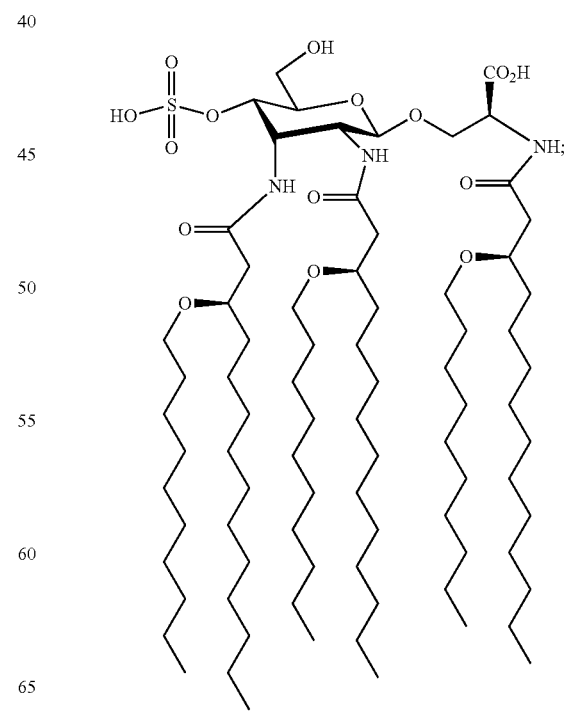

21
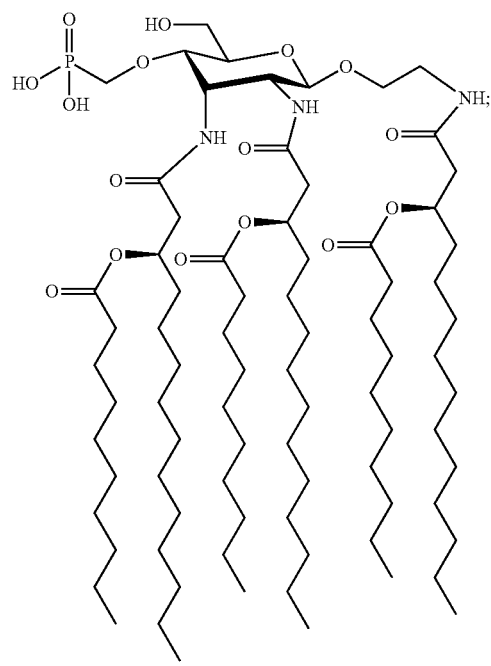
22
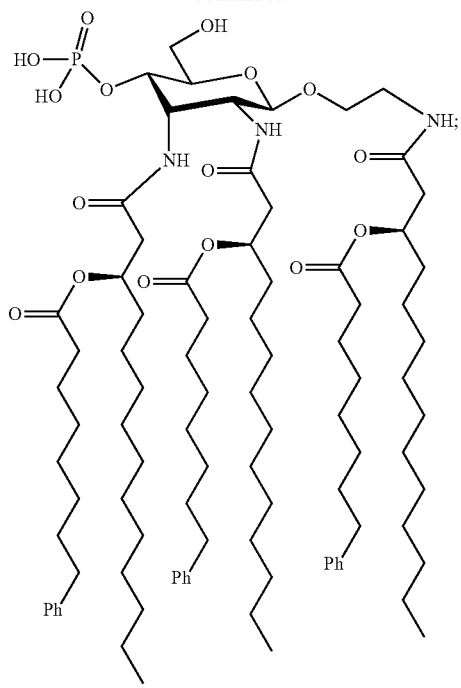

23
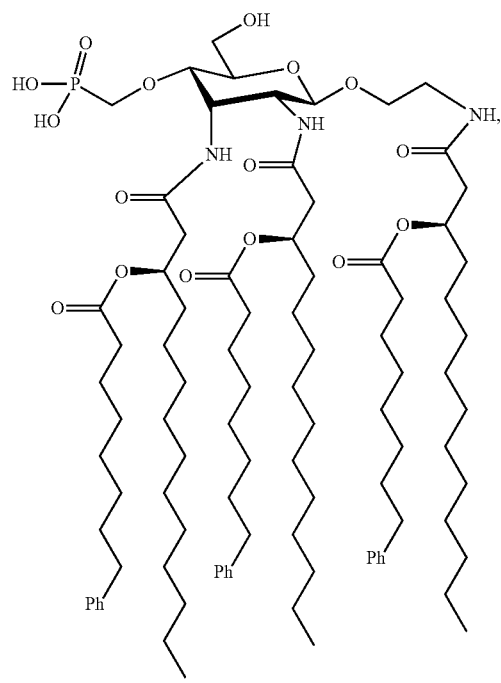
24
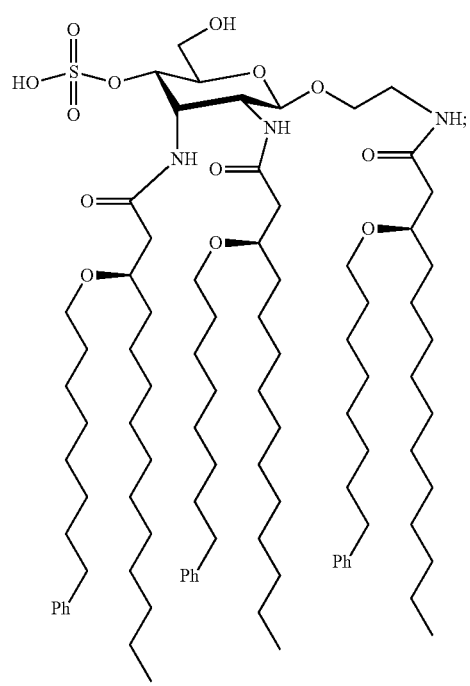
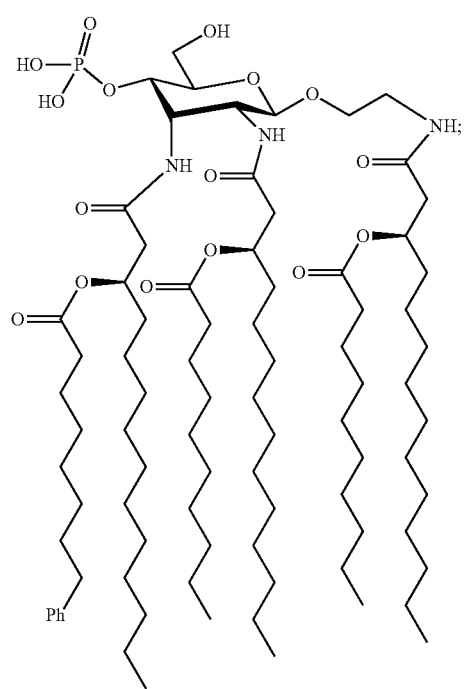
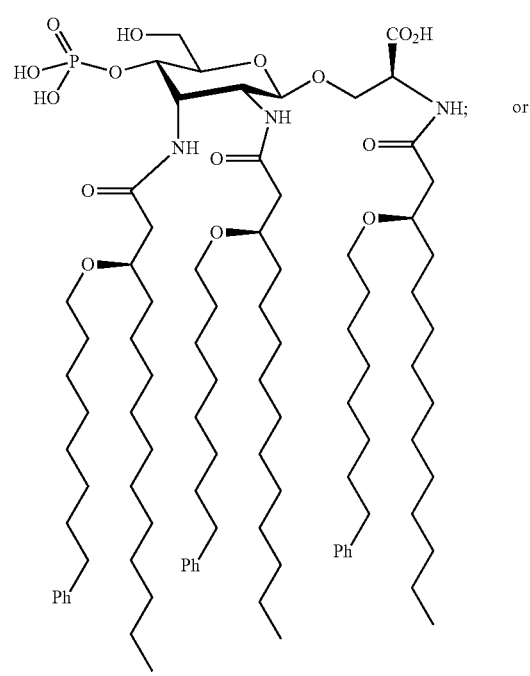
or

-continued

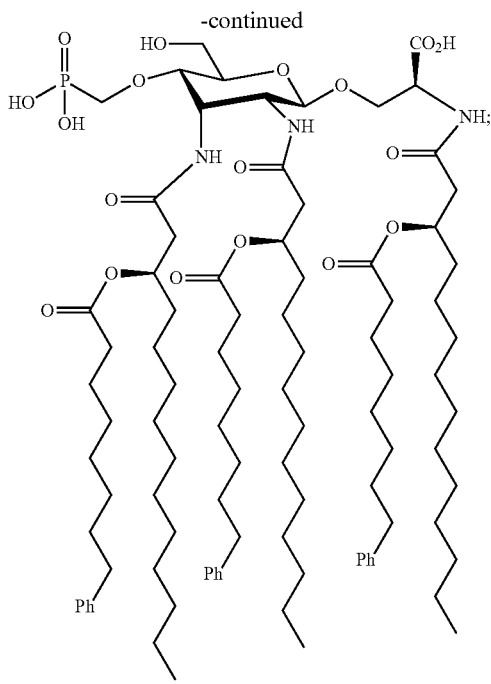

or a pharmaceutically acceptable salt thereof.

In another embodiment, the compounds include isotope-labelled forms. An isotope-labelled form of a compound is identical to the compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound by well-known methods include isotopes of hydrogen, carbon, nitrogen, oxygen, fluorine and chlorine, for example $^{2}H$, $^{3}H$, $^{13}C$, $^{14}C$, $^{15}N$, $^{18}O$, $^{17}O$, $^{18}F$ and $^{36}Cl$.

In some embodiments the compound of formula (I) is a TLR agonist (e.g., TLR4).

In some embodiments, the compound of formula (I) is a TLR antagonist (e.g., TLR4).

In some embodiments, the compound of formula (I) is a TLR modulator.

3. Uses and Methods

When a foreign antigen challenges the immune system it responds by launching a protective response that is characterized by the coordinated interaction of both the innate and acquired immune systems. These two interdependent systems fulfill two mutually exclusive requirements: speed (contributed by the innate system) and specificity (contributed by the adaptive system).

The innate immune system serves as the first line of defense against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent. The development of TLR modulators for therapeutic targeting of innate immunity has been reviewed (see Nature Medicine, 2007, 13, 552-559; Drug Discovery Today: Therapeutic Strategies, 2006, 3, 343-352 and Journal of Immunology, 2005, 174, 1259-1268).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by specificity and long lasting memory. However, it also involves the recruitment of elements of the innate immune system, including professional phagocytes (macrophages, neutrophils etc.) and granulocytes (basophils, eosinophils etc.) that engulf bacteria and even relatively large protozoal parasites. Once an adaptive immune response has matured, subsequent exposure to the pathogen results in its rapid elimination due to highly specific memory cells have been generated that are rapidly activated upon subsequent exposure to their cognate antigen.

In certain embodiments, the compounds and compositions provided herein elicit a cell mediated immune and/or a humoral immune response. In other embodiments, the immune response induces long lasting (e.g. neutralizing) antibodies and a cell mediated immunity that quickly responds upon exposure to the infectious agent.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response, a TH2 immune response and a TH17 response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 and IgE production.

A Th17 immune response may include one or more of an increase in one or more of the cytokines associated with a TH17 immune response (such as IL-17, IL-22, IL-23, TGF-beta and IL-6), or an increase in humoral immunity and memory B cells.

In certain embodiments, the immune response is one or more of a TH1 immune response, a TH2 response and a TH17 response. In other embodiments, the immune response provides for an enhanced TH1 response, TH2 response, and/or TH17 response. In some embodiments, the compounds or compositions disclosed herein may function as an adjuvant (e.g., in a vaccine).

In certain embodiments, the enhanced immune response is one or both of a systemic and a mucosal immune response. In other embodiments, the immune response provides for one or both of an enhanced systemic and an enhanced mucosal immune response. In certain embodiments, the mucosal immune response is a TH1, TH2, or TH17 immune response. In certain embodiments, the mucosal immune response includes an increase in the production of IgA.

In certain embodiments the immunogenic compositions provided herein are used as vaccines, wherein such compositions include an immunologically effective amount of one or more antigens.

Autoimmune diseases, are defined by (i) humoral or autoantibody response to a self-antigen (by way of example only, Graves' primary hyperthyroidism with antibodies to the TSH receptor), or (ii) cellular response wherein immune cells destroy nonimmune cells from which the self-antigen is derived (by way of example only, the thyrocyte (Hashimoto's thyroiditis) or pancreatic β-islet cell (Type 1 diabetes). Many autoimmune diseases are a combination of both phenomena, for instance, Hashimoto's and Type 1 diabetes also have autoantibodies, anti-thyroid peroxidase (TPO) or anti-glutamic acid decarboxylase (GAD)/Islet Cell. Autoimmune diseases often have an inflammatory component including, but not limited to, increases in adhesion molecules (by way of example only, vascular cell adhesion molecule-1 (VCAM-1), and altered leukocyte adhesion to the vasculature such as, by way of example only, colitis, systemic lupus, systemic sclerosis, and the vascular complications of diabetes.

Toll-like receptors (TLRs) are type-I transmembrane proteins characterized by an extracellular N-terminal leucine-rich repeat (LRR) domain, followed by a cysteine rich region, a transmembrane (TM) domain, and an intracellular (cytoplasmic) tail that contains a conserved region named the Toll/IL-1 receptor (TIR) domain. TLRs are pattern recognition receptors (PRR) that are expressed predominantly on immune cells including, but not limited to, dendritic cells, T lymphocytes, macrophages, monocytes and natural killer cells. The LRR domain is important for ligand binding and associated signaling and is a common feature of PRRs. The TIR domain is important in protein-protein interactions and is associated with innate immunity. The TIR domain also unites a larger IL-1 R/TLR superfamily that is composed of three subgroups. Members of the first group possess immunoglobin domains in their extracellular regions and include IL-1 and IL-18 receptors and accessory proteins as well as ST2. The second group encompasses the TLRs. The third group includes intracellular adaptor proteins important for signaling.

TLRs are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Adaptive (humoral or cell-mediated) immunity is associated with the TLR signal mechanism of innate immunity. Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1), T helper 2 (Th2), T helper 17 (Th17) or other T cell types. Th1 cells mainly promote cellular immunity, whereas Th2 cells mainly promote humoral immunity. Though primarily a host protective system, pathologic expression of the innate immunity signals emanating from the TLR pathway are implicated in initiating autoimmune-inflammatory diseases.

All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-α, interleukins, MIP-1 and MCP-1 which contribute to the killing and clearance of the pathogenic invasion. TLR spatial expression is coincident with the host's environmental interface. While only a few other Toll-like proteins have been cloned in *Drosophila*, the human TLR family is composed of at least 11 members, TLR1 through TLR11, that elicit overlapping yet distinct biological responses due to differences in cellular expression and signaling pathways they initiate. Each of the TLRs is expressed on a different subset of leukocytes and each of the TLRs is specific in its expression patterns and PAMP sensitivities and detects different subsets of pathogens allowing vigilant surveillance by the immune system.

TLRs are distributed throughout the cell. TLR1, TLR2, TLR3 and TLR4 are expressed on the cell surface, whereas, TLR3, TLR7, TLR8 and TLR9 are expressed in intracellular compartments such as endosomes. TLR3-, TLR7- or TLR9-mediated recognition of their ligands requires endosomal maturation and processing. When macrophages, monocytes, dendritic cells or nonimmune cells that become antigen presenting cells engulf bacteria by phagocytosis, the bacteria degrade and CpG DNA is release into phagosomes-lysosomes or in endosomes-lysosomes wherein they can interact with TLR9 that has been recruited from the endoplasmic reticulum upon non-specific uptake of CpG DNA. Furthermore, when viruses invade cells by receptor-mediated endocytosis, the viral contents are exposed to the cytoplasm by fusion of the viral membrane with the endosomal membrane. This results in exposure of TLR ligands such as dsRNA, ssRNA and CpG DNA to TLR9 in the phagosomal/lysosomal or endosomal/lysosomal compartments.

In the signaling pathways downstream of the TIR domain, a TIR domain-containing adaptor, MyD88 and/or TRIF, is essential for induction of cytokines such as TNF-α and IL-12 through all TLRs. Although TR domain-containing adaptor molecules are common to all TLRs, individual TLR signaling pathways are divergent and activation of specific TLRs leads to slightly different patterns of gene expression profiles. By way of example only, activation of TLR3 and TLR4 signaling pathways results in induction of type I interferons (IFNs), while activation of TLR2- and TLR5-mediated pathways do not. However, activation of TLR7, TLR8 and TLR9 signaling pathways also leads to induction of Type I IFNs, although this occurs through mechanisms distinct from TLR3/4-mediated induction.

Once engaged, TLRs initiate a signal transduction cascade leading to activation of NFκB or IRFs via the adapter proteins myeloid differentiation primary response gene 88 (MyD88) or TIR domain-containing adaptor molecule inducing interferon-β (TRIF). The MyD88-dependent pathway is analogous to signaling by the IL-1 receptors, and it is regarded that MyD88, harboring a C-terminal TIR domain and an N-terminal death domain, associates with the TIR domain of TLRs. Upon stimulation, MyD88 recruits IRAK-4 to TLRs through interaction of the death domains of both molecules, and facilitates RAK-4-mediated phosphorylation of RAK-1. Phosphorylation of IRAK-1 then leads to recruitment of TNF receptor associated factor 6 (TRAF6), leading to the activation of two distinct signaling pathways. One pathway leads to activation of AP-1 transcription factors through activation of MAP kinases. Another pathway activates the TAK1/TAB complex, which enhances activity of the IκB kinase (IKK) complex. Once activated, the IKK complex induces phosphorylation and subsequent degradation of the NFκB inhibitor IκB, which leads to nuclear translocation of transcription factor NFκB and the initiation of transcription of genes whose promoters contain NFκB binding sites, such as cytokines. The MyD88-dependent pathway plays a crucial role and is essential for inflammatory cytokine production through all TLRs.

TRIF-dependent signaling via TLRs requires sequential or simultaneous binding of the TIR domain-containing adaptor proteins, TRAM/TICAM-2 and TRIF/TICAM-1, to the TLR4-TIR domain. Signaling through the TRIF-dependent pathway induces lower and later, but more sustained activation of NF-κB through an alternative pathway involving receptor-interacting protein 1 (RIP1). TRIF-dependent signaling also causes activation and nuclear translocation of interferon regulatory factors (IRF)-3 and IRF-7, which drives transcription of IFNβ and its subsequent extracellular release. Autocrine or paracrine binding of IFN to the IFN-α/β receptor, in turn, activates the JAK/STAT pathway, leading to increased expression of IFNα and IFNβ, as well as IFN-inducible chemokines such as interferon-inducible protein-10 (IP-10), regulated on activation normal T expressed (RANTES) and macrophage chemotactic protein-1 (MCP-1). Monophosphoryl lipid A (MPLA) and CRX-547 (both are TLR4 ligands) have reduced MyD88 signaling activity, but similar TRIF signaling activity when compared to LPS. This TRIF-biased response could be responsible for the increased therapeutic index, reduced toxicity and sustained adjuvant activity.

Compounds and compositions provided herein may be useful for eliciting or enhancing or modifying or suppressing in a host at least one immune response (e.g., a TH1-type T lymphocyte response, a TH2-type T lymphocyte response, a TH17-type T lymphocyte response, a cytotoxic T lymphocyte (CTL) response, an antibody response, a cytokine response, a lymphokine response, a chemokine response, and an inflammatory response). In certain embodiments the immune response may comprise at least production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production one or a plurality of chemokines wherein the chemokine is selected from MIP-1α, MIP-1β, RANTES, IP-10, CCL4 and CCL5, and a lymphocyte response that is selected from a memory T cell response, a memory B cell response, an effector T cell response, a cytotoxic T cell response and an effector B cell response.

Cancer immunotherapy generally focuses on inducing innate or adaptive immune responses. Adaptive immune responses could consist of humoral immune responses, cellular immune responses, or both. Moreover, it is well established that induction of CD4+ T helper cells is necessary in order to secondarily induce either antibodies or cytotoxic CD8+ T cells. Antigens (e.g., polypeptide antigens) that are selective or ideally specific for cancer cells offer a powerful approach for inducing immune responses against cancer.

The compounds and compositions of the invention may be used to stimulate an immune response against cancer. Compounds and compositions of the invention may be used in treating, preventing, or reducing the susceptibility to cancer including, but not limited to, prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes. In certain embodiments, the compounds and compositions are useful as modulators of toll-like receptor activity, and are used in the treatment of neoplasias including, but not limited to, basal cell carcinoma, squamous cell carcinoma, actinic keratosis, melanoma, carcinomas, sarcomas, leukemias, renal cell carcinoma, Kaposi's sarcoma, myelogeous leukemia, chronic lymphocytic leukemia and multiple myeloma.

Compounds and compositions of the invention may also be useful in treating, preventing, or reducing the susceptibility to food allergy, allergic rhinitis, allergic asthma, allergic skin diseases, seasonal allergy and associated allergic conditions. Other allergies include allergic conjunctivitis, atopic dermatitis and psoriasis.

Compounds and compositions of the invention may also be useful in treating, preventing, or reducing the susceptibility to bacterial, fungal, and protozoal infections including, but not limited to, tuberculosis and *Mycobacterium avium*, leprosy; *Pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, cryptococcal meningitis.

Compounds and compositions of the invention may be used in treating, preventing, or reducing the susceptibility to viral diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, para-influenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

Compounds and compositions of the invention may be used in treating, preventing, or reducing the susceptibility to prion diseases or transmissible spongiform encephalopathies (TSEs), such as Creutzfeldt-Jakob Disease or chronic wasting, variant Creutzfeldt-Jakob Disease, Gerstmann-Straussler-Scheinker Syndrome, Fatal Familial Insomnia and Insomni, Kuru.

Compounds and compositions of the invention may be used in treating, preventing, or reducing the susceptibility to the progressive neurodegenerative disease (e.g., Alzheimer's).

Compounds and compositions of the invention may be used in treating or preventing or reducing the severity of epileptic seizures.

Compounds and compositions of the invention may be used in treating, preventing, or reducing the susceptibility to sepsis resulting from bacterial, viral or fungal infections including wound infections, pneumonia, abdominal infection. kidney infection or bloodstream infection (bacteremia). severity of sepsis through antagonizing LPS (endotoxin) activation of the TLR4 receptor system.

Compounds and compositions of the invention may be used in treating or preventing or reducing the susceptibility to ocular diseases such as macular degeneration, ocular hypertension, and ocular infection.

Compounds and compositions of the invention may be used in treating, preventing, or reducing the severity of ischemia reperfusion injuries whereby tissue damage is caused as the result of ischemic stroke, myocardial ischemic injury, acute kidney injury or other ischemic events when blood supply returns to tissue after a period through attenuation of ischemia or lack of oxygen resulting in release of inflammatory cytokines via the TLR4 receptor.

Compounds and compositions of the invention may be used for treating, preventing, or reducing the susceptibility to autoimmune diseases, which include diseases, conditions or disorders wherein a host's or subject's immune system detrimentally mediates an immune response that is directed against self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subject's cells and tissues) or epitopes (e.g., specific immunologically defined recognition structures such as those recognized by an antibody variable region complementarity determining region (CDR) or by a T cell receptor).

Autoimmune diseases are thus characterized by an abnormal immune response involving either cells or antibodies that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia.

4. Pharmaceutical Compositions and Administration

In another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In one embodiment, the pharmaceutical composition comprises a therapeutically effective amount of a compound of the present invention or a pharmaceutically acceptable salt thereof and one or more pharmaceutically acceptable carriers or vehicles.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracistemally, intradermally, intranasally, intravaginally, intraperitoneally, intramuscularly, intravenously, intratumorally, topically (as by powders, ointments, or drops), bucally, sublingually, as an oral or nasal spray, or the like, depending on the severity of the disease being treated.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Liquid dosage forms for oral or nasal administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, cement, putty, thin film, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or trans dermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In preferred embodiments, the compounds of the described invention can be formulated either as pharmaceutically acceptable salts or free acids. Compounds may be formulated with a pharmaceutically acceptable vehicle for injection, inhalation, ingestion or other suitable form of administration. A pharmaceutically acceptable vehicle is a medium, solution or matrix that does not interfere with the immunomodulatory activity of the compound and is not toxic to the patient and preferably lends significant physical and chemical stability to the API. Pharmaceutically acceptable vehicles include aqueous solution, liposomes, oil-in-water or water-in-oil emulsions, polymeric particles, block-copolymers, aqueous dispersions, microparticles, proteins solutions or biodegradable particles for timed release. For example, the vehicle may be a microsphere, nanoparticle or microparticle having a compound of this invention in the matrix of the particle or adsorbed on the surface. The vehicle may also be an aqueous solution, buffered solution or micellar dispersion containing monoethanol amine, triethylamine, triethanolamine, or other chemical that renders the formulation alkaline. The vehicle may be a suspension containing aluminum hydroxide, aluminum phosphate, calcium hydroxide, or calcium phosphate where the compound may be adsorbed to the metal surface. Vehicles may also include all solvents, buffers, dispersion media, vehicles, coatings, diluents, antibacterial and antifungal agents, mucoadhesives, mucopenetrants, absorption delaying agents, packing agents, suspensions, colloids, and the like. The use of such vehicles for APIs is well known to those skilled in the art. Except vehicles or agents which are incompatible with the API, their use in prophylactic or therapeutic compositions is considered.

In one embodiment compounds of the invention are formulated in 2% glycerol or 2% glycine as an isotonic nanodispersion with a pH in the range of 5 to 7.4. In another embodiment the compounds of the invention are formulated in the lipid bilayer of a liposome. These liposomes may also contain other compounds with immunomodulatory activity to achieve a co-formulation with the compounds of the invention. More generally the compounds of the invention may be encapsulated in a nano or microparticle, emulsion, or other suitable vehicle as described above and these may also contain other immunomodulatory compounds or excipients to enhance biological activity, improve stability or alter pharmacokinetics of the formulation in a favorable way.

Compounds described herein can be administered as a pharmaceutical composition comprising the compounds of interest in combination with one or more pharmaceutically acceptable carriers. The phrase "therapeutically effective amount" of the present compounds means sufficient amounts of the compounds to treat disorders, at a reasonable benefit/risk ratio applicable to any medical treatment. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer.

For adults, the doses are generally from about 0.00001 to about 100 mg/kg, desirably about 0.0001 to about 100 mg/kg body weight per day by inhalation, intranasal, intratumoral, sublingual, intradermal, or intrperitoneal, from about 0.00001 to about 100 mg/kg, desirably 0.0001 to 70 mg/kg, more desirably 0.5 to 10 mg/kg body weight per day by oral administration, and from about 0.00001 to about 50 mg/kg, desirably 0.0001 to 1 mg/kg body weight per day by intravenous administration.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

The additional pharmaceutical agents include antibiotics or antibacterial agents, anticancer agents, antiemetic agents, antifungal agents, anti-inflammatory agents, antiviral agents, immunomodulatory agents (e.g., immune checkpoint inhibitors), and other toll-like receptor modulators.

Anti-cancer agents (i.e., chemotherapeutics) include alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis proteins (1APs), intercalating agents, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Preferred anti-cancer chemotherapeutics: cyclophosphamide, doxo/duanorubicin, carboplatin-derivatives (e.g., cisplatin, oxaliplatin, carboplatin), HDAC inhibitors, gemcitabine, 5-fluorouracil, taxol-derivatives (e.g., taxol, paclitaxel, taxotere), mitomycin C, immune checkpoint inhibitors.

HDAC inhibitors include suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577.

Immune modulatory agents include interferons, antigens, tumor phagocytosis-inducing agents, and other immune-enhancing agents (e.g., immune checkpoint inhibitors).

Interferons include interferon alpha, interferon alpha-2a, interferon alpha-2b, interferon beta, interferon gamma-1a, ACTIMMUNE® (interferon gamma-1b), or interferon gamma-n1, combinations thereof and the like.

Tumor phagocytosis-inducing agents include anti-CD47 monoclonal antibodies (e.g., Hu5F9-G4, CC-90002, ZF1, AMMS4-G4, IBI188, SRF231), anti-SIRPα fusion proteins (e.g., TTI-621, TTI-622), anti-SIRPα monoclonal antibodies (e.g., OSE-172), anti-CD47/antitumor-associated antigen bispecific antibodies, and inhibitors of leukocyte immunoglobulin-like receptor B1 (LILRB1) binding to major histocompatibility complex class 1 β2-microglobulin (MHC class1 β2M).

Anti-CD47/antitumor-associated antigen bispecific antibodies include anti-CD47/CD19 bispecific antibodies (e.g., TG-1801), anti-CD47/mesothelin bispecific antibodies (e.g., NI-1801), anti-CD47/4-1BB bispecific antibodies (e.g., DSP107), anti-CD47/CD20 bispecific antibodies, anti-CD47/CD33 bispecific antibodies (e.g., HMBD004).

Immune checkpoint inhibitors include PD-1 inhibitors (e.g. nivolumab, pidilizumab, sintilimab), PD-L1 inhibitors (e.g. atezolizumab, avelumab, durvalumab, BMS-936559), CTLA4 inhibitors (e.g. ipilimumab, tremelimumab) or IDO inhibitors (e.g. indoximod, epacadostat).

Other immune modulating agents include ALFAFER-ONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanomavaccine, mitumomab, molgramostim, MYLOTARG™® (gemtuzumab ozogamicin). NEUPOGEN® (filgrastlm), OncoVAC-CL, OvaRex® (oregovomab), pemtumomab(Y-muHMFG1), PROVENGE®, sargaramostim, sizofilan, teceleukin, TheraCys®, ubenimex, VIRULIZIN, Z-1OO, WF-1O, PROLEUKIN® (aldesleukin), ZADAXIN® (thymalfasin), ZENAPAX® (daclizumab), ZEVALIN® (90Y-Ibritumomab tiuxetan) and the like including but not limited to STING (stimulator of interferon genes) and NOD (nucleotide-binding oligomerization domain-like receptors) Agonists.

In some embodiments, the pharmaceutical composition of the invention is a vaccine that comprises a compound of formula (I), or a pharmaceutically acceptable salt thereof, a pharmaceutically acceptable carrier, and optionally an antigen.

Antigens for use in the immunogenic compositions provided herein may be provided in an effective amount (e.g., an amount effective for use in therapeutic or prophylactic methods). For example, immunogenic compositions of the invention may be used to treat or prevent diseases or conditions such as infections and cancer. Exemplary antigens include, but are not limited to, tumor antigens and infectious disease antigens. Antigens for use in the immunogenic compositions provided herein are typically macromolecules (e.g., polypeptides, polysaccharides, polynucleotides) that are foreign to the host.

An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen may refer to a polypeptide antigen of interest. However, antigen, as used herein, may also refer to a recombinant construct which encodes a polypeptide antigen of interest (e.g., an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Bacterial Antigens.

Bacterial antigens suitable for use in immunogenic compositions provided herein include, but are not limited to, proteins, polysaccharides, lipopolysaccharides, polynucleotides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis*: Meningitidis antigens include, but are not limited to, proteins, saccharides (including a polysaccharide, oligosaccharide, lipooligosaccharide or lipopolysaccharide), or outer-membrane vesicles purified or derived from *N. meningitides* serogroup such as A, C, W135, Y, X and/or B. In certain embodiments *meningitides* protein antigens are be selected from adhesions, autotransporters, toxins, Fe acquisition proteins, and membrane associated proteins (preferably integral outer membrane protein).

*Streptococcus pneumoniae*: Streptococcus pneumoniae antigens include, but are not limited to, a saccharide (including a polysaccharide or an oligosaccharide) and/or protein from *Streptococcus pneumoniae*. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 1 SC serotype) is presented as an oligosaccharide. In certain embodiments saccharide antigens are selected from one or more of the following pneumococcal serotypes 1, 2, 3, 4, 5, 6A, 68, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, a 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. Nos. 6,699,703, 6,800,744, WO97/43303, WO97/37026, WO 02/079241, WO 02/34773, WO00/06737, WO 00/06738, WO 00/58475, WO 2003/082183, WO 00/37105, WO 02/22167, WO 02/22168, WO 2003/104272, WO 02/08426, WO 01/12219, WO99/53940, WO 01/81380, WO 2004/092209, WO00/76540, WO 2007/116322, LeMieux et al., Infect. Imm. (2006) 74:2453-2456, Hoskins et al., J. Bacterial. (2001) 183:5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Micro biol. Lett. (2001) 205(1):99-104, Brown et al., Infect. Immun. (2001) 69:6702-6706, Whalen et al., FEMS Immunol. Med. Microbial. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb 1), Streptococcal heme-associated protein (Shp), and Streptolysin S (SagA).

*Moraxella catarrhalis*: Moraxella antigens include, but are not limited to, antigens identified in WO02/18595 and WO 99/58562, outer membrane protein antigens (HMW-OMP), C-antigen, and/or LPS.

*Bordetella pertussis*: Pertussis antigens include, but are not limited to, pertussis holotoxin (PT) and filamentous haemagglutinin (FHA) from *B. pertussis*, optionally also combination with pertactin and/or agglutinogens 2 and 3.

*Burkholderia*: Burkholderia antigens include, but are not limited to *Burkholderia mallei, Burkholderia pseudomallei* and *Burkholderia cepacia*.

*Staphylococcus aureus*: Staph aureus antigens include, but are not limited to, a polysaccharide and/or protein from *S. aureus. S. aureus* polysaccharides include, but are not limited to, type 5 and type 8 capsular polysaccharides (CPS and CPS) optionally conjugated to nontoxic recombinant *Pseudomonas aeruginosa* exotoxinA, such as Staph VAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO2008/019162, WO 02/059148, WO 02/102829, WO03/011899, WO 2005/079315, WO 02/077183, WO99/27109, WO01/70955, WO00/12689, WO00/12131, WO 2006/032475, WO 2006/032472, WO 2006/032500, WO 2007/113222, WO 2007/113223, WO2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CPS, CPS, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen.*

*Clostridium botulinums* (Botulism): Botulism antigens include, but are not limited to, those derived from *C. botulinum.*

*Cornynebacterium diphtheriae* (Diphtheria): Diphtheria antigens include, but are not limited to, diphtheria toxin, preferably detoxified, such as CRM197. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen. *Pseudomonas aeruginosa: Pseudomonas* antigens include, but are not limited to, endotoxin A, Wzz protein, *P. aeruginosa* LPS, LPS isolated from PAOI (05 serotype), and/or Outer Membrane Proteins, including Outer Membrane Proteins F (OprF).

*Legionella pneumophila*. Bacterial antigens derived from *Legionella pneumophila.*

*Coxiella burnetii*. Bacterial antigens derived from *Coxiella burnetii.*

*Brucella*. Bacterial antigens derived from *Brucella*, including but not limited to, *B. abortus, B. canis, B. melitensis, B. neotomae, B. ovis, B. suis* and *B. pinnipediae.*

*Francisella*. Bacterial antigens derived from *Francisella*, including but not limited to, *F. novicida, F. philomiragia* and *F. tularensis.*

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae: Gonorrhoeae* antigens include, but are not limited to, Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis: Chlamydia trachomatis* antigens include, but are not limited to, antigens derived from serotypes A, B, Ba and C (agents of trachoma, a cause of blindness), serotypes L1, L2 & L3 (associated with Lymphogranuloma venereum), and serotypes, D-K. In certain embodiments, *chlamydia* trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori: H pylori* antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orfl364, NodT-family outer-membrane-factor-lipoprotein efflux transporter (orfl 767), gspK (orf3515), gspJ (orf3516), tonB-dependent siderophore receptor (orf3597), fimbrial protein (orf3613), upec-948, upec-1232, A chain precursor of the type-I fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F 1 capsular antigen, *Yersinia pestis* V antigen.

*Mycobacterium tuberculosis*: Tuberculosis antigens include, but are not limited to, lipoproteins, BCG antigens, a fusion protein of antigen 858 (Ag85B), M72, M72F, ID93, ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), and surface protein antigen (SPA).

*Listeria monocytogenes*: Bacterial antigens include, but are not limited to, those derived from *Listeria monocytogenes.*

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* 0139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, VIsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens, protein antigens or polynucleotide antigens of any of the above. Other bacterial antigens used in the immunogenic compositions provided herein include, but are not limited to, an outer membrane vesicle (OMV) preparation. Additionally, other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram negative bacteria, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

Viral Antigens.

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, Virus Like Particles (VLPs) and polynucleotide antigens which may be isolated, purified or derived from a virus or recombinantly synthesized. In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB 1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxyiridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Hepamavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VPO, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limited to, those derived from rhinovirus. In certain embodiments, the rhinovirus antigens are selected from one or more of the following Capsid proteins: VPO, VP1, VP2, VP2 and VP4. In certain embodiments, the antigens are formulated into virus-like particles (VLPs).

Hepamavirus: Viral antigens include, but are not limited to, those derived from a Hepamavirus, such as, by way of example only, Hepatitis A virus (HAY). Commercially available HAY vaccines include inactivated HAY vaccine.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tickborne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E/E2, NS345 polyprotein, NS 345-core polyprotein, core, and/or peptides from the non-structural regions. In certain embodiments, the Hepatitis C virus antigens include one or more of the following: HCV E1 and or E2 proteins, E1/E2 heterodimer complexes, core proteins and nonstructural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (orclades) A, B, C, D, F, G, H, J. K, O. In other embodiments, the antigens are derived from HIV-1 circulating recombinant forms (CRFs), including, but not limited to, A/B, A/E, A/G, A/G/1, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p5 5 gag and gp 140v delete). In certain embodiments, the HIV antigens are derived from one or more of the following strains: HIVIIIb, HIVSF2, HIVLAV, HIVLAI, HIVMN, HIV-1CM235, HIV-1US4, HIV-I SF 162, HIV-1 TVI, HIV-1MJ4. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or $\sigma 1s$. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B 19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus Viral antigens include, but are not limited to, those derived from a Human Herpesvirus, such as, by way of example only, Herpes Simplex Viruses (HSY), Varicella-zoster virus (VZV), EpsteinBarr virus (EBY), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSY antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, 1E1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, USB, US9, US10, US11, US12, US13, US14, US15, US16, US17, US18, US19, US20, US21, US29, US30 and US34A. CMV antigens may also be fusions of one or more CMV proteins, such as, by way of example only, pp 65/IE1 (Reap et al., Vaccine (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Fungal Antigens.

Fungal antigens for use in the immunogenic compositions provided herein include, but are not limited to, those derived from one or more of the fungi set forth below.

Fungal antigens are derived from Dermatophytres, including: *Epidermophyton jloccusum, Microsporum audouini, Microsporum can is, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme*; and Fungal pathogens are derived from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less connnon are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Plant Antigens/Pathogens.

Plant antigens/pathogens for use in the immunogenic compositions provided herein include, but are not limited to, those derived from *Ricinus communis*.

Cancer/Tumor Antigens.

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA. In certain embodiments, the tumor antigen is a whole, live or dead or permeabilized cancer cell.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NYESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1 701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolaseA (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanomamelanocyte differentiation antigens such as MART-1/Melan A, gp 100, MC1 R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSHP1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/MeI-40, H-Ras, E2A-PRL, H4-RET, IGH-IGK, MYL-RAR, Epstein Barr virus antigens, EBNA, human papillomavirus (HPV) antigens, including E6 and E7, hepatitis Band C virus antigens, human T-cell lymphotropic virus antigens, TSP-180, p185erbB2, p180erbB-3, c-met, nm-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Additionally, bacterial and viral antigens are used in conjunction with the immunogenic compositions provided herein for the treatment of cancer. In certain embodiments, the, carrier proteins, such as CRM197, tetanus toxoid, or *Salmonella typhimurium* antigen are used in conjunction/conjugation with compounds provided herein for treatment of cancer. The cancer antigen combination therapies will show increased efficacy and bioavailability as compared with existing therapies.

In certain embodiments, the immunogenic compositions containing at least one compound of Formula (I) include capsular saccharides from at least two of serogroups A, C, W135 and Y of *Neisseria meningitides*. In other embodiments, such vaccines further comprise an antigen from one or more of the following: (a) serogroup B *N. meningitidis*; (b) *Haemophilus influenzae* type B; and/or (c) *Streptococcus pneumoniae*.

In certain embodiments the immunogenic compositions containing at least one compound of Formula (I) include serogroups C, W135 & Y of *N. meningitides*. In certain embodiments the immunogenic compositions containing at least one compound of Formula (I) include serogroups A, C, W135 & Y of *N. meningitides*. In certain embodiments the immunogenic compositions containing at least one compound of Formula (I) include serogroups B, C, W135 & Y of *N. meningitides*. In certain embodiments the immunogenic compositions containing at least one compound of Formula (I) include serogroups A, B, C, W135 & Y of *N. meningitides*. In certain embodiments the immunogenic compositions containing at least one compound of Formula (I) include *H. influenzae* type B and serogroups C, W135 & Y of *N. meningitides*. In certain embodiments the immunogenic compositions containing at least one compound of Formula (I) include *H. influenzae* type B and serogroups A, C, W135 & Y of *N. meningitides*. In certain embodiments the immunogenic compositions containing at least one compound of Formula (I) include *H. influenzae* type B and serogroups B, C, W135 & Y of *N. meningitides*. In certain embodiments the immunogenic compositions containing at least one compound of Formula (I) include *H. influenzae* type B and serogroups A, B, C, W135 & Y of *N. meningitides*. In certain embodiments the immunogenic compositions containing at least one compound of Formula (I) include *S. pneumoniae* and serogroups C, W135 & Y of *N. meningitides*. In certain embodiments the immunogenic compositions containing at least one com-pound of Formula (I) include *S. pneumoniae* and serogroups A, C, W135 & Y of *N. meningitides*. In certain embodiments the immunogenic compositions containing at least one compound of Formula (I) include *S. pneumoniae* and serogroups B, C, W135 & Y of *N. meningitides*. In certain embodiments the immunogenic compositions containing at least one compound of Formula (I) include *S. pneumoniae* and serogroups A, B, C, W135 & Y of *N. meningitides*. In certain embodiments the immunogenic compositions containing at least one compound of Formula (I) include *H. influenzae* type B, *S. pneumoniae* and serogroups C, W135 & Y of *N. meningitides*. In certain embodiments the immunogenic compositions containing at least one compound of Formula (I) include *H. influenzae* type B, *S. pneumoniae* and serogroups A, C, W135 & Y of *N. meningitides*. In certain embodiments the immunogenic compositions containing at least one compound of Formula (I) include *H. influenzae* type B, *S. pneumoniae* and serogroups B, C, W135 & Y of *N. meningitides*. In certain embodiments the immunogenic compositions containing at least one compound of Formula (I) include *H. influenzae* type B, *S. pneumoniae* and serogroups A, B, C, W135 & Y of *N. meningitidis*.

In some embodiments, the antigen is an allergen. An allergen is a substance that can induce an allergic or asthmatic response in a susceptible subject. Allergens include pollens, insect venoms, animal dander, dust, fungal spores, foods (e.g. peanut, milk, eggs) and drugs (e.g., penicillin).

Autoantigens include any antigen of host origin, but they specifically include antigens characteristic of an autoimmune disease or condition. Autoantigens characteristic of an autoimmune disease or condition can be associated with, but not necessarily established as causative of, an autoimmune disorder. Specific examples of autoantigens characteristic of an autoimmune disease or condition include but are not limited to insulin, thyroglobulin, glomerular basement membrane, acetylcholine receptor, DNA, and myelin basic protein.

The disclosed compounds may be included in kits comprising the compound, or a pharmaceutically acceptable salt, a pharmaceutical composition, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The kits may contain one or more containers containing an additional therapeutic agent, including but not limited to those listed above. In certain embodiments, the kits may contain one or more containers containing an antigen(s), as described herein. In some embodiments the kits may be provided in the form of a vaccine composition as described herein, and optionally includes a syringe for injecting a subject with the vaccine composition.

5. Chemical Synthesis

Compounds of the invention may be prepared as illustrated in the following schemes and examples.

Abbreviations

Bn benzyl
Calcd calculated
Cbz benzyloxycarbonyl
DIAD diisopropyl azodicarboxylate
DPPA diphenylphosphoryl azide
EDC 1-(3-dimethylaminopropyl)-3-ethylcarbodiimide methiodide
Et ethyl
ESI-TOF electrospray ionization time-of-flight
FA fatty acid
HRMS high resolution mass spectrometry
Me methyl
Ph phenyl
ppm parts per million
psig pounds per square inch
pyr pyridine
Tf triflate
TFA trifluoroacetic acid Schemes 1-5 illustrate methods of preparing common intermediates and compounds of formula (I). Although the schemes illustrate certain variable definitions for intermediates and final compounds (e.g., $R^1$, $R^5$, $R^6$), the person skilled in the art will recognize that the synthetic methods may likewise be applied to compounds with other variable definitions. For example, other intermediates that supply the $R^1$ fragment (e.g., HO–(CH)$_k$–[pyrrolidine-N-Cbz]–)$_q$ )

may likewise be employed in the following schemes.

Scheme 1 illustrates a method of preparing a common advanced intermediate 2.
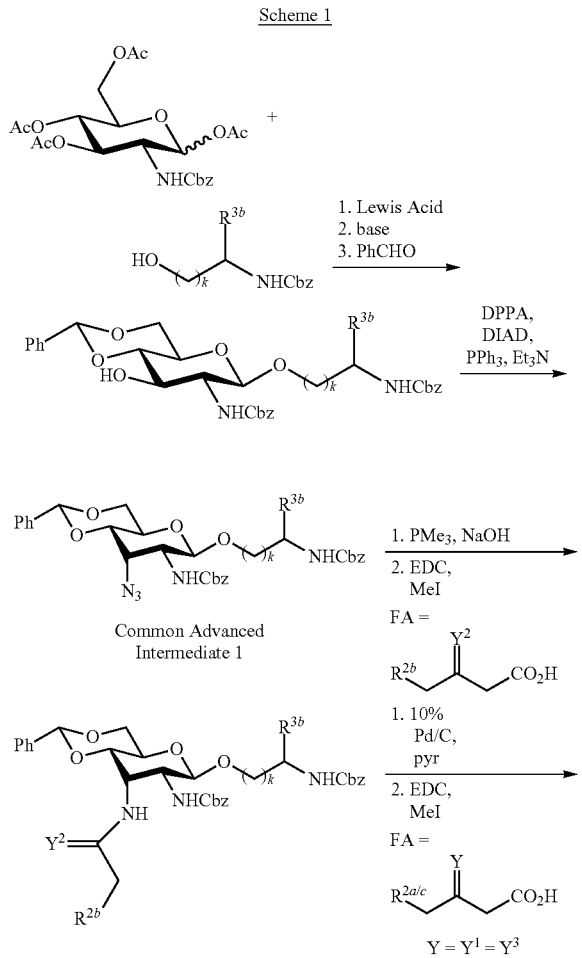
Scheme 2 illustrates an alternate method of preparing a common advanced intermediate 2 from common intermediate 1.
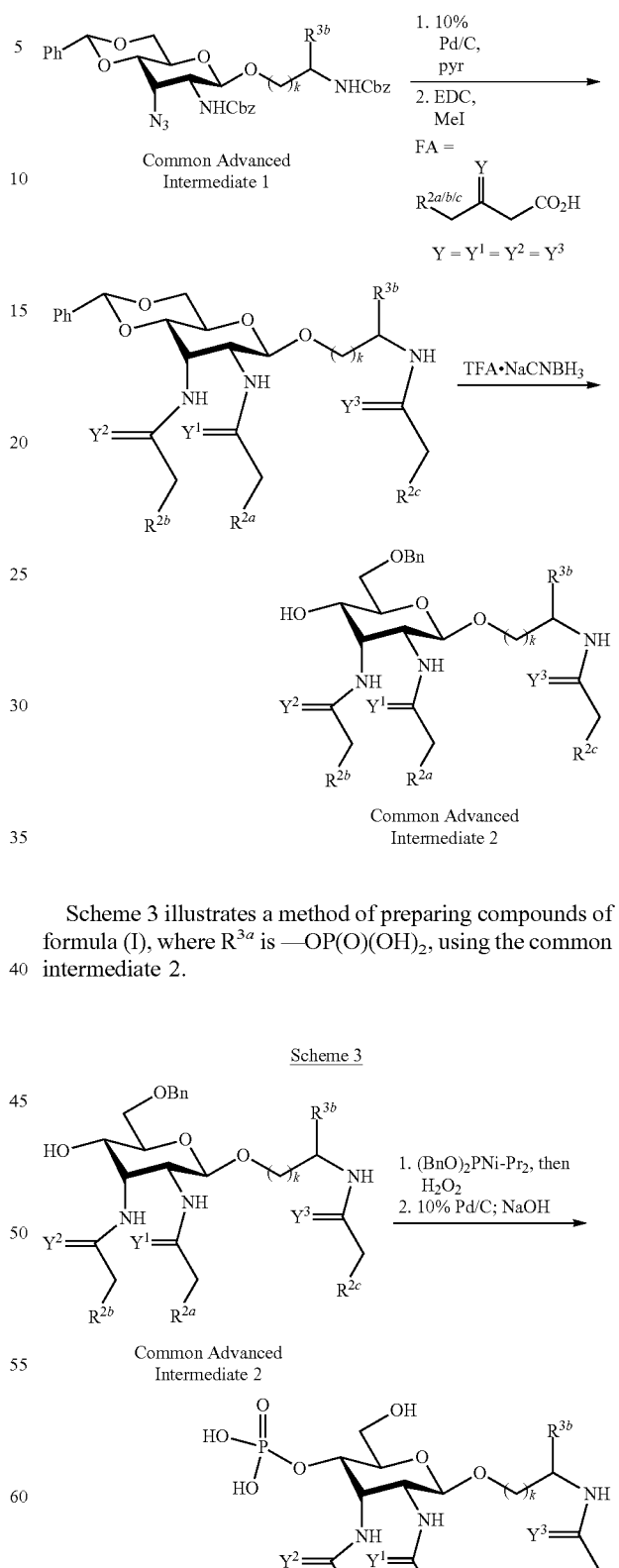
Scheme 3 illustrates a method of preparing compounds of formula (I), where $R^{3a}$ is —OP(O)(OH)$_2$, using the common intermediate 2.
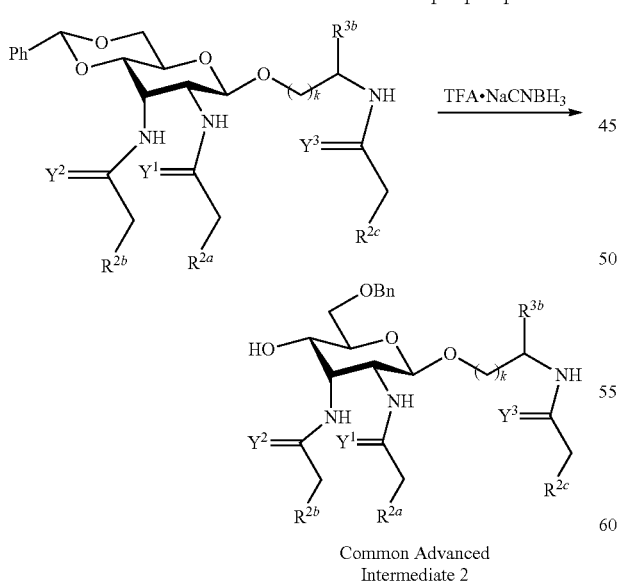

Scheme 4 illustrates a method of preparing compounds of formula (I), where $R^{3a}$ is —OSO$_3$H, using the common intermediate 2.

EXAMPLE 1

Preparation of 2-[(R)-3-decanoyloxytetradecanoylamino]ethyl 2,3-di-[(R)-3-decanoyloxytetradecanoylamino]-2,3-dideoxy-4-O-phosphono-β-D-allopyranoside (Compound 1)

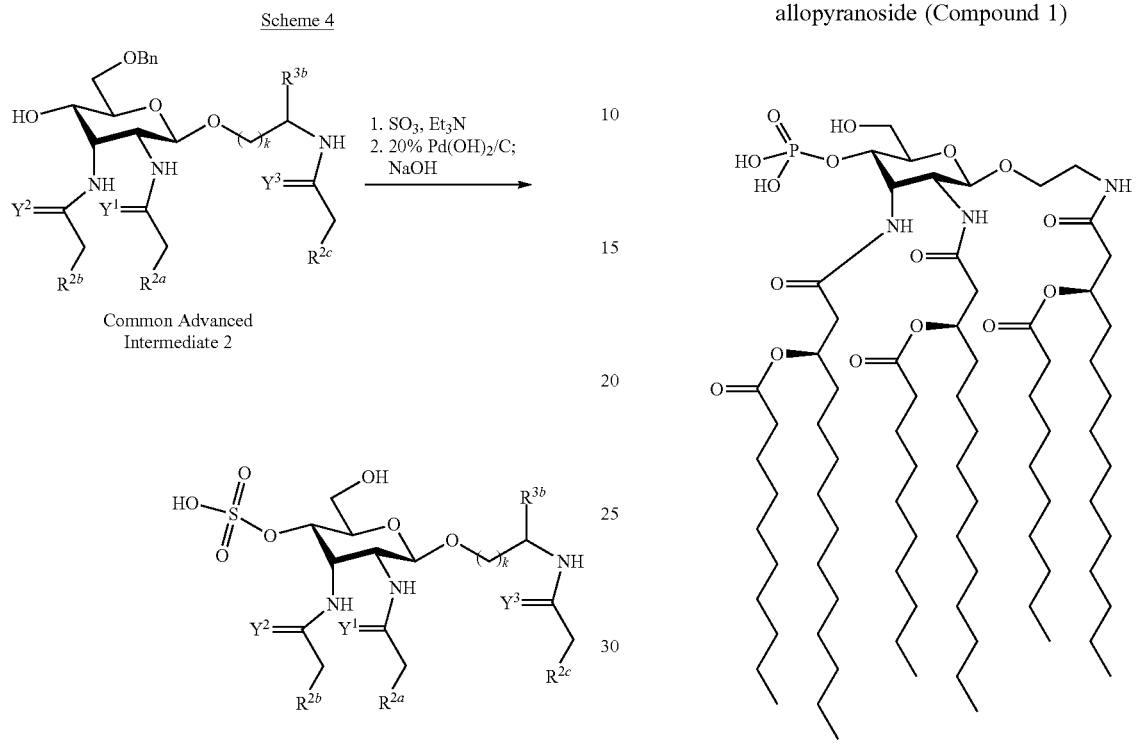

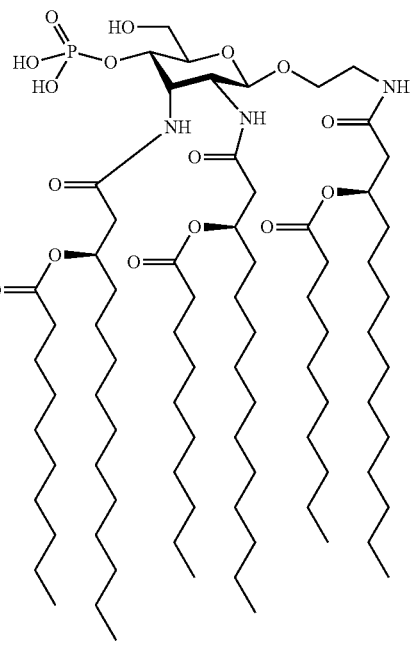

Scheme 5 illustrates a method of preparing compounds of formula (I), where $R^3$ is —OCH$_2$P(O)(OH)$_2$, using the common intermediate 2.

Example 1 utilizes a process as shown in Scheme A.

EXAMPLE 1A

A solution of 1,3,4,6-tetra-O-acetyl-2-amino-2-deoxy-β-D-glucopyranose hydrochloride (76.47 g, 0.23 mol) in methylene chloride (350 mL) and H$_2$O (350 mL) was treated with sodium bicarbonate (149.94 g, 1.79 mol) added in portions slowly. Benzyl chloroformate (79.17 g, 0.46 mol) was added in portions to control gas evolution and the reaction was stirred vigorously for 2.5 hours. The layers were separated and the aqueous layer was extracted with methylene chloride (100 mL). The combined organic layers were washed with saturated aqueous sodium chloride, dried over anhydrous sodium sulfate, filtered and concentrated to approximately 100 mL. Methyl-t-butyl ether (200 mL) was added and the resulting mixture was stirred and cooled to 0° C. and the precipitate was collected by filtration, washed with cold methyl-t-butyl ether and dried in a vacuum oven to give 88.89 g (81%) of 1,3,4,6-tetra-O-acetyl-2-(benzyloxycarbonylamino) 2-deoxy-β-D-glucopyranoside.

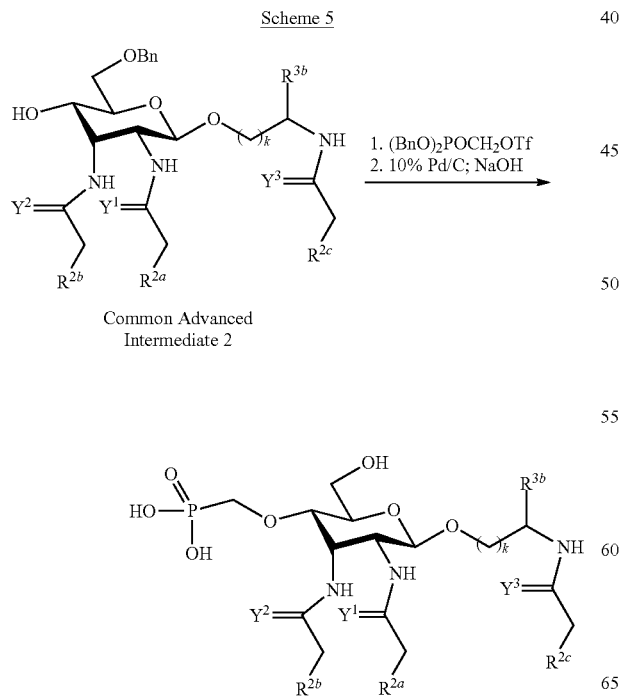

EXAMPLE 1B

A solution of the compound prepared in Example 1A above (10 g, 20.8 mmol) and benzyl N-(2-hydroxyethyl) carbamate (4.48 g, 22.9 mmol) in anhydrous methylene chloride (80 mL), cooled to −15° C., was treated dropwise with trimethylsilyl triflate (0.37 mL, 2.08 mmol). The reaction mixture was allowed to warm to room temperature over 5.5 hours. The reaction was quenched with saturated aqueous sodium bicarbonate (40 mL) and the layers were separated. The aqueous layer was extracted with methylene chloride (2×20 mL) and the combined organic layers were dried over anhydrous sodium sulfate, filtered and concentrated in vacuo. The crude product obtained was crystallized from methylene chloride/heptane to give 10.4 g (81%) of 2-(benzyloxycarbonylamino)ethyl 3,4,6-tri-O-acetyl-2-benzyloxycarbonylamino-2-deoxy-β-D-glucopyranoside as a white solid.

EXAMPLE 1C

A solution of the compound prepared in Example 1B above (10 g, 16.3 mmol) in methanol (160 mL) was treated with ammonium hydroxide (20 equivalents) for 2 hours at room temperature. The reaction mixture was concentrated and dried under high vacuum overnight to give 8 g (100%) of 2-(benzyloxycarbonylamino)ethyl 2-benzyloxycarbonylamino-2-deoxy-β-D-glucopyranoside as a white solid, which was used without further purification.

EXAMPLE 1D

A solution of the compound prepared in Example 1C above (8 g, 16.3 mmol) in acetonitrile (180 mL) was treated with benzaldehyde dimethyl acetal (4.9 mL, 32.6 mmol) and camphorsulfonic acid (1.9 g, 8.2 mmol). The reaction was stirred for 3 hours, neutralized with saturated aqueous sodium bicarbonate, filtered and concentrated in vacuo. The crude product was crystallized from ethyl acetate/heptane to give 7.1 g (75%) of 2-(benzyloxycarbonylamino)ethyl 4,6-O-benzylidene-2-deoxy-2-benzyloxycarbonylamino-2-deoxy-β-D-glucopyranoside as a white solid.

EXAMPLE 1E

A solution of the compound prepared in Example 1D above (1.5 g, 2.59 mmol) in anhydrous tetrahydrofuran (40 mL) was treated with triethylamine (0.54 mL, 3.89 mmol) and triphenylphosphine (1.09 g, 4.14 mmol). The reaction mixture was cooled to 0° C. and diisopropyl azodicarboxylate (0.82 mL, 4.14 mmol) was added. After 45 minutes at 0° C., diphenylphosphoryl azide (0.89 mL, 4.14 mmol) was added. The reaction was allowed to gradually warm up to room temperature and stirring continued for 18 hours. The reaction mixture was concentrated in vacuo and the residue chromatographed on silica gel (gradient elution, 20→70% ethyl acetate/heptane) affording 1.16 g (74%) of 2-(benzyloxycarbonylamino)ethyl 3-azido-4,6-O-benzylidene-2-benzyloxycarbonylamino-2,3-dideoxy-β-D-allopyranoside as a white solid.

EXAMPLE 1F

A solution of the compound prepared in Example 1E above (2.95 g, 4.89 mmol) in anhydrous tetrahydrofuran (100 mL) was treated with a solution of 0.1 N sodium hydroxide (9.8 mL, 0.98 mmol) and a solution of 1.0 M of trimethylphosphine in tetrahydrofuran (7.8 mL, 7.82 mmol). The reaction stirred at room temperature for 18 hours. The reaction mixture was concentrated in vacuo. The residue was chromatographed on silica gel (gradient elution, 30→100% ethyl acetate/heptane then 0→10% methanol/chloroform) affording 2.37 g (84%) of 2-(benzyloxycarbonylamino)ethyl 3-amino-4,6-O-benzylidene-2-benzyloxycarbonylamino-2,3-dideoxy-β-D-allopyranoside as a white solid.

EXAMPLE 1G

A solution of the compound prepared in Example 1F above (0.5 g, 0.87 mmol) in anhydrous methylene chloride (10 mL) was acylated with (R)-3-decanoyloxytetradecanoic acid (414 mg, 1.04 mmol) and 1-(3-dimethylaminopropyl)-3-ethylcarbodiimide methiodide (310 mg, 1.04 mmol) at room temperature for 2 hours. The reaction mixture was quenched with saturated aqueous sodium bicarbonate (5 mL) and the layers separated. The aqueous layer was extracted with chloroform (2×5 mL) and the combined organic layers were washed with water (5 mL), dried over anhydrous sodium sulfate and concentrated in vacuo. Chromatography on silica gel (gradient elution, 10→60% ethyl acetate/heptane) afforded 748 mg (90%) of 2-(benzyloxycarbonylamino)ethyl 4,6-O-benzylidene-2-benzyloxycarbonylamino-3-[(R)-3-decanoyloxytetradecanoylamino]-2,3-dideoxy-β-D-allopyranoside as a colorless oil.

EXAMPLE 1H

A solution of the compound prepared in Example 1G above (745 mg, 0.78 mmol) in anhydrous tetrahydrofuran (20 mL) was hydrogenated with 10% palladium on carbon (220 mg) using a Parr hydrogenator at room temperature and 50 psig for 24 hours. The reaction mixture was filtered through Celite and the filtrate concentrated in vacuo. The resulting oil dissolved in methylene chloride (10 mL) was acylated with (R)-3-decanoyloxytetradecanoic acid (680 mg, 1.71 mmol) and 1-(3-dimethylaminopropyl)-3-ethylcarbodiimide methiodide (510 mg, 1.71 mmol) at room temperature for 2 hours. The reaction mixture was quenched with saturated aqueous sodium bicarbonate (10 mL) and the layers separated. The aqueous layer was extracted with methylene chloride (2×10 mL) and the combined organic layers washed with water (10 mL), dried over anhydrous sodium sulfate and concentrated in vacuo. Chromatography on silica gel (gradient elution, 20→80% ethyl acetate/heptane) afforded 732 mg (65%) of 2-[(R)-3-decanoyloxytetradecanoylamino]ethyl 4,6-O-benzylidene-2,3-di-[(R)-3-decanoyloxytetradecanoylamino]-2,3-dideoxy-β-D-allopyranoside as a glassy solid.

EXAMPLE 1I

A solution of the compound prepared in Example 1H above (400 mg, 0.282 mmol) in anhydrous methylene chloride (20 mL) cooled to 0° C. was treated with sodium cyanoborohydride (42 mg, 0.655 mmol) followed by the addition of trifluoroacetic acid (0.06 mL, 0.786 mmol). The reaction mixture gradually warmed up to room temperature and continued to stir for 3 hours. The reaction was quenched with methanol (2 mL), concentrated in vacuo then reconstituted in methylene chloride and washed with a saturated solution of sodium bicarbonate. The layers separated and the aqueous layer was extracted with methylene chloride (2×10 mL) and the combined organic layers dried over anhydrous sodium sulfate and concentrated in vacuo. Chromatography on silica gel (gradient elution, 10→95% ethyl acetate/heptane) afforded 380 mg (93%) of 2-[(R)-3-decanoyloxytetradecanoylamino]ethyl 6-O-benzyl-2,3-di-[(R)-3-decanoyloxytetradecanoylamino]-2,3-dideoxy-β-D-allopyranoside as a colorless oil.

EXAMPLE 1J

A solution of the compound prepared in Example 1I above (150 mg, 0.103 mmol) in anhydrous methylene chloride (10 mL) was phosphorylated with dibenzyl diisopropylphosphoramidite (0.049 mL, 0.144 mmol) and 4,5-dicyanoimidazole (17 mg, 0.144) and stirred at room temperature for 2 hours. The reaction mixture was cooled to 0° C. and treated with hydrogen peroxide (2 mL) for 30 minutes. The reaction mixture was quenched by addition of saturated aqueous sodium bicarbonate (5 mL) and stirred at room temperature for 15 minutes. The aqueous layer was extracted with methylene chloride (3×5 mL) and the combined organic layers washed with water (5 mL), dried over anhydrous sodium sulfate, and concentrated in vacuo. Chromatography on silica gel (gradient elution, 10→70% ethyl acetate/heptane) afforded 112 mg (64%) of 2-[(R)-3-decanoyloxytetradecanoylamino]ethyl 6-O-benzyl-4-O-dibenzylphosphino-2,3-di-[(R)-3-decanoyloxytetradecanoylamino]-2,3-dideoxy-β-D-allopyranoside as a foamy solid.

EXAMPLE 1K

A solution of the compound prepared in Example 1J above (110 mg, 0.064 mmol) in anhydrous tetrahydrofuran (3 mL) was hydrogenated in the presence of 10% palladium on carbon (30 mg) using a Parr hydrogenator at room temperature and 50 psig for 36 hours. The reaction mixture was filtered through Celite and the filtrate was concentrated under vacuum. Chromatography on silica gel with chloroform-methanol-water-triethylamine (gradient elution; 90:10:0.5:0.5→70:30:2:0.5). The fractions containing purified product were combined, concentrated in vacuo, then re-dissolved in cold 2:1 chloroform-methanol (14 mL) and washed with cold 0.1 N aqueous hydrochloride (5.52 mL). The lower organic layer was dried over anhydrous sodium sulfate and concentrated in vacuo affording 64 mg (70%) of 2-[(R)-3-decanoyloxytetradecanoylamino]ethyl 2,3-di-[(R)-3-decanoyloxytetradecanoylamino]-2,3-dideoxy-4-O-phosphono-β-D-allopyranoside as a glassy solid: $^1$H NMR (CDCl$_3$/CD$_3$OD): δ (ppm) 5.21 (br s, 3H), 4.60-4.50 (m, 3H), 4.08-4.01 (m, 2H), 3.85-3.80 (m, 2H), 3.71-3.68 (m, 1H), 3.52-3.31 (m, 4H), 2.64-2.18 (m, 12H), 1.59 (br s, 12H), 1.40-1.15 (m, 90H), 0.88 (t, J=6.4 Hz, 18H); HRMS (ESI-TOF) m/z: Calcd for C$_{80}$H$_{152}$N$_3$O$_{16}$P [M-H]$^-$ 1441.0832, found 1441.0755.

EXAMPLE 2

Preparation of 2-[(R)-3-decanoyloxytetradecanoylamino]ethyl 2,3-di-[(R)-3-decanoyloxytetradecanoylamino]-2,3-dideoxy-4-O-sulfoxy-β-D-allopyranoside (Compound 2)

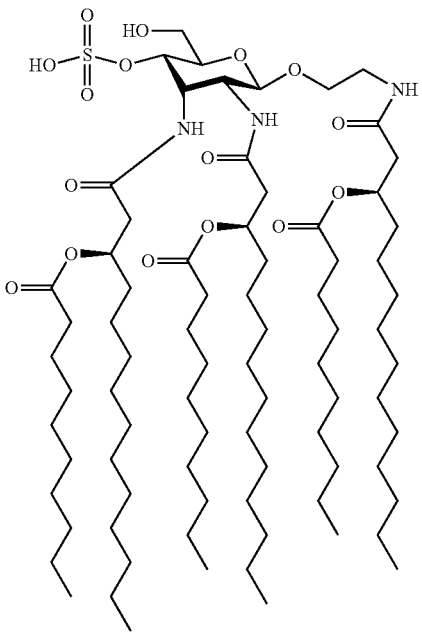

EXAMPLE 2A

A solution of the compound prepared in Example 1I—(9) (105 mg, 0.072 mmol) in anhydrous dimethylformamide (5 mL) was treated with sulfur trioxide triethylamine complex (78 mg, 0.43 mmol). The reaction was heated to 50° C. for 5 h. An additional amount of sulfur trioxide triethylamine complex (100 mg, 0.55 mmol) was added and the reaction stirred at 50° C. for 18 h. The reaction mixture was concentrated in vacuo. Chromatography on Cis column (gradient elution, 5→20% methylene chloride+1% triethylamine/methanol) afforded 90 mg (82%) of 2-[(R)-3-decanoyloxytetradecanoylamino]ethyl 6-O-benzyl-2,3-di-[(R)-3-decanoyloxytetradecanoylamino]-2,3-dideoxy-4-O-sulfoxy-β-D-allopyranoside triethylammonium salt as a white salt.

EXAMPLE 2B

A solution of the compound prepared in Example 2A above (70 mg, 0.045 mmol) in a mixture of 2:1 anhydrous tetrahydrofuran: methanol (5 mL) was hydrogenated in the presence of 20% palladium hydroxide on carbon (30 mg) and triethylamine (0.034 mL, 0.00024 mmol) using a Parr hydrogenator at room temperature and 50 psig pressure for 18 hours. The reaction mixture was filtered through Celite and the filtrate was concentrated under vacuum. Chromatography on Cis silica column (gradient elution, 5→20% methylene chloride+1% triethylamine/methanol), the purified material was dissolved in cold 2:1 chloroform-methanol (8 mL) and washed with cold 0.1 N aqueous hydrochloride (1.6 mL). The lower organic layer was dried over anhydrous sodium sulfate and concentrated in vacuo. The residue was salted with (1-2 equiv.) triethylamine to give 28 mg (43%) of 2-[(R)-3-decanoyloxytetradecanoylamino]ethyl 2,3-di-[(R)-3-decanoyloxytetradecanoylamino]-2,3-dideoxy-4-O-sulfoxy-β-D-allopyranoside triethylammonium salt as a glassy solid: $^1$H NMR (CDCl$_3$/CD$_3$OD): δ (ppm) 7.84 (t, J=5.5 Hz, 1H), 7.55 (d, J=8.0 Hz, 1H), 7.22 (d, J=9.0 Hz, 1H), 5.27-5.23 (m, 3H), 4.65 (br s, 1H), 4.59-4.55 (m, 2H), 4.26-4.21 (m, 1H), 4.19-4.15 (m, 1H), 3.85-3.79 (m, 2H), 3.73-3.70 (m, 1H), 3.51-3.43 (m, 2H), 3.18 (q, J=7.5 Hz, 7H, CH$_2$ of triethylamine (~1.2 equiv.)), 2.62-2.19 (m, 12), 1.64-1.52 (m, 12H), 1.37-1.26 (m, 100H, including 10, CH$_3$ of triethylamine), 0.88 (t, J=7.0 Hz, 18H); HRMS (ESI-TOF) m/z: Calcd for C$_{80}$H$_{151}$N$_3$O$_{16}$S [M-H]$^-$ 1441.0737, found 1441.0714.

EXAMPLE 3

Preparation of N—[(R)-3-Decanoyloxytetradecanoyl]-O-[2,3-di-[(R)-3-decanoyloxytetradecanoylamino]-2,3-dideoxy-4-O-phosphono-β-D-allopyranosyl]-L-serine methyl ester (Compound 3)

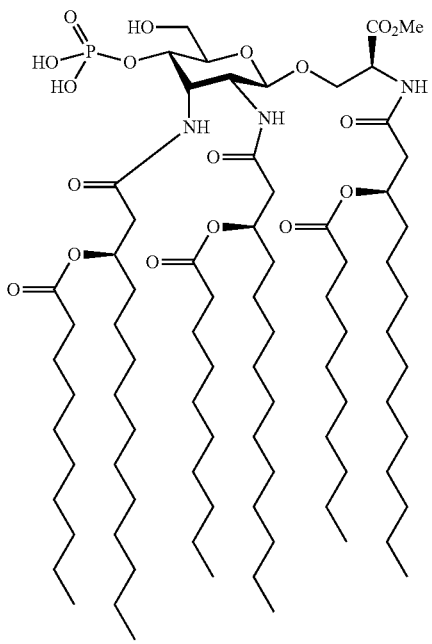

EXAMPLE 3A

A suspended solution of L-serine methyl ester hydrochloride (11.4 g, 73.3 mmol) in 1:1 of methylene chloride: water (160 mL) was treated with sodium bicarbonate (74 g, 879 mmol), followed by dropwise addition of benzyl chloroformate (12.4 mL, 87.9 mmol). The reaction was stirred vigorously for 18 hours. The layers were separated, the aqueous layer was extracted with methylene chloride (2×30 mL) and the combined organic layers dried over anhydrous sodium sulfate and concentrated in vacuo. Chromatography on silica gel (gradient elution, 10→50% ethyl acetate/heptane) afforded 16.8 g (91%) of N-benzyloxycarbonyl-L-serine methyl ester as a colorless oil.

EXAMPLE 3B

In an analogous manner as described in Example 1B, a solution of the compound prepared in Example 3A above (16.8 g, 66.3 mmol) and the compound prepared in Example 1A (38 g, 73.0 mmol) were reacted in the presence of boron trifluoride etherate (11.3 mL, 79.6 mmol) to afford 45.5 g (quant.) of N-benzyloxycarbonyl-O-(3,4,6-tri-O-acetyl-2-benzyloxycarbonylamino-2-deoxy-β-D-glucopyranosyl)-L-serine-methyl ester as a viscous oil, which was used without further purification.

EXAMPLE 3C

In an analogous manner as described in Example 1C, a solution of the compound prepared in Example 3B (15 g, 22.2 mmol) was deacylated in the presence of a 6-10% solution of magnesium methoxide in methanol (6 mL, 44.5 mmol) affording 4.7 g (39%) of N-benzyloxycarbonyl-O-[2-benzyloxycarbonylamino)-2-deoxy-β-D-glucopyranosyl]-L-serine-methyl ester as a colorless oil.

EXAMPLE 3D

In an analogous manner as described in Example 1D, a solution of the compound prepared in Example 3C above (4.7 g, 8.57 mmol) in acetonitrile (20 mL) was protected using benzaldehyde dimethyl acetal (2.6 mL, 17.14 mmol) and camphorsulfonic acid (1.0 g, 4.28 mmol) to afford 4.08 g (75%) of N-benzyloxycarbonyl-O-[4,6-O-benzylidene-2-benzyloxycarbonylamino-2-deoxy-β-D-glucopyranosyl]-L-serine methyl ester as a white solid.

EXAMPLE 3E

In an analogous manner as described in Example 1E, a solution of the compound prepared in Example 3D (2.0 g, 3.14 mmol) underwent a Mitsunobu reaction with triethylamine (0.66 mL, 4.71 mmol), triphenylphosphine (1.32 g, 5.03 mmol) and diisopropyl azodicarboxylate (1.0 mL, 5.03 mmol) followed by the addition of diphenylphosphoryl azide (1.08 mL, 5.03 mmol) affording 1.37 g (66%) of N-benzyloxycarbonyl-O-[3-azido-4,6-O-benzylidene-2-benzyloxycarbonylamino-2,3-dideoxy-β-D-allopyranosyl]-L-serine-methyl ester as a white foamy solid.

EXAMPLE 3F

A solution of the compound prepared in Example 3E above (0.52 g, 0.79 mmol) in anhydrous tetrahydrofuran (10 mL) was hydrogenated with 10% palladium on carbon (100 mg) and (0.10 mL) pyridine using a Parr hydrogenator at room temperature and 50 psig for 36 hours. The reaction mixture was passed through a pad of Celite, concentrated in vacuo and azeotropically washed with toluene (2×10 mL) then concentrated in vacuo and kept under vacuum for 48 hours. The resulting foamy solid in anhydrous methylene chloride (10 mL) cooled to 0° C. was acylated with (R)-3-decanoyloxytetradecanoic acid (1.0 g, 2.50 mmol) and 1-(3-dimethylaminopropyl)-3-ethylcarbodiimide methiodide (0.74 g, 2.50 mmol). After stirring at room temperature for 2 hours, the reaction mixture was quenched with saturated aqueous sodium bicarbonate (10 mL) and the layers were separated. The aqueous layer was extracted with chloroform (2×10 mL) and the combined organic layers were washed with water (10 mL), dried over anhydrous sodium sulfate and concentrated in vacuo. Chromatography on silica gel (gradient elution, 20→60% ethyl acetate/heptane) afforded 230 mg (20%) of N—[(R)-3-decanoyloxytetradecanoyl]-O-[4,6-O-benzylidene-2,3-di-[(R)-3-decanoyloxytetradecanoylamino]-2,3-dideoxy-β-D-allopyranosyl]-L-serine methyl ester as a glassy solid.

EXAMPLE 3G

In an analogous manner as Example 1I, the compound prepared in Example 3F above (210 mg, 0.15 mmol) was reacted with sodium cyanoborohydride (46 mg, 0.73 mmol) and trifluoroacetic acid (0.066 mL, 0.87 mmol) to afford 200 mg (91%) of N—[(R)-3-decanoyloxytetradecanoyl]-O-[6-O-benzyl-2,3-di-[(R)-3-decanoyloxytetradecanoylamino]-2,3-dideoxy-β-D-allopyranosyl]-L-serine methyl ester as a colorless oil.

EXAMPLE 3H

In an analogous manner as Example 1J, a solution of the compound prepared in Example 3G above (200 mg, 0.13 mmol) was phosphorylated with dibenzyl diisopropylphosphoramidite ((, 0.079 mL, 0.234 mmol), 4,5-dicyanoimidazole (27 mg, 0.234 mmol) and hydrogen peroxide (1 mL) affording 45 mg (19%) of N—[(R)-3-decanoyloxytetradecanoyl]-O-[6-O-benzyl-4-O-dibenzylphosphino-2,3-di-[(R)-3-decanoyloxytetradecanoylamino]-2,3-dideoxy-β-D-allopyranosyl]-L-serine methyl ester as a foamy solid.

EXAMPLE 3I

In an analogous manner as Example 1K, a solution of the compound prepared in Example 3H above (45 mg, 0.025 mmol) was hydrogenated in the presence of 10% palladium on carbon (30 mg) using the Parr hydrogenator at room temperature and 50 psig for 16 hours. The reaction mixture was filtered through Celite and the filtrate was concentrated under vacuum. Chromatography on C18 column (gradient elution, 5→20% methylene chloride+1% triethylamine/methanol) afforded the material, which was dissolved in cold 2:1 chloroform-methanol (8 mL) and washed with cold 0.1 N aqueous hydrochloric acid (1.6 mL). The lower organic layer was separated, dried over anhydrous sodium sulfate and concentrated in vacuo affording 28 mg (82%) of N—[(R)-3-decanoyloxytetradecanoyl]-O-[2,3-di-[(R)-3-decanoyloxytetradecanoylamino]-2,3-dideoxy-4-O-phosphono-β-D-allopyranosyl]-L-serine methyl ester as a glassy solid: $^1$H NMR (CDCl$_3$/CD$_3$OD): δ (ppm) 7.93 (d, J=8.0 Hz, 1H), 7.21 (d, J=9.0 Hz, 1H), 5.26-5.19 (m, 3H), 4.67-4.64 (m, 1H), 4.59 (d, J=2.5 Hz, 1H), 4.51-4.45 (m, 2H), 4.21-4.19 (m, 1H), 4.09-4.06 (m, 2H), 3.76 (s, 3H), 3.74-3.70 (m, 1H), 3.66-3.63 (m, 2H), 2.64-2.19 (m, 12H), 1.60 (br s, 12H), 1.26 (br s, 90H), 0.88 (t, J=7.0 Hz, 18H); HRMS (ESI-TOF) m/z: Calcd for C$_2$H$_{154}$N$_3$O$_{18}$P [M-H]$^-$ 1499.0887, found 1499.0816.

EXAMPLE 4

Preparation of N—[(R)-3-Decyloxytetradecanoyl]-O-[2,3-di-[(R)-3-decyloxytetradecanoylamino]-2,3-dideoxy-4-O-phosphono-]-β-D-allopyranosyl]-L-serine (Compound 4)

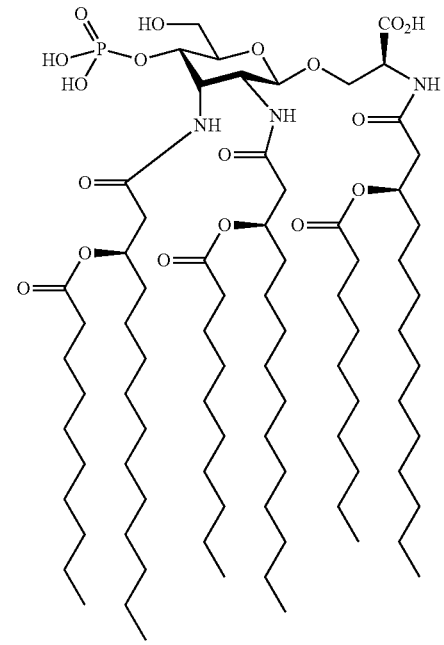

EXAMPLE 4A

In an analogous manner as Example 3F, a solution of the compound prepared in Example 3E (1.37 g, 2.07 mmol) was hydrogenated in the presence of 10% palladium on carbon (200 mg) and (0.20 mL) pyridine using the Parr hydrogenator at room temperature and 50 psig for 36 hours. The corresponding residue was acylated with (R)-3-decyloxytetradecanoic acid (2.64 g, 7.24 mmol) (U.S. Pat. No. 7,960,522) and 1-(3-dimethylaminopropyl)-3-ethylcarbodiimide methiodide (2.15 g, 7.24 mmol) afforded 940 mg (31%) of N—[(R)-3-decyloxytetradecanoyl]-O-[4,6-O-benzylidene-2-deoxy-2-[(R)-3-decyloxytetradecanoylamino]-3-deoxy-3-[(R)-3-decyloxytetradecanoylamino]-β-D-allopyranosyl]-L-serine methyl ester as a glassy solid.

EXAMPLE 4B

In an analogous manner as Example 1I, a solution of the compound prepared in Example 4A above (940 mg, 0.64 mmol) was treated with sodium cyanoborohydride (242 mg, 3.84 mmol) and trifluoroacetic acid (0.24 mL, 3.2 mmol) to afford 600 mg (64%) of N—[(R)-3-decyloxytetradecanoyl]-6-benzyl-4-hydroxy-2-deoxy-2-decyloxytetradecanamido-3-deoxy-3-[(R)-3-decyloxytetradecanoylamino-β-D-allopyranoside]-L-serine methyl ester as a colorless oil.

EXAMPLE 4C

In an analogous manner as Example 1J, a solution of the compound prepared in Example 4B above (450 mg, 0.31 mmol) was phosphorylated with dibenzyl diisopropylphosphoramidite (0.14 mL, 0.44 mmol), 4,5-dicyanoimidazole (51 mg, 0.44 mmol) and hydrogen peroxide (3 mL) affording 410 mg (78%) of N—[(R)-3-decyloxytetradecanoyl]-O-[6-O-benzyl-4-O-dibenzylphosphino-2,3-di-[(R)-3-decyloxytetradecanoylamino]-2,3-dideoxy-β-D-allopyranosyl]-L-serine methyl ester as a foamy solid.

EXAMPLE 4D

In an analogous manner as Example 1K, a solution of the compound prepared in Example 4C above (200 mg, 0.12 mmol) was hydrogenated in the presence of 10% palladium on carbon (80 mg) using the Parr hydrogenator at room temperature and 50 psig for 16 hours. The reaction mixture was filtered through a pad of Celite and the filtrate concentrated under vacuum. Chromatography on Cis column (gradient elution, 5→20% methylene chloride+1% triethylamine/methanol) afforded 70 mg (40%) of N—[(R)-3-decyloxytetradecanoyl]-O-[2,3-di-[(R)-3-decyloxytetradecanoylamino]-2,3-dideoxy-4-O-phosphino-β-D-allopyranosyl]-L-serine methyl ester as a glassy solid.

EXAMPLE 4E

A solution of the compound prepared in Example 4D above (70 mg, 0.048 mmol) was dissolved in THF (1 mL), cooled to 0° C. was hydrolyzed with 1 N sodium hydroxide (0.012 mL, 0.192 mmol) for 1 hour. The reaction mixture was neutralized with ice-cold 1 N hydrochloride bringing the pH to 3. The layers were separated and the aqueous layer was saturated with sodium chloride and extracted with chloroform (3×5 mL). The organic layers were combined, dried over anhydrous sodium sulfate, and concentrated in vacuo. Chromatography on silica gel was done with chloroform-methanol-water-triethylamine (gradient elution; 90:10:0.5:0.5→70:30:2:0.5). The fractions containing purified product were combined, concentrated in vacuo, then re-dissolved in cold 2:1 chloroform-methanol (14 mL) washed with cold 0.1 N aqueous hydrochloride (5.52 mL). The lower organic layer was separated, dried over anhydrous sodium sulfate and concentrated in vacuo affording 30 mg (41%) of N—[(R)-3-decyloxytetradecanoyl]-O-[2,3-di-[(R)-3-decyloxytetradecanoylamino]-2,3-dideoxy-4-O-phosphono-β-D-allopyranosyl]-L-serine as a glassy solid: $^1$H NMR (CDCl$_3$/CD$_3$OD): δ (ppm) 4.68-4.63 (m, 3H), 4.44-4.40 (m, 1H), 4.13 (dd, J=11 & 6.5 Hz, 1H), 4.08 (t, J=4.75 Hz, 1H), 3.79-3.66 (m, 6H), 3.50-3.38 (m, 7H), 2.52-2.28 (m, 6H), 1.53-1.50 (m, 12H), 1.33-1.25 (m, 96), 0.87 (t, J=7.0 Hz, 18H) HRMS (ESI-TOF) m/z: Calcd for C$_{81}$H$_{158}$N$_3$O$_{15}$P [M-H]$^-$ 1443.1352, found 1443.1295.

EXAMPLE 5

Preparation of N—[(R)-3-Decyloxytetradecanoyl]-O-[2,3-di-[(R)-3-decyloxytetradecanoylamino]-2,3-dideoxy-4-O-sulfoxy-β-D-allopyranosyl]-L-serine (Compound 5)

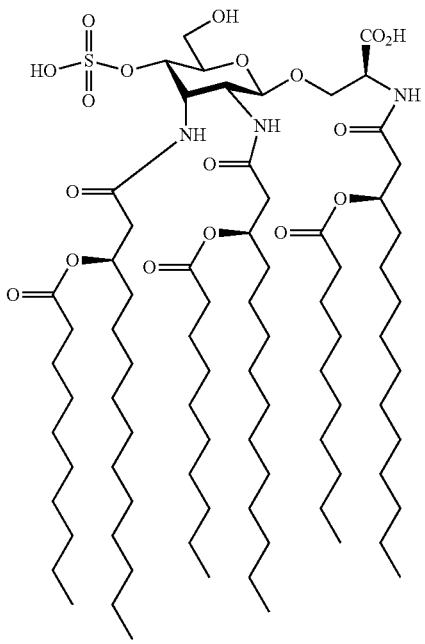

EXAMPLE 5A

A solution of the compound prepared in Example 4B (150 mg, 0.102 mmol) dissolved in anhydrous dimethylformamide (5 mL) was treated with sulfur trioxide triethylamine complex (111 mg, 0.613 mmol). The reaction was heated to 50° C. for 5 hours. An additional amount of sulfur trioxide triethylamine complex (111 mg, 0.613 mmol) was added again and the reaction stirred at 50° C. for 18 hours. The reaction mixture was concentrated in vacuo. Chromatography on silica gel was done with chloroform-methanol-water-triethylamine (gradient elution; 90:10:0.5:0.5→70:30:2:0.5) affording 96 mg (62%) of N—[(R)-3-decyloxytetradecanoyl]-O-[6-O-benzyl-2,3-di-[(R)-3-decyloxytetradecanoylamino]-2,3-dideoxy-4-O-sulfoxy-β-D-allopyranosyl]-L-serine methyl ester as a glassy solid.

EXAMPLE 5B

A solution of the compound prepared in Example 5A above (96 mg, 0.062 mmol) dissolved in a mixture of 2:1 anhydrous tetrahydrofuran:methanol (5 mL) was hydrogenated in the presence of 20% palladium hydroxide on carbon (60 mg) and triethylamine (0.044 mL, 0.0003 mmol) using the Parr hydrogenator at room temperature and 50 psig pressure for 18 hours. The reaction mixture was filtered through a pad of Celite and the filtrate was concentrated under vacuum. Chromatography on silica gel was done with chloroform-methanol-water-triethylamine (gradient elution; 90:10:0.5:0.5→70:30:2:0.5) affording 58 mg (55%) of N—[(R)-3-decyloxytetradecanoyl]-O-[2,3-di-[(R)-3-decyloxytetradecanoylamino]-2,3-dideoxy-4-O-sulfoxy-β-D-allopyranosyl]-L-serine methyl ester as a glassy solid.

EXAMPLE 5C

A solution of the compound prepared in Example 5B above (58 mg, 0.040 mmol) was dissolved in THF (2 mL), cooled to 0° C. and hydrolyzed with 1 N sodium hydroxide (0.08 mL, 0.08 mmol) for 1 hour. The reaction mixture was neutralized with ice-cold 1 N hydrochloride bringing the pH to 3. The layers were separated and the aqueous layer was saturated with sodium chloride and extracted with chloroform (3×5 mL). The combined organic layers were dried over anhydrous sodium sulfate and concentrated in vacuo. Chromatography on silica gel was done with chloroform-methanol-water-triethylamine (gradient elution; 90:10:0.5:0.5→70:30:2:0.5). The fractions containing purified product were combined, concentrated in vacuo, then re-dissolved in cold 2:1 chloroform-methanol (14 mL) and washed with cold 0.1 N aqueous hydrochloride (5.52 mL). The lower organic layer was dried over anhydrous sodium sulfate and concentrated in vacuo affording 15 mg (26%) of N—[(R)-3-decyloxytetradecanoyl]-O-[2,3-di-[(R)-3-decyloxytetradecanoylamino]-2,3-dideoxy-4-O-sulfoxy-β-D-allopyranosyl]-L-serine as a glassy solid: $^1$H NMR (CDCl$_3$/CD$_3$OD): δ (ppm) 7.74 (d, J=7.0 Hz, 1H), 7.30 (d, J=8.0 Hz, 1H), 7.02 (d, J=8.0 Hz, 1H), 4.62-4.55 (m, 3H), 4.17-4.08 (m, 3H), 3.71-3.60 (m, 5H), 3.45-3.31 (m, 6H), 2.49-2.25 (m, 6H), 1.48-1.45 (m, 12H), 1.33-1.25 (m, 96H) 0.87 (t, J=7.0 Hz, 18H); HRMS (ESI-TOF) m/z: Calcd for $C_{81}H_{157}N_3O_{15}S$ [M-H]$^-$ 1443.1257, found 1443.1187.

EXAMPLE 6

Preparation of 2-[(R)-3-decanoyloxytetradecanoylamino]ethyl 2,3-di-[(R)-3-decanoyloxytetradecanoylamino]-2,3-dideoxy-4-O-methylphosphono-β-D-allopyranoside (Compound 6)

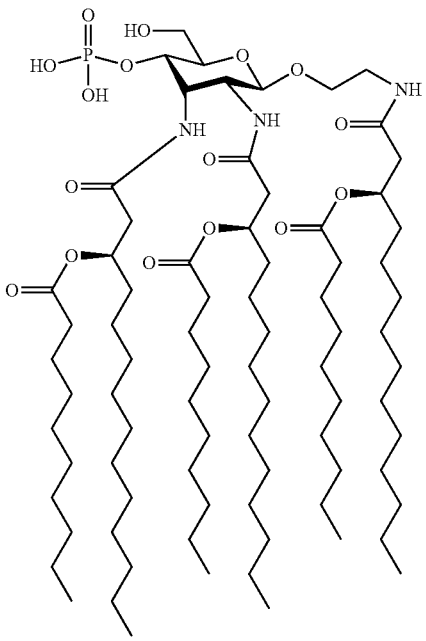

EXAMPLE 6A

A solution of paraformaldehyde (190 mg, 6.3 mmol) in dibenzylphosphite (1.54 g, 5.87 mmol) was treated with anhydrous triethylamine (100 mg, mmol). The reaction was heated to 50° C. for 15 minutes and the temperature gradually increased to 85° C. for 2 hours. The reaction mixture was diluted with chloroform (20 mL) then concentrated in vacuo. Chromatography on silica gel (gradient elution, 20→100% ethyl acetate/heptane) afforded 1.04 g (58%) of dibenzylhydroxymethylphosphonate as a colorless oil.

EXAMPLE 6B

A solution of the compound prepared in Example 6A above (500 mg, 1.71 mmol) and 2,6-lutidine (5.0 mL, 42.8 mmol) in anhydrous methylene chloride (5 mL) and cooled to −50° C. was treated with dropwise addition of triflic anhydride (0.33 mL, 2.05 mmol). The reaction was allowed to gradually warm up to 0° C. The reaction mixture was diluted with Et$_2$O (30 mL) and washed sequentially with H$_2$O (10 mL), 1 N HCl (10 mL) and brine (10 mL). The organic layer was dried over anhydrous sodium sulfate and concentrated in vacuo affording 724 mg (quant.) of [di(benzyloxy)phosphoryl]methyl triflate as a pink oil.

EXAMPLE 6C

A solution of the compound prepared in Example 1I (100 mg, 0.065 mmol) in anhydrous THF (2 mL) was cooled to 0° C. under inert atmosphere and treated with a solution of 1 M lithium bis(trimethylsilyl)amide in tetrahydrofuran (0.089 mL, 0.085 mmol). The reaction was stirred at 0° C. for 10 minutes, after which it was treated with dropwise addition of a tetrahydrofuran solution (0.5 mL) of the compound prepared in Example 6B above (50 mg, 0.24 mmol). The reaction mixture was quenched with 0.1 N hydrochloride (5 drops), diluted with chloroform (5 mL), separated and the organic was washed with saturated aqueous sodium bicarbonate (2 mL). The aqueous layer was extracted with chloroform (2×5 mL) and the combined organic layers were dried over anhydrous sodium sulfate and concentrated in vacuo. Chromatography on silica gel (gradient elution, 20→100% ethyl acetate/heptane) afforded 43 mg (36%) of 2-[(R)-3-decanoyloxytetradecanoylamino] ethyl 6-O-benzyl-4-O-dibenzylmethylphosphono-2,3-di-[(R)-3-decanoyloxytetradecanoylamino]-2,3-dideoxy-β-D-allopyranoside as a colorless oil.

EXAMPLE 6D

A solution of the compound prepared in Example 6C above (43 mg, 0.025 mmol) dissolved in anhydrous tetrahydrofuran (20 mL) was hydrogenated using an H-Cube with 10% palladium on carbon (30 mm CatCart®, full H2 mode at 60° C. for 1 minute, which is hydrogenation at ambient pressure, where the introduced H2 amount was 30 mL/min). The reaction mixture was concentrated in vacuo. After chromatographic on silica gel with chloroform-methanol-water-triethylamine (gradient elution; 90:10:0.5:0.5→70:30:2:0.5), the fractions containing purified product were combined, concentrated in vacuo, re-dissolved in cold 2:1 chloroform-methanol (8.6 mL) and washed with cold 0.1

N aqueous hydrochloride (3.4 mL). The lower organic layer was dried over anhydrous sodium sulfate and concentrated in vacuo affording 27 mg (75%) of 2-[(R)-3-decanoyloxytetradecanoylamino]ethyl 2,3-di-[(R)-3-decanoyloxytetradecanoylamino]-2,3-dideoxy-4-O-methylphosphono-β-D-allopyranoside as a glassy solid: $^1$H NMR (CDCl$_3$/CD$_3$OD): δ (ppm) 5.19-5.16 (m, 3H); 4.54-4.52 (m, 2H); 3.98 (s, 2H); 3.84-3.82 (m, 1H); 3.78-3.75 (m, 2H); 3.71 (s, 1H); 3.68-3.63 (m, 2H); 3.45-3.37 (m, 2H); 3.31-3.29 (m, 1H); 2.54-2.37 (m, 6H); 2.28-2.22 (m, 6H); 1.56 (br s, 12H); 1.22 (br s, 90H); 0.85 (t, J=7.25 Hz, 18H); HRMS (ESI-TOF) m/z: Calcd for $C_{81}H_{154}N_3O_{16}P$ [M-H]$^+$ 1457.1145, found 1457.1185.

EXAMPLE 7

Preparation of N—[(R)-3-Decyloxytetradecanoyl]-O-[2,3-di-[(R)-3-decyloxytetradecanoylamino]-2,3-dideoxy-4-O-methylphosphono-β-D-allopyranosyl]-L-serine triethylammonium salt (Compound 7)

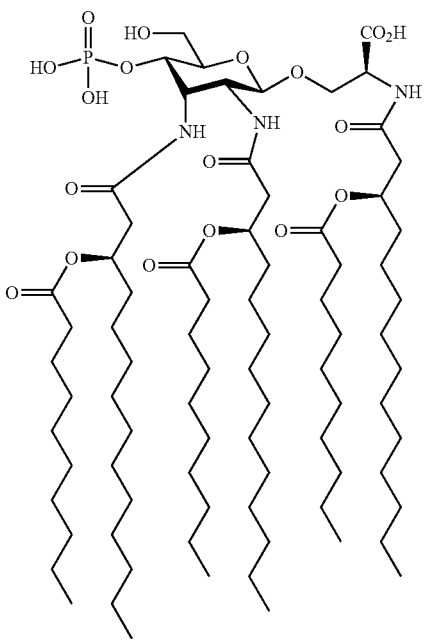

EXAMPLE 7A

In an analogous manner as Example 6C, a solution of the compound prepared in Example 4B above (150 mg, 0.102 mmol) in anhydrous THE (2 mL) was cooled to 0° C. under inert atmosphere and treated with a solution of 1 M lithium bis(trimethylsilyl)amide in tetrahydrofuran (0.135 mL, 0.133 mmol). The reaction was stirred at 0° C. for 10 minutes, after which it was treated with dropwise addition of a tetrahydrofuran solution (0.5 mL) of the compound prepared in Example 6B above (90 mg, 0.173 mmol). The reaction stirred at 0° C. for 2 h. The reaction mixture was quenched with 0.1 N hydrochloride (5 drops), diluted with chloroform (5 mL), separated and the organic layer was washed with saturated aqueous sodium bicarbonate (2 mL). The aqueous layer was extracted with chloroform (2×5 mL) and the combined organic layers were dried over anhydrous sodium sulfate and concentrated in vacuo. Chromatography on silica gel (gradient elution, 20→100% ethyl acetate/heptane) afforded 48 mg (27%) of N—[(R)-3-decyloxytetradecanoyl]-O-[6-O-benzyl-2,3-di-[(R)-3-decyloxytetradecanoylamino]-2,3-dideoxy-4-O-dibenzylmethylphosphono-β-D-allopyranosyl]-L-serine methyl ester as a colorless oil.

EXAMPLE 7B

A solution of the compound prepared in Example 7A above (160 mg, 0.092 mmol) dissolved in anhydrous tetrahydrofuran (20 mL) was hydrogenated in the presence of 10% palladium on carbon (48 mg) using the Parr hydrogenator at room temperature and 50 psig pressure for 18 hours. The reaction mixture was filtered through a pad of Celite and the filtrate was concentrated under vacuum. Reverse phase chromatography using a C18 column (gradient elution, 0→100% chloroform/methanol) afforded 91 mg (67%) of N—[(R)-3-decyloxytetradecanoyl]-O-[2,3-di-[(R)-3-decyloxytetradecanoylamino]-2,3-dideoxy-4-O-methylphosphono-β-D-allopyranosyl]-L-serine methyl ester as a glassy solid.

EXAMPLE 7C

A solution of the compound prepared in Example 7B above (91 mg, 0.062 mmol) was dissolved in THE (2 mL), cooled to 0° C. and hydrolyzed with 1 N lithium hydroxide (0.26 mL, 0.26 mmol) for 1 hour. The reaction mixture was neutralized with ice-cold 1 N hydrochloride bringing the pH to 5. The layers were separated and the aqueous layer was saturated with sodium chloride and extracted with chloroform (3×5 mL). The combined organic layers were dried over anhydrous sodium sulfate and concentrated in vacuo. Chromatography on silica gel was done (gradient elution; 0→30% [90:10 MeOH/H$_2$O]/chloroform). The fractions containing purified product were combined, concentrated in vacuo, then re-dissolved in cold 2:1 chloroform-methanol (14 mL) and washed with cold 0.1 N aqueous hydrochloride (5.52 mL). The lower organic layer was separated, dried over anhydrous sodium sulfate, concentrated in vacuo, then salted with triethyl amine affording 56 mg (62%) of N—[(R)-3-decyloxytetradecanoyl]-O-[2,3-di-[(R)-3-decyloxytetradecanoylamino]-2,3-dideoxy-4-O-methylphosphono-β-D-allopyranosyl]-L-serine triethylammonium salt as a glassy solid: $^1$H NMR (CDCl$_3$/CD$_3$OD): δ (ppm) 4.61-4.54 (m, 2H); 4.14-4.06 (m, 2H); 3.84 (br m, 2H); 3.69 (br m, 6H); 3.47-3.39 (m, 8H); 3.09 (q, J=7.6 Hz, 2H, CH$_2$ of Et$_3$N (~½ equiv); 2.47-2.33 (m, 6H); 1.51-1.45 (m, 12H); 1.26-1.14 (m, 101H); 0.88 (t, J=7.0 Hz, 18H); HRMS (ESI-TOF) m/z: Calcd for $C_2H_{160}N_3O_{15}P$ [M-H]$^-$ 1457.1507, found 1457.1367.

EXAMPLE 8

Preparation of 2-[(R)-3-(8-phenyl)octanoyloxytetra-decanoylamino]ethyl 2,3-di-[(R)-3-(8-phenyl)oc-tanoyloxytetradecanoylamino]-2,3-dideoxy-4-O-phosphono-β-D-allopyranoside triethylammonium Salt (Compound 8)

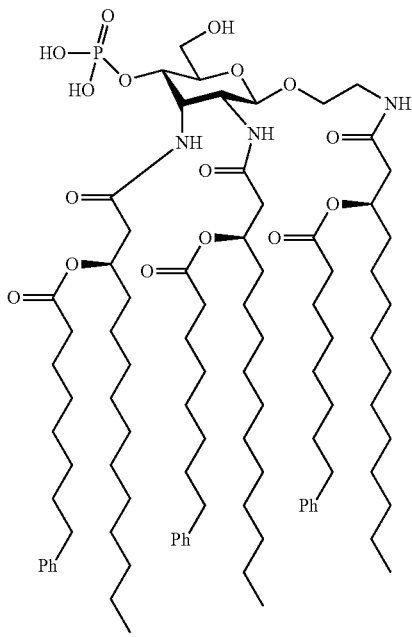

EXAMPLE 8A

In an analogous manner as Example 1G, a solution of the compound prepared in Example 1F above (250 mg, 0.43 mmol) in anhydrous methylene chloride (10 mL) was acylated with (R)-3-(8-phenyl)octanoyloxytetradecanoic acid (231 mg, 0.52 mmol) (prepared from acylating (R)-3-hydroxyltetradecanoyl ester with 8-phenyloctanoic acid) and 1-(3-dimethylaminopropyl)-3-ethylcarbodiimide methiodide (153 mg, 0.52 mmol) to afford 378 mg (88%) of 2-(benzyloxycarbonylamino)ethyl 4,6-O-benzylidene-2-benzyloxycarbonylamino-3-[(R)-3-(8-phenyl)octanoyloxytetradecanoylamino]-2,3-dideoxy-β-D-allopyranoside as a colorless oil.

EXAMPLE 8B

In an analogous manner as Example 1H, a solution of the compound prepared in Example 8A above (189 mg, 0.19 mmol) in anhydrous tetrahydrofuran (10 mL) was hydrogenated with 10% palladium on carbon (50 mg) using a Parr hydrogenator at room temperature and 50 psig for 18 hours. The reaction mixture was filtered through Celite and the filtrate concentrated in vacuo. The resulting oil dissolved in methylene chloride (10 mL) was acylated with (R)-3-(8-phenyl)octanoyloxytetradecanoic acid (180 mg, 0.402 mmol) and 1-(3-dimethylaminopropyl)-3-ethylcarbodiimide methiodide (119 mg, 0.402 mmol) at room temperature for 2 hours. The reaction mixture was quenched with saturated aqueous sodium bicarbonate (10 mL) and the layers separated. The aqueous layer was extracted with methylene chloride (2×10 mL) and the combined organic layers washed with water (10 mL), dried over anhydrous sodium sulfate and concentrated in vacuo. Chromatography on silica gel (gradient elution, 20→80% ethyl acetate/heptane) afforded 290 mg (99%) of 2-[(R)-3-(8-phenyl)octanoyloxytetradecanoylamino]ethyl 4,6-O-benzylidene-2,3-di-[(R)-3-(8-phenyl)octanoyloxytetradecanoylamino]-2,3-dideoxy-β-D-allopyranoside as a glassy solid.

EXAMPLE 8C

In an analogous manner as Example 11, a solution of the compound prepared in Example 8B above (290 mg, 0.182 mmol) was treated with sodium cyanoborohydride (57 mg, 0.91 mmol) and trifluoroacetic acid (0.083 mL, 1.09 mmol) to afford 231 mg (80%) of 2-[(R)-3-(8-phenyl)octanoyloxytetradecanoylamino]ethyl 6-O-benzyl-2,3-di-[(R)-3-(8-phenyl)octanoyloxytetradecanoylamino]-2,3-dideoxy-β-D-allopyranoside as a colorless oil.

EXAMPLE 8D

In an analogous manner as Example 1J, a solution of the compound prepared in Example 8C above (231 mg, 0.145 mmol) in anhydrous methylene chloride (10 mL) was phosphorylated with dibenzyl diisopropylphosphoramidite (0.070 mL, 0.203 mmol) and 4,5-dicyanoimidazole (24 mg, 0.203) and hydrogen peroxide (2 mL) to afford 269 mg (76%) of 2-[(R)-3-(8-phenyloctanoyloxytetradecanoylamino]ethyl 6-O-benzyl-4-O-dibenzylphosphino-2,3-di-[(R)-3-(8-phenyl)octanoyloxytetradecanoylamino]-2,3-dideoxy-β-D-allopyranoside as a foamy solid.

EXAMPLE 8E

In an analogous manner as Example 1K, a solution of the compound prepared in Example 8D above (269 mg, 0.145 mmol) in anhydrous tetrahydrofuran (5 mL) was hydrogenated in the presence of 10% palladium on carbon (50 mg) under atmospheric hydrogen gas (H2 balloon) for 18 hours. The reaction mixture was filtered through Celite and the filtrate was concentrated under vacuum. Chromatography on silica gel with chloroform-methanol-water-triethylamine (gradient elution; 90:10:0.5:0.5→70:30:2:0.5). The fractions containing purified product were combined, concentrated in vacuo, then re-dissolved in cold 2:1 chloroform-methanol (17 mL) and washed with cold 0.1 N aqueous hydrochloride (6.72 mL). The lower organic layer was dried over anhydrous sodium sulfate, concentrated in vacuo and salted with triethylamine affording 75 mg (33%) of 2-[(R)-3-(8-phenyl)octanoyloxytetradecanoylamino]ethyl 2,3-di-[(R)-3-(8-phenyl)octanoyloxytetradecanoylamino]-2,3-dideoxy-4-O-phosphono-3-D-allopyranoside triethylammonium salt as a glassy solid: $^1$H NMR (CDCl$_3$/CD$_3$OD): δ (ppm) 7.69 (br s, 1H), 7.26-7.16 (m, 15H), 5.21 (br s, 3H), 4.54-4.39 (m, 3H), 4.09-4.05 (m, 2H), 3.78 (br s, 3H), 3.53-3.39 (m, 4H), 3.08 (q, J=6.8 Hz, 5H, CH$_2$ of Et$_3$N (~⅚ equiv), 2.58-2.46 (m, 12H), 2.27 (br m, 6H), 1.58 (br s, 12H), 1.31-1.24 (m, 81H), 0.87 (t, J=6.8 Hz, 9H); HRMS (ESI-TOF) m/z: Calcd for C$_{92}$H$_{152}$N$_3$O$_{16}$P [M-H]$^-$ 1586.0832, found 1586.0799.

EXAMPLE 9

Preparation of 2-[(R)-3-decanoyloxytetradecanoylamino]ethyl, 2-[(R)-3-decanoyloxytetradecanoylamino]-3-[(R)-3-(8-phenyl)octanoyloxytetradecanoylamino]-2,3-dideoxy-4-O-phosphono-β-D-allopyranoside triethylammonium salt (Compound 9)

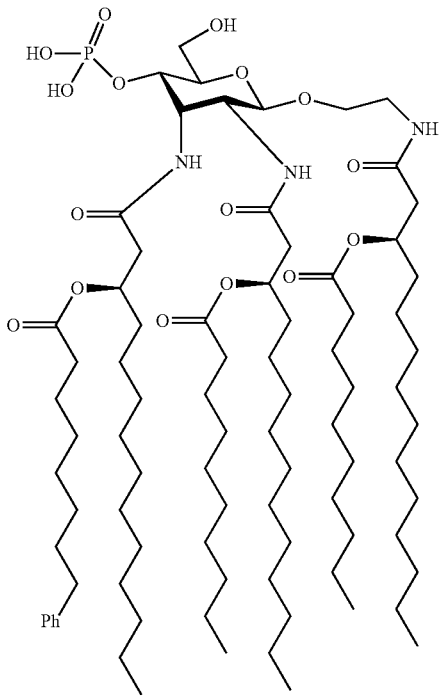

EXAMPLE 9A

In an analogous manner as Example 1H, a solution of the compound prepared in Example 8A above (189 mg, 0.19 mmol) in anhydrous tetrahydrofuran (10 mL) was hydrogenated with 10% palladium on carbon (50 mg) using a Parr hydrogenator at room temperature and 50 psig for 18 hours. The reaction mixture was filtered through Celite and the filtrate concentrated in vacuo. The resulting oil dissolved in methylene chloride (10 mL) was acylated with (R)-3-decanoyloxytetradecanoic acid (160 mg, 0.402 mmol) and 1-(3-dimethylaminopropyl)-3-ethylcarbodiimide methiodide (119 mg, 0.402 mmol) at room temperature for 2 hours. The reaction mixture was quenched with saturated aqueous sodium bicarbonate (10 mL) and the layers separated. The aqueous layer was extracted with methylene chloride (2×10 mL) and the combined organic layers washed with water (10 mL), dried over anhydrous sodium sulfate and concentrated in vacuo. Chromatography on silica gel (gradient elution, 20→80% ethyl acetate/heptane) afforded 145 mg (53%) of 2-[(R)-3-decanoyloxytetradecanoylamino]ethyl 4,6-O-benzylidene-2-[(R)-3-decanoyloxytetradecanoylamino]-3-[(R)-3-(8-phenyl)octanoyloxytetradecanoylamino]-2,3-dideoxy-β-D-allopyranoside as a glassy solid.

EXAMPLE 9B

In an analogous manner as Example 1I, a solution of the compound prepared in Example 9A above (145 mg, 0.097 mmol) was treated with sodium cyanoborohydride (30 mg, 0.48 mmol) and trifluoroacetic acid (0.044 mL, 0.58 mmol) to afford 103 mg (71%) of 2-[(R)-decanoyloxytetradecanoylamino]ethyl 6-O-benzyl-2-[(R)-3-decanoyloxytetradecanoylamino]-3-[(R)-3-(8-phenyl)octanoyloxytetradecanoylamino]-2,3-dideoxy-β-D-allopyranoside as a colorless oil.

EXAMPLE 9C

In an analogous manner as Example 1J, a solution of the compound prepared in Example 9B above (103 mg, 0.069 mmol) in anhydrous methylene chloride (10 mL) was phosphorylated with dibenzyl diisopropylphosphoramidite (0.033 mL, 0.096 mmol) and 4,5-dicyanoimidazole (11 mg, 0.096) and treated with hydrogen peroxide (2 mL) to afford 105 mg (87%) of 2-[(R)-3-decanoyloxytetradecanoylamino]ethyl 6-O-benzyl-4-O-dibenzylphosphino-2-[(R)-3-decanoyloxytetradecanoylamino]-3-[(R)-3-(8-phenyl)octanoyloxytetradecanoylamino]-2,3-dideoxy-β-D-allopyranoside as a glassy solid.

EXAMPLE 9D

In an analogous manner as Example 1K, a solution of the compound prepared in Example 9C above (100 mg, 0.057 mmol) in anhydrous tetrahydrofuran (5 mL) was hydrogenated in the presence of 10% palladium on carbon (30 mg) under hydrogen atmospheric pressure (H2 balloon) for 18 hours. The reaction mixture was filtered through Celite and the filtrate was concentrated under vacuum. Chromatography on silica gel with chloroform-methanol-water-triethylamine (gradient elution; 90:10:0.5:0.5→70:30:2:0.5). The fractions containing purified product were combined, concentrated in vacuo, then re-dissolved in cold 2:1 chloroform-methanol (12 mL) and washed with cold 0.1 N aqueous hydrochloric (4.8 mL). The lower organic layer was dried over anhydrous sodium sulfate, concentrated in vacuo and salted with triethylamine affording 36 mg (43%) of 2-[(R)-3-decanoyloxytetradecanoylamino]ethyl 2-[(R)-3-decanoyloxytetradecanoylamino]-3-[(R)-3-(8-phenyl)octanoyloxytetradecanoylamino]-2,3-dideoxy-4-O-phosphono-β-D-allopyranoside as a glassy solid: $^1$H NMR (CDCl$_3$/CD$_3$OD): δ (ppm) 7.56 (br s, 1H), 7.10-7.18 (m, 5H), 5.14 (br m, 3H), 4.33-4.47 (m, 3H), 3.97-4.03 (m, 2H), 3.63-3.75 (m, 3H), 3.13-3.40 (m, 3H), 3.01 (q, J=6.8 Hz, 6H, CH$_2$ of Et$_3$N (~1 equiv), 2.38-2.52 (m, 8H), 2.21 (br s, 6H), 1.52 (br s, 12H), 1.18-1.25 (m, 87H), 0.88 (t, J=6.4 Hz, 15H); HRMS (ESI-TOF) m/z: Calcd for C$_4$H$_{152}$N$_3$O$_{16}$P [M]$^-$ 1490.0910, found 1490.0813.

6. Biological and Stability Data

Figure 1B:
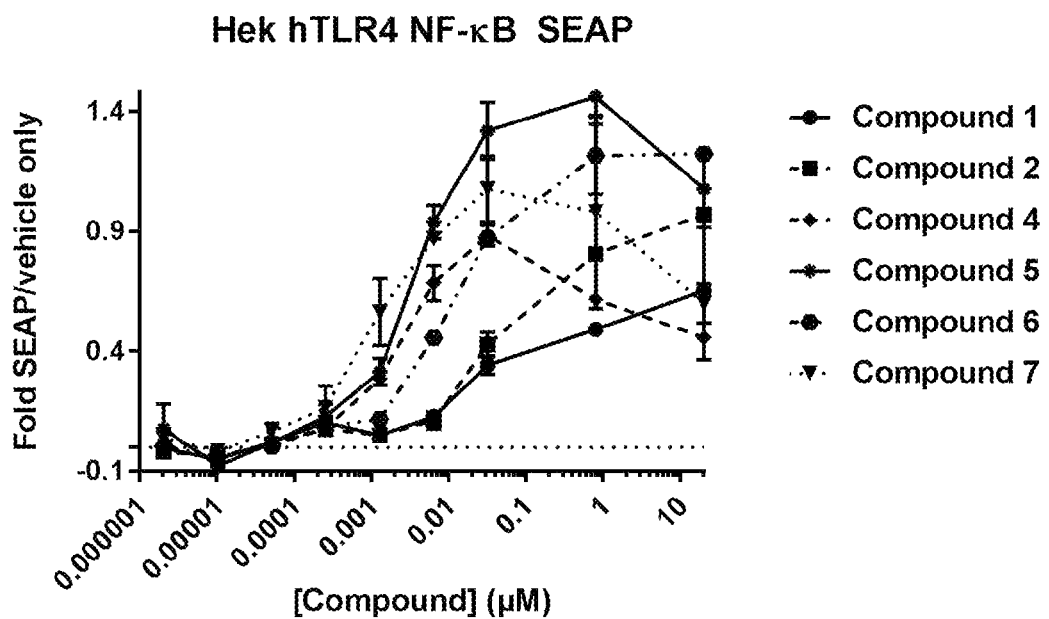
Figure 1C:
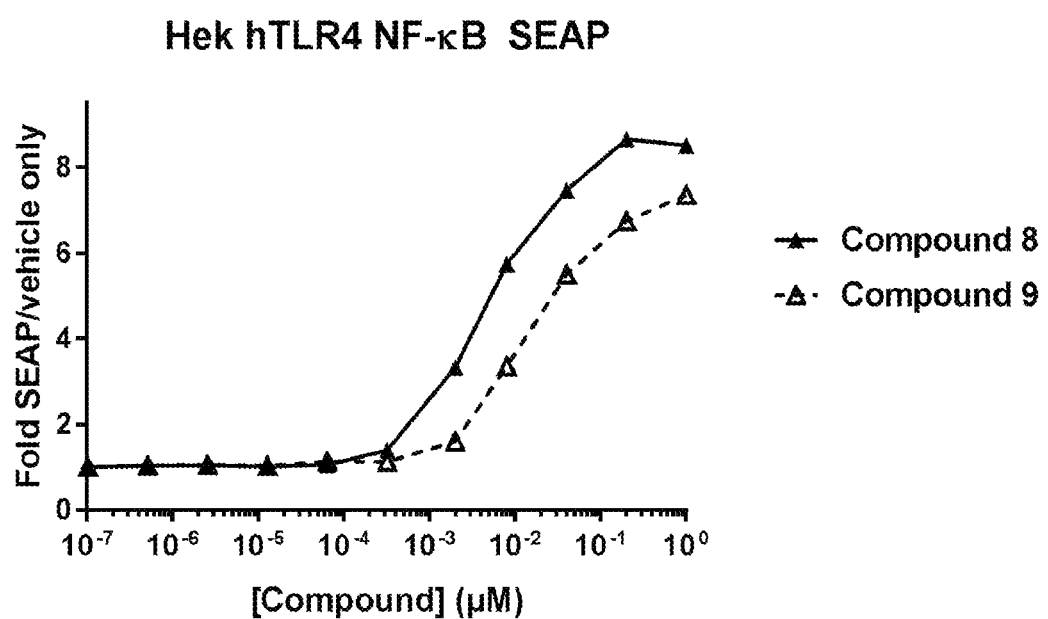

In vitro assays were conducted with Compounds 1-9 and the commercially available TLR4 agonist MPL. For measurement of biological activity various cells were stimulated with a wide dose range of each compound followed by assessment of either transcriptional activation (HEK hTLR4 NF-κB-SEAP cells) or cytokine production (hMM6 or hPBMCs). Dose-response curves for each compound were started at either 100 μM or 20 μM followed by 5-fold serial dilutions in vehicle (2% glycerin or glycine, "IN") with final concentrations being 1.6×10$^{-8}$ μM (1.6 fM) or 3.3×10$^{-8}$ μM (3.3 fM). After incubation for 18-24 h with the dose range of compounds cellular supernatants were harvested for analysis.

hTLR4 activation. HEK hTLR4-expressing cells were treated with 100 μM concentration of test compound followed by a 5-fold dilution series. HEK hTLR4-expressing cells also contained an NF-κB driven SEAP reporter and were stimulated with the indicated concentration (FIG. 1A-1C) of the test compound for 18 hours followed by assessment of the cellular supernatant for SEAP by a Quantikine SEAP assay (InvivoGen). The SEAP assay was used to look at secretion of the NF-κB driven alkaline-phosphatase reporter gene in response to TLR4 activation by the compounds and results are interpreted both in terms of potency of the compounds to induce SEAP activation (i.e. potency where a lower EC50 indicates higher potency) and efficacy for receptor activation (i.e. maximal SEAP induction). EC50 values for each compound in HEK hTLR4 cells are shown in Tables 1a and 1b. EC50 values were determined by fitting dose response curves to a non-linear 4-parameter equation.

TABLE 1a

| Hek hTLR4 EC50 (nM) | | | | |
| --- | --- | --- | --- | --- |
| Compound 1 | Compound 2 | Compound 3 | Compound 4 | MPL |
| 13.68 | 63.98 | 3.952 | 1.319 | 151.9 |

TABLE 1b*

| Hek hTLR4 EC50 (nM) | | | | | | | | |
| --- | --- | --- | --- | --- | --- | --- | --- | --- |
| 1 | 2 | 4 | 5 | 6 | 7 | 8 | 9 | |
| 19.67 | 41.02 | 1.39 | 2.90 | 10.23 | 0.78 | 4.99 | 15.67 | |

*Numbers 1-9 refer to Compounds 1-9, respectively.

Figure 2A:
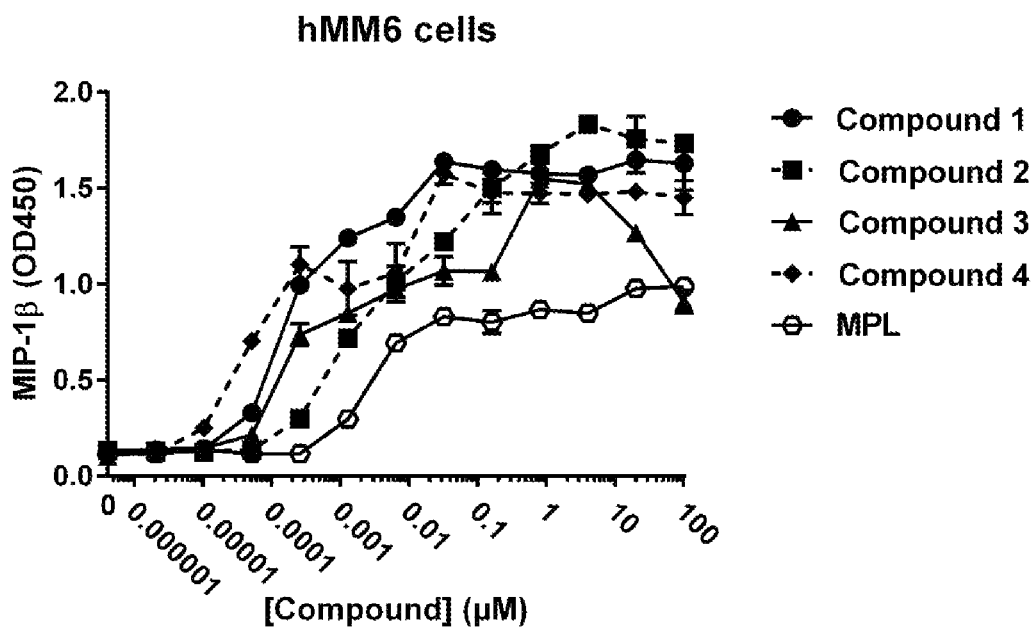
FIGS. 2A and 2B show induction of MIP-1β cytokine from hMM6 cells in response to compounds. hMM6 cells, a monocytic/macrophage cell line, were subjected to treatment with increasing concentrations of the indicated compound for 18 hours. Supernatants were harvested and analyzed for production of MIP-1β via ELISA.
Figure 2B:
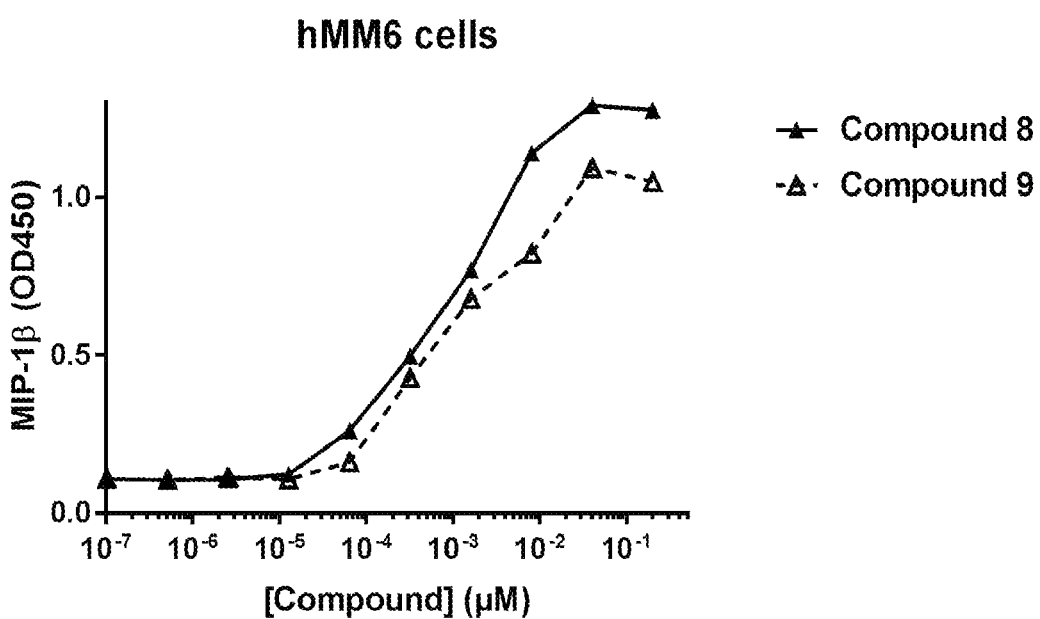

Induction of MIP-1β cytokine from hMM6 cells. The compounds were next tested in the established MM6 potency assay measuring MIP-1β cytokine production as an output measure of compound potency. Human monocytic cell line, Mono-Mac-6 (hMM6) was obtained from DSMZ (Brunswick, Germany). Cells were maintained in T-75 flasks and cultured at $1.53 \times 10^5$ cells/well in 96-well tissue culture plates with RPMI-1640 media (HyClone™, Logan, Utah), Pen/Strep/Glutamine (HyClone™, Logan, Utah), 2-Mercaptoethanol (Gibco, Grand Island, N.Y.) and 10% heat inactivated FBS (Corning, Manassas, Va.). hMM6 cells were subjected to treatment with increasing concentrations of the indicated compound for 18 hours (FIG. 2A-2B). Treatments started at a 100 μM concentration proceeded with a 16-point, 5-fold dilution series. Supernatants were harvested and analyzed for production of MIP-1β via ELISA (R&D systems, catalog #DY271). EC50 values for each compound in hMM6 cells are shown in Table 2. EC50 values were determined by fitting dose response curves to a non-linear 4-parameter equation.

TABLE 2

| hMM6 MIP-1β EC50 (nM) | | | | |
| --- | --- | --- | --- | --- |
| Compound 1 | Compound 2 | Compound 3 | Compound 4 | MPL |
| 0.2514 | 5.893 | 0.4623 | 0.1236 | 3.095 |

Figure 3:
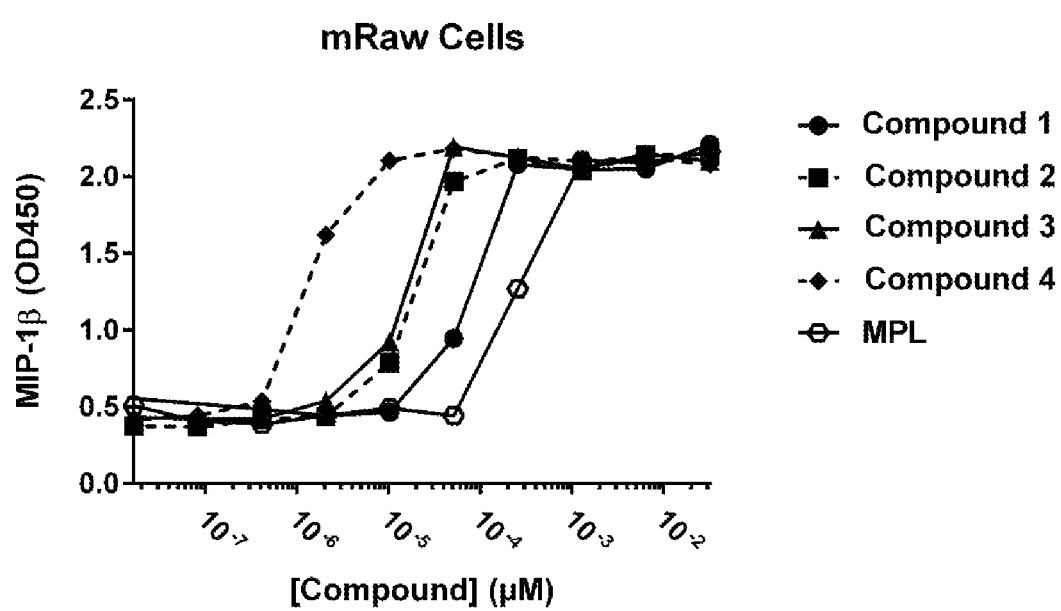
FIG. 3 shows induction of MIP-1β cytokine from murine RAW264.7 cells in response to compounds. mRAW264.7 cells, a macrophage cell line, were subjected to treatment with increasing concentrations of the indicated compound for 18 hours. Supernatants were harvested and analyzed for production of MIP-1β via ELISA.

Induction of MIP-1β cytokine from mRAW264.7 cells. To determine if the compounds also have activity in a murine cell, all of the compounds were tested in RAW cells, a mouse macrophage cell line. mRAW264.7 cells, were subjected to treatment with increasing concentrations of the indicated compound for 18 hours (FIG. 3). Treatments started at 20 μM concentration with a 5-fold serial dilution until 3.2768E-09 μM. Supernatants were harvested and analyzed for production of MIP-1β via ELISA (R& D Systems-cat #DY451). EC50 values for each compound in mRAW264.7 cells are shown in Table 3. EC50 values were determined by fitting dose response curves to a non-linear 4-parameter equation.

TABLE 3

| mRaw MIP-1β EC50 (nM) | | | | |
| --- | --- | --- | --- | --- |
| Compound 1 | Compound 2 | Compound 3 | Compound 4 | MPL |
| 0.0576 | 0.0176 | 0.0112 | 0.0014 | 0.2583 |

Figure 4A:
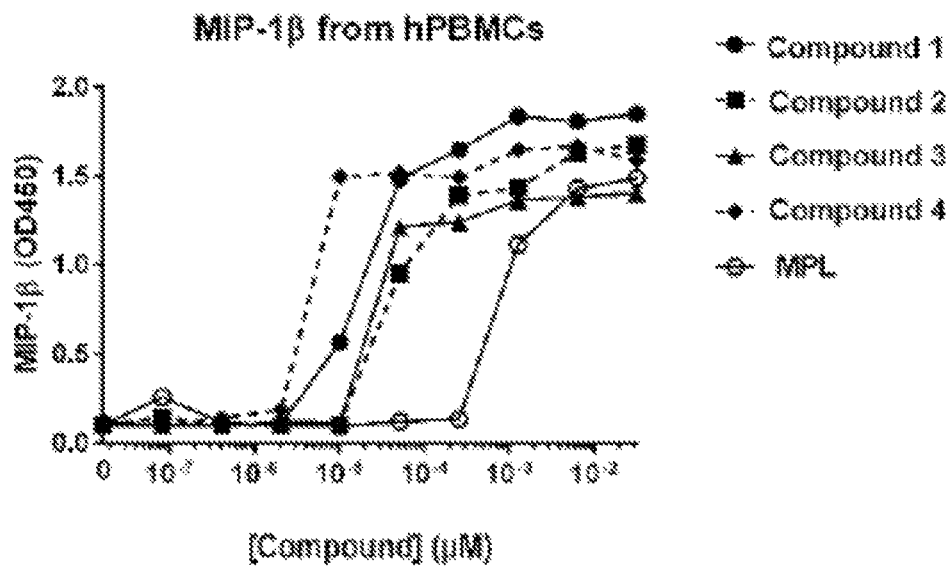
FIG. 4A shows induction of MIP-1β from primary hPBMCs in response to compounds 1-4 (average of 3 donors).
Figure 4B:
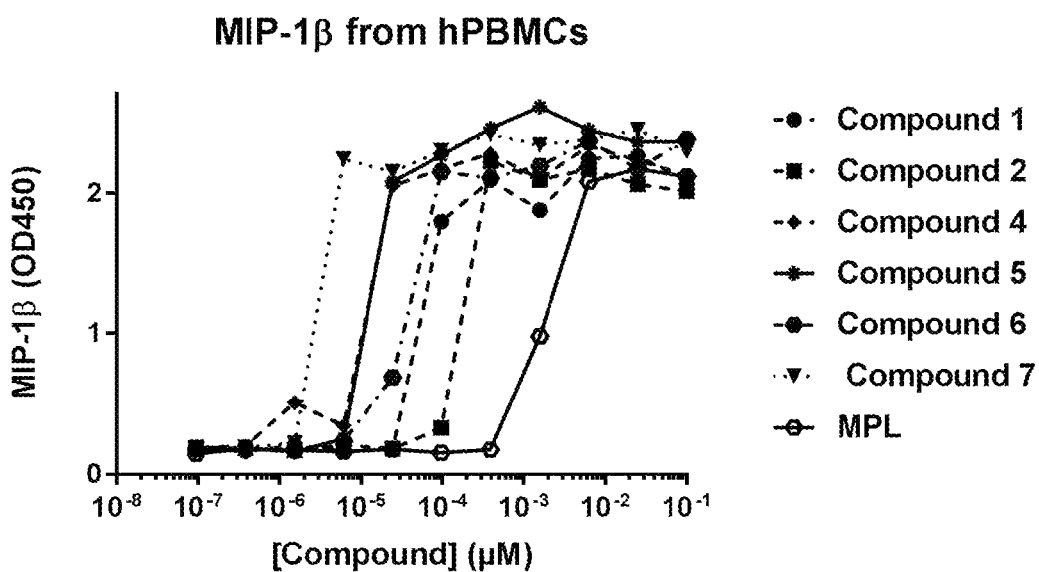
FIG. 4B shows induction of MIP-1β from primary hPBMCs in response to compounds 1, 2, 4, 5, 6, and 7 (shown in one donor).
Figure 4C:
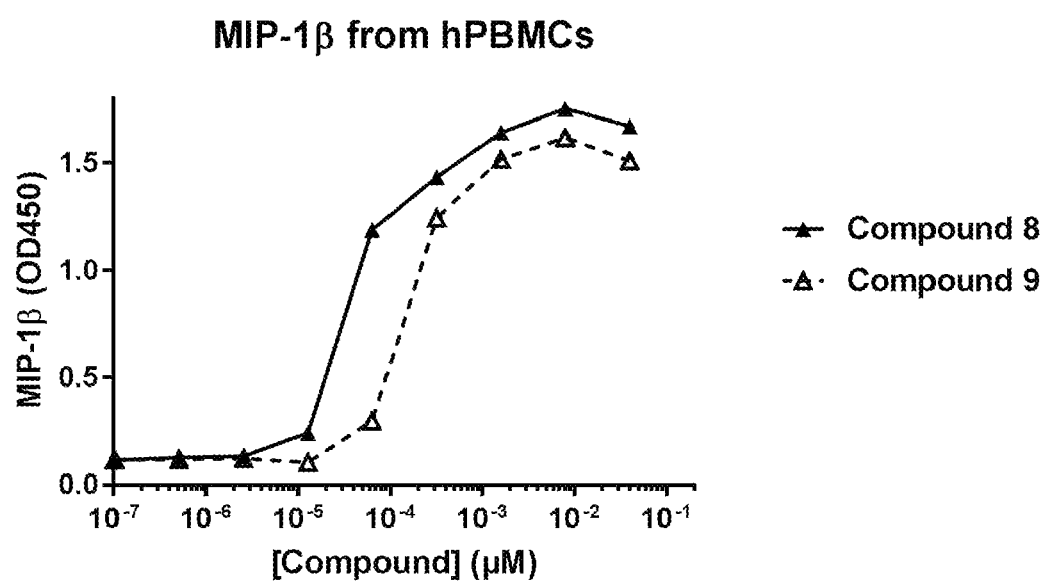
FIG. 4C shows induction of MIP-1β from primary hPBMCs in response to compounds 8 and 9 (shown in one donor). Primary human peripheral blood mononuclear cells were isolated from the whole blood of three different donors using a Ficoll gradient. Cells were then subjected to treatment with increasing concentrations of the indicated compound for 18 hours and supernatants were analyzed for production of MIP-1β.
Figure 5A:
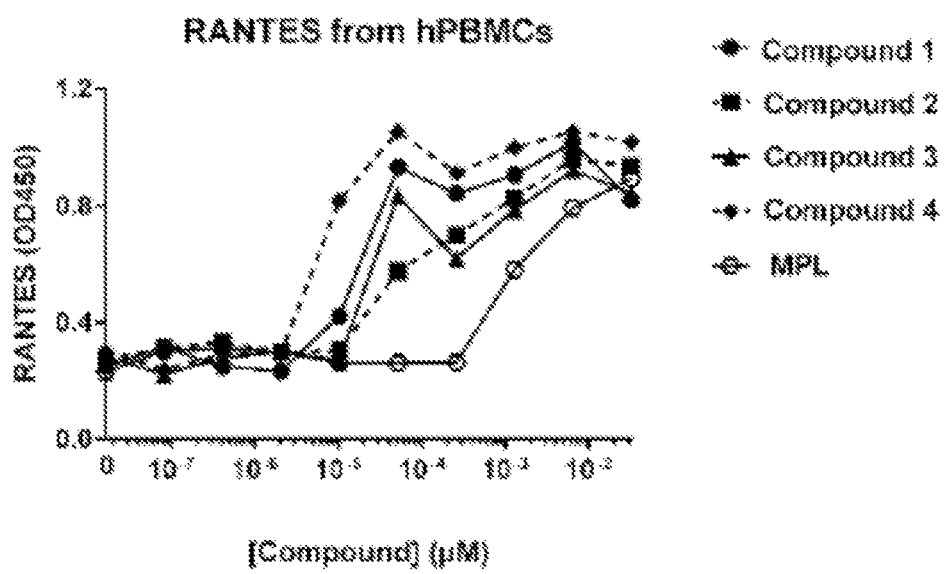
FIG. 5A (average of 3 donors), 5B (1 donor), and 5C (1 donor) show induction of RANTES from primary hPBMCs in response to compounds. Primary human peripheral blood mononuclear cells were isolated from the whole blood of three different donors using a Ficoll gradient. Cells were then subjected to treatment with increasing concentrations of the indicated compound for 18 hours and supernatants were analyzed for production of RANTES via ELISA.
Figure 5B:
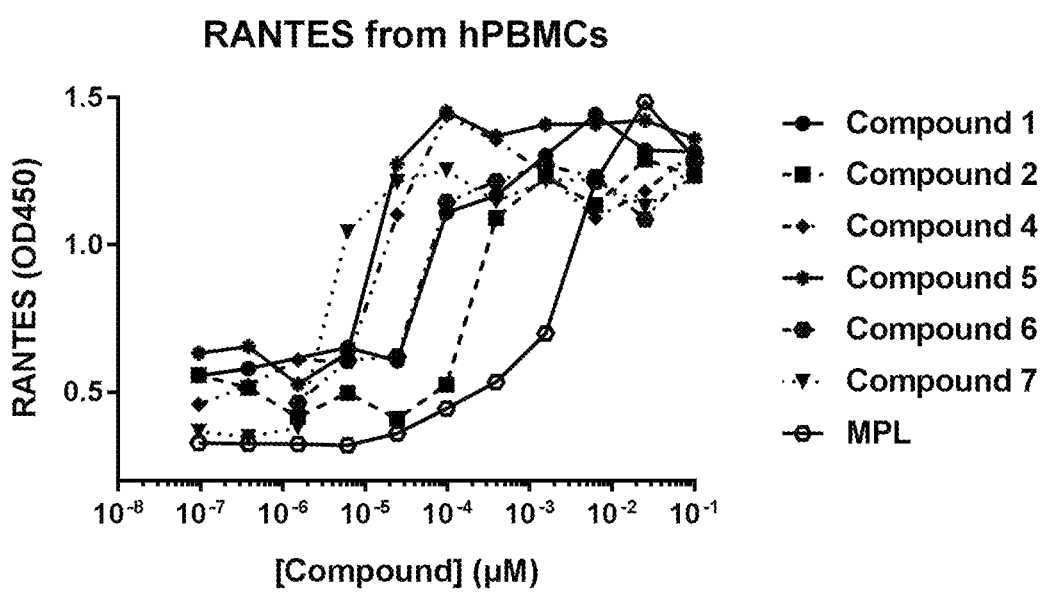
Figure 5C:
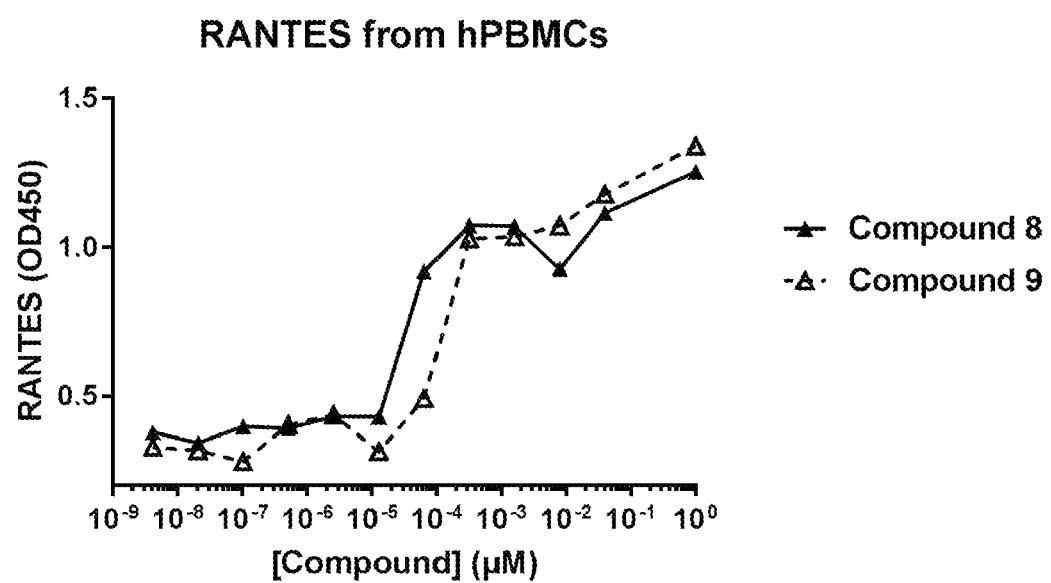
Figure 6A:
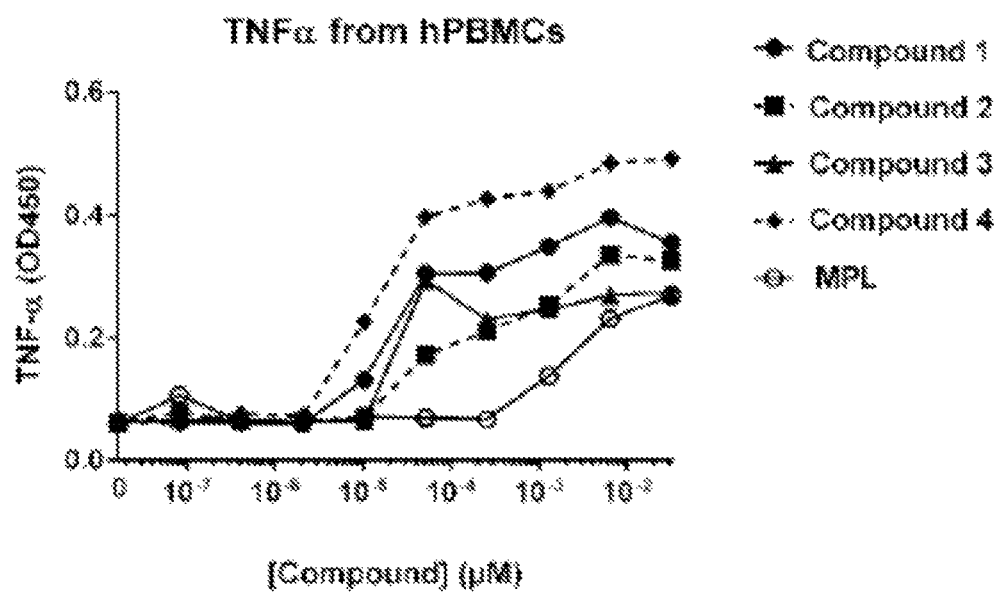
FIG. 6A (average of 3 donors), 6B (1 donor), and 6C (1 donor) show induction of TNFα cytokine from primary hPBMCs in response to compounds. Primary human peripheral blood mononuclear cells were isolated from the whole blood of three different donors using a Ficoll gradient. Cells were then subjected to treatment with increasing concentrations of the indicated compound for 18 hours and supernatants were analyzed for production of TNFα via ELISA.
Figure 6B:
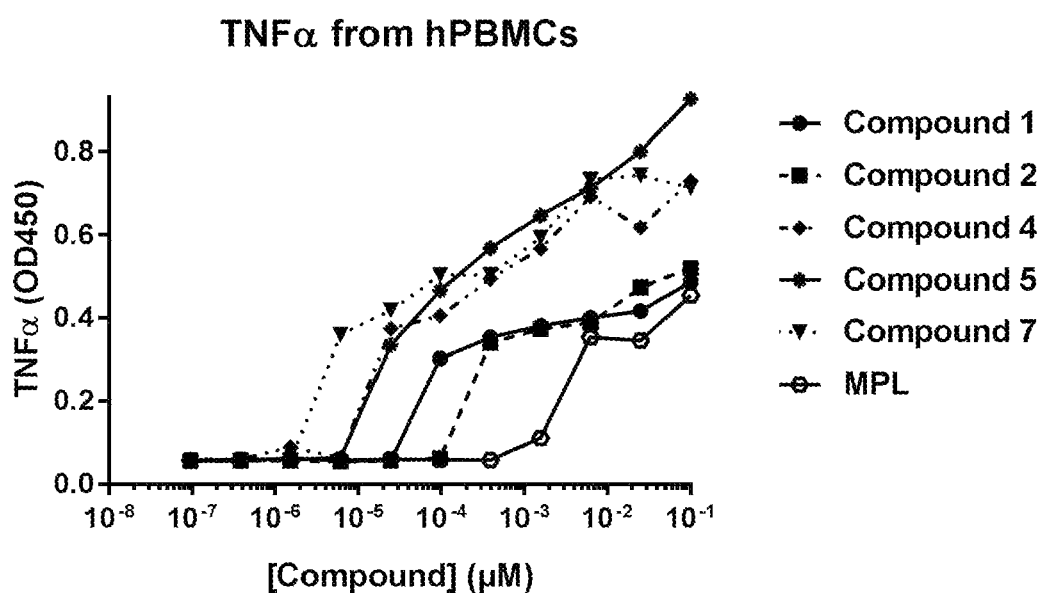
Figure 6C:
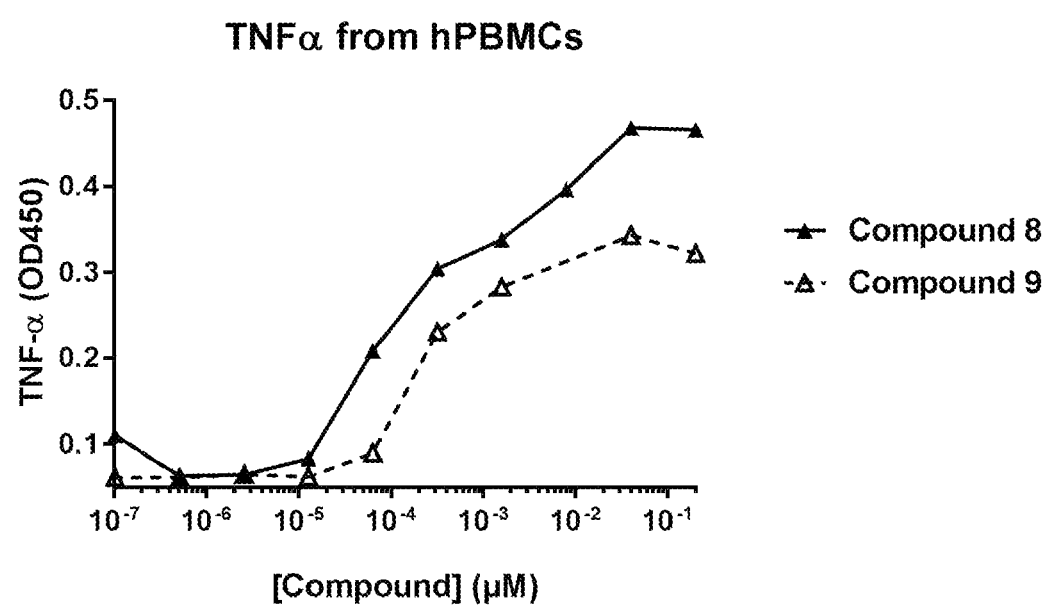

Induction of MIP-1β, RANTES or TNFα cytokine from primary hPBMCs. In addition to MIP-1β production from the MM6 cell line, MIP-1β, TNF-α and RANTES production was also examined from primary human peripheral mononuclear cells (PBMCs). Analysis of these cytokines are useful in assessing activation of MYD88-dependent (TNF-α) or TRIF-TRAM (RANTES) intracellular signaling pathways in response to compounds. PBMCs were obtained from different donors for bioassays and the compound-treated cellular supernatants were used for the three cytokine ELISAs. FIGS. 4A, 5A and 6A show the average response from three donors for compounds 1, 2, 3 and 4. FIGS. 4B, 5B and 6B show the response of compounds 1, 2, 4, 5, 6, and 7 in one donor, and FIGS. 4C, 5C and 6C show the response of compounds 8 and 9 in one donor. It should be noted that there was higher inter-donor variability for RANTES and TNF-α but less with MIP-1β; regardless all donors showed the same compound potency trends. All compounds were able to induce all three cytokines with roughly equivalent potency suggesting a MyD88/TRIF balanced cytokine skewing. Primary human peripheral blood mononuclear cells were isolated from the whole blood of donors using a Ficoll gradient. Cells were then subjected to treatment with increasing concentrations of the indicated compound (FIG. 4A-4C, FIGS. 5A-5C, and 6A-6C) for 18 hours and supernatants were analyzed for production of MIP-1β, RANTES or TNFα via ELISA. EC50 values for each compound in each hPBMC donor are shown in Tables 4a-4d. EC50 values were determined by fitting dose response curves to a non-linear 4-parameter equation.

TABLE 4a

| hPBMCs EC50 (pM) | | | | | |
| --- | --- | --- | --- | --- | --- |
| Compound 1 | Compound 2 | Compound 3 | Compound 4 | MPL | |
| RANTES | | | | | |
| 23.9 | 64.2 | 41.7 | 8.4 | 1415 | Donor 10 |
| 25.4 | 284.5 | 158.1 | 8.1 | 5155 | Donor 5 |
| 12.1 | 379.9 | 15.8 | 8.3 | 1925 | Donor 2 |
| 20.5 | 242.9 | 71.9 | 8.3 | 2831.7 | Average |
| 5.9 | 132.2 | 61.9 | 0.1 | 1656.0 | St Dev |
| MIP-1β | | | | | |
| 20.2 | 47.5 | 39.4 | 6.2 | 1259 | Donor 10 |
| 24.1 | 165.9 | 72.7 | 2.7 | 857.9 | Donor 5 |
| 19.8 | 75.5 | 31.4 | 5.9 | 756.5 | Donor 2 |

TABLE 4a-continued hPBMCs EC50 (pM)

| Compound 1 | Compound 2 | Compound 3 | Compound 4 | MPL | |
|---|---|---|---|---|---|
| 21.4 | 96.3 | 47.8 | 4.9 | 957.8 | Average |
| 1.9 | 50.5 | 17.9 | 1.6 | 217.0 | St Dev |

TABLE 4b* hPBMCs EC50 (pM)

| 1 | 2 | 4 | 5 | 6 | 7 | MPL | |
|---|---|---|---|---|---|---|---|
| | | | RANTES | | | | |
| 179.5 | 608.5 | 22.1 | 31.9 | 109.1 | 8.0 | 6737.0 | Donor 22 |
| 89.9 | 238.4 | 14.9 | 15.6 | 238.4 | 4.1 | 2232.0 | Donor 5 |
| 134.7 | 423.5 | 18.5 | 23.8 | 173.8 | 6.0 | 4484.5 | Average |
| 44.8 | 185.1 | 3.6 | 8.1 | 64.7 | 1.9 | 2252.5 | St Dev |
| | | | MIP-1β | | | | |
| 284.6 | 785.8 | 13.3 | 39.0 | 122.1 | 13.3 | 10260.0 | Donor 22 |
| 76.1 | 119.1 | 14.1 | 15.1 | 36.0 | 3.3 | 986.1 | Donor 5 |
| 180.3 | 452.5 | 13.7 | 27.0 | 79.1 | 8.3 | 5623.1 | Average |
| 104.3 | 333.4 | 0.4 | 12.0 | 43.0 | 5.0 | 4637.0 | St Dev |

*Numbers 1, 2, 4, 5, 6, and 7 refer to Compounds 1, 2, 4, 5, 6, and 7.

TABLE 4c hPBMCs EC50 (pM) RANTES

| Compound 8 | Compound 9 |
|---|---|
| 39.12 | 143.30 |

TABLE 4d hPBMCs EC50 (pM) MIP-1β

| Compound 8 | Compound 9 |
|---|---|
| 41.79 | 182.20 |

Vaccine Adjuvant Study.

Figure 7:
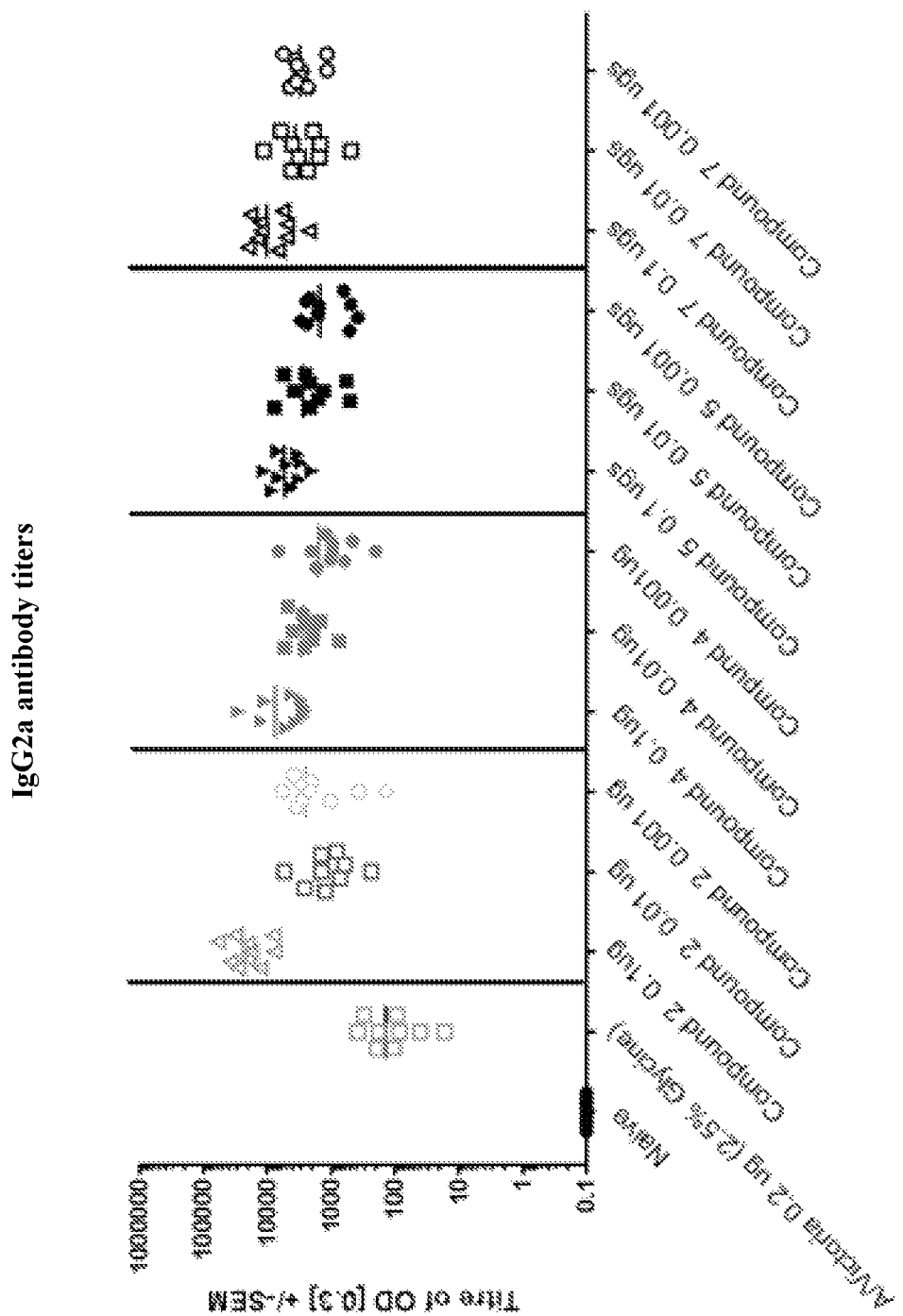
FIG. 7 shows influenza virus specific IgG2a antibody titers measured 14 days after intramuscular immunization of BALB/c mice with 0.2 μg of A/Victoria H3N2 influenza virus antigen, with or without compounds of the invention.

Compounds 2, 4, 5 and 7 were evaluated as vaccine adjuvant in a murine influenza virus vaccination model. 7-9 week old BALB/c mice (10 mice per group) were injected intramuscularly in a hind limb with the influenza virus antigen A/Victoria/210/2009-H3N2 (0.2 μg/mouse) with or without 0.1, 0.01 or 0.001 μg of compound 2, 4, 5 or 7 (formulated in 2% glycine). Fourteen days after a single immunization, animals were bled via the submandibular vein and serum was collected to assay for A/Victoria specific antibodies by ELISA assay (FIG. 7). Compounds 2, 4, 5 and 7 exhibited a dose dependent adjuvant effect by increasing flu-specific IgG2a antibody titers compared to antigen alone vaccine response.

Non-Specific Resistance (NSR) Study.

Figure 8:
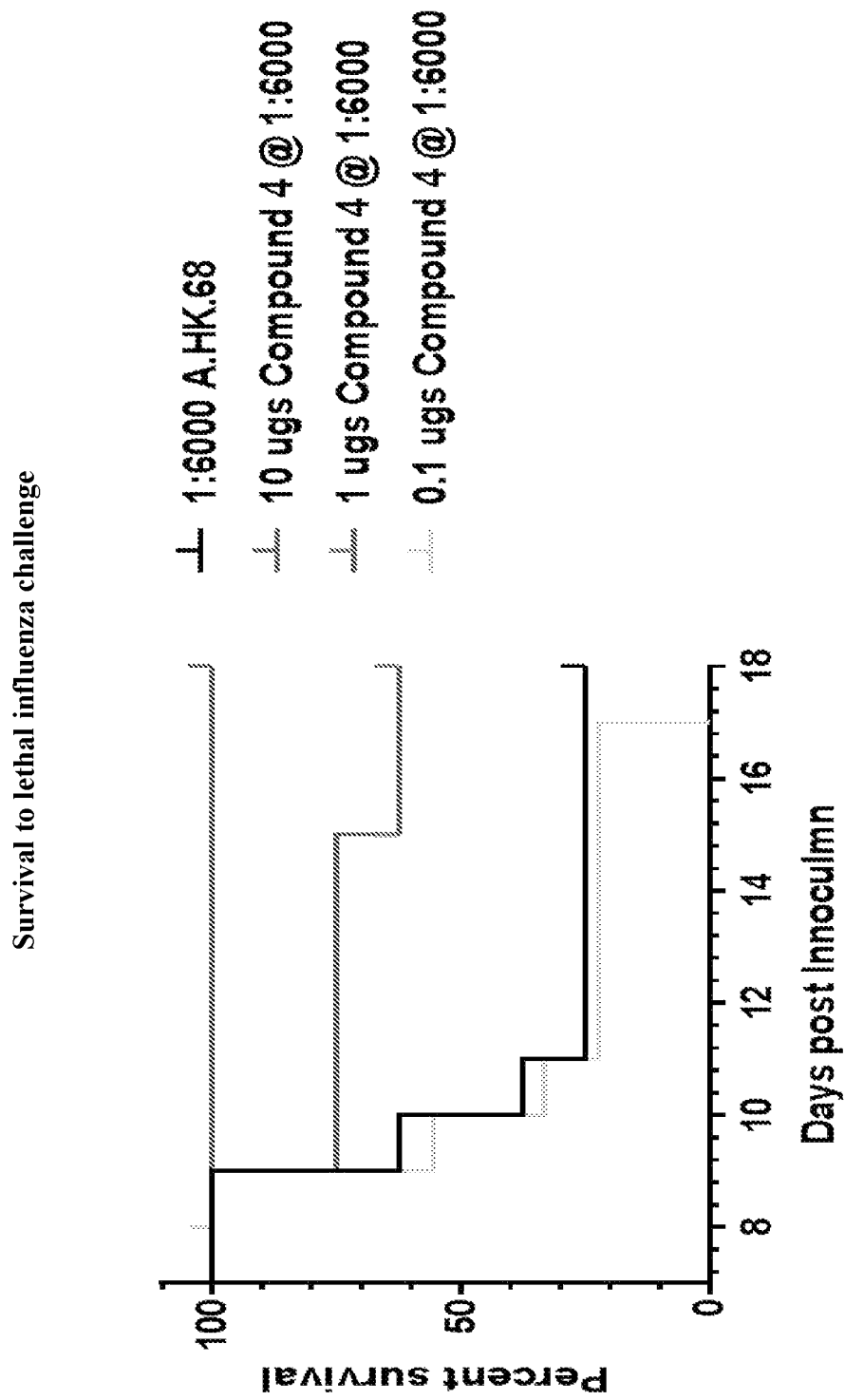
FIG. 8 shows survival results for 12-14 week old mice (BALB/c) dosed intranasally (10 μL/nare) with an aqueous formulation of 10, 1 and 0.1 g of Compound 4 on day −2. On Day 0, animals were challenged intranasally with a 1 LD50 of A/HK/68, a mouse adapted H3N2 human influenza virus. Compound 4 provided protection in a dose-dependent manner.
Figure 9:
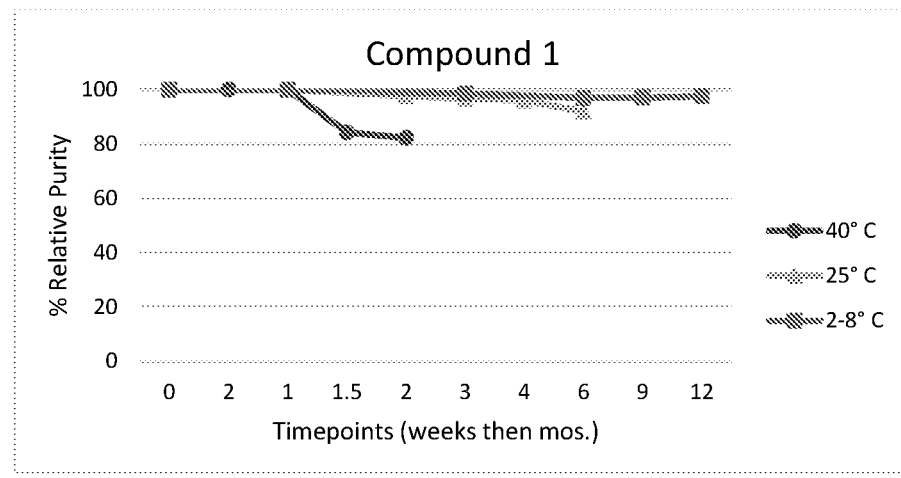
FIG. 9 shows a stability graph of Compound 1 formulated in 2.5% glycine, stored at 2-8° C., 25° C. and 40° C., and monitored for degradation by reverse phase-HPLC.

12-14 week old BALB/c mice (9 mice per group) were dosed intranasally (10 μL/nare) with an aqueous formulation of 10, 1 and 0.1 μg of compound 4 on day −2. On Day 0 animals were challenged with a 1 LD50 dose of influenza virus antigen A/HK/68 (a mouse adapted H3N2 human influenza virus). Weights, disease index and body temperatures were recorded daily for 20 days following challenge. Compound 4 provided strong non-specific protection against a lethal influenza virus challenge in a dose-dependent manner (FIG. 8).

Formulation.

The salted compound was accurately weighed into depyrogenated glass vials, and the required volume of aqueous vehicle added to attain the desired concentration. Vials were placed in a sonication bath (sonication bath temperature ≤45° C.) to assist solubility and reduce particle size to achieve sterile filtration without significant loss of compound. Once the solution appeared homogeneous, the particle size was periodically monitored by dynamic light scattering until the solution turned clear and the particle size was <200 mn, or the particle size no longer reduced with continued sonication. The formulation was filtered through a 0.22μ PVDF membrane filter into a depyrogenated glass vial and the resulting solution quantitated by RP-HPLC.

Stability Studies

Aqueous formulations of compounds 1, 2, 3, 4, 5 and 6 were aliquoted into small depyrogenated vials for stability evaluation at temperatures of 2°-8° C., 25° C., and 40° C. This mirrors ICH stability temperature guidelines, but humidity was not controlled. A vial was pulled for each time point/temperature and analyzed by reverse-phase-HPLC (FIGS. 9-14) according to the following schedule starting from 2 weeks to up to 12 months.

| Temperature | 2 Weeks | 1 Month | 2 Months | 3 Months | 4 Months | 6 Months | 9 Months | 12 Months |
|---|---|---|---|---|---|---|---|---|
| 40° C. | X | X | X | X | X | X | X | |
| 25° C. | | X | | X | | X | X | X |
| 2°-8° C. | | X | | X | | X | X | X |

Figure 10A:
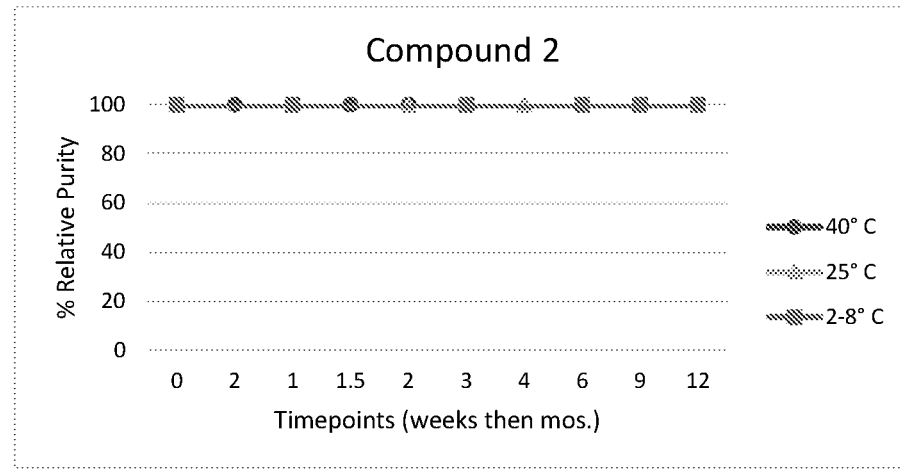
FIGS. 10A and 10B show stability graphs of Compound 2 formulated in 2.5% glycine and 2% glycerol, respectively, stored at 2-8° C., 25° C. and 40° C., and monitored for degradation by reverse phase-HPLC.
Figure 10B:
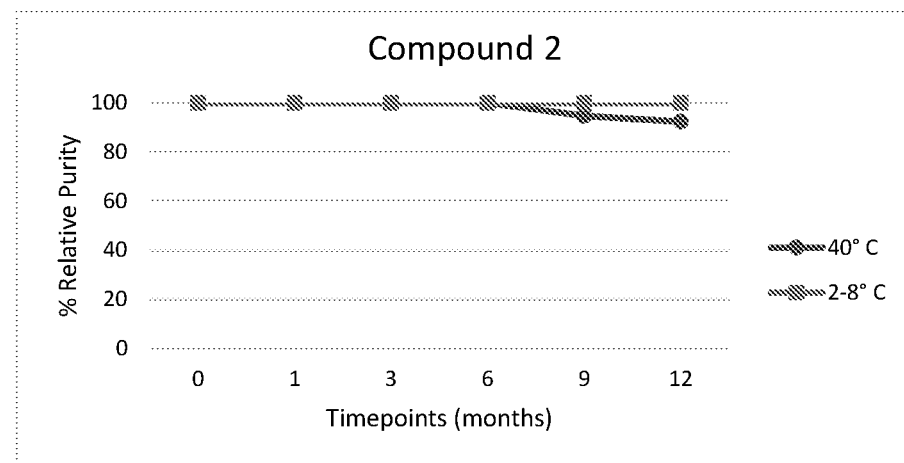
Figure 11:
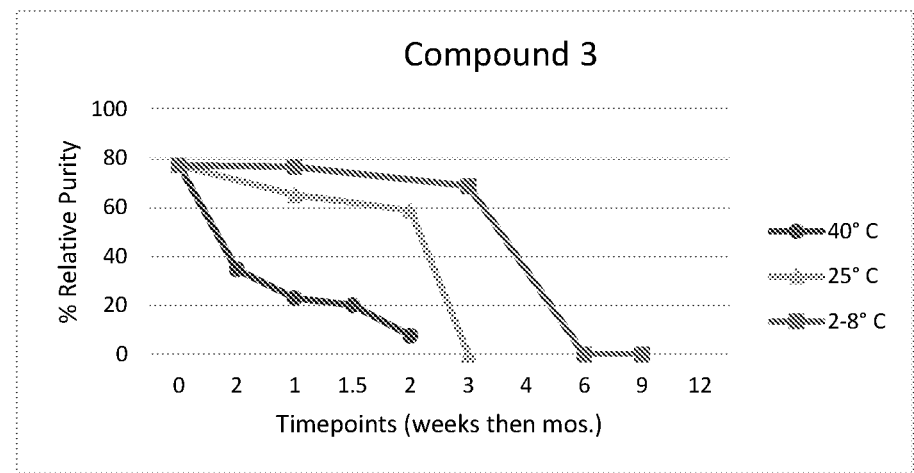
FIG. 11 shows a stability graph of Compound 3 formulated in 2.5% glycine, stored at 2-8° C., 25° C. and 40° C., and monitored for degradation by reverse phase-HPLC.
Figure 12:
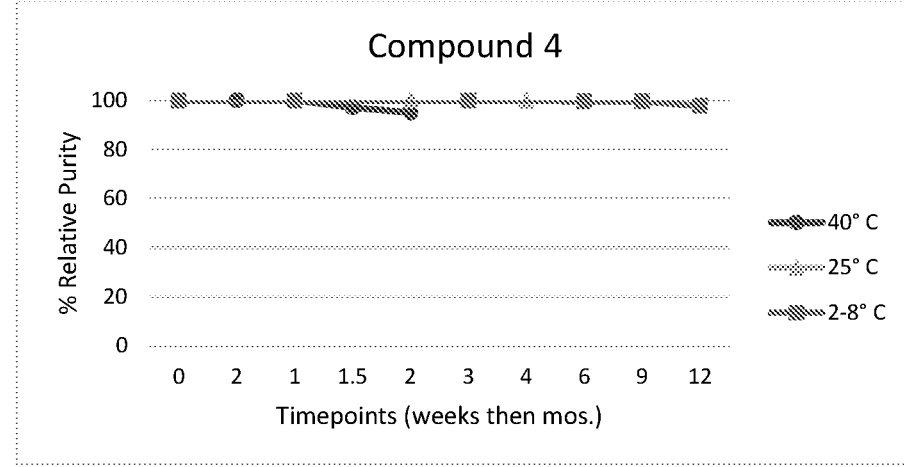
FIG. 12 shows a stability graph of Compound 4 formulated in 2.5% glycine, stored at 2-8° C., 25° C. and 40° C., and monitored for degradation by reverse phase-HPLC.
Figure 13:
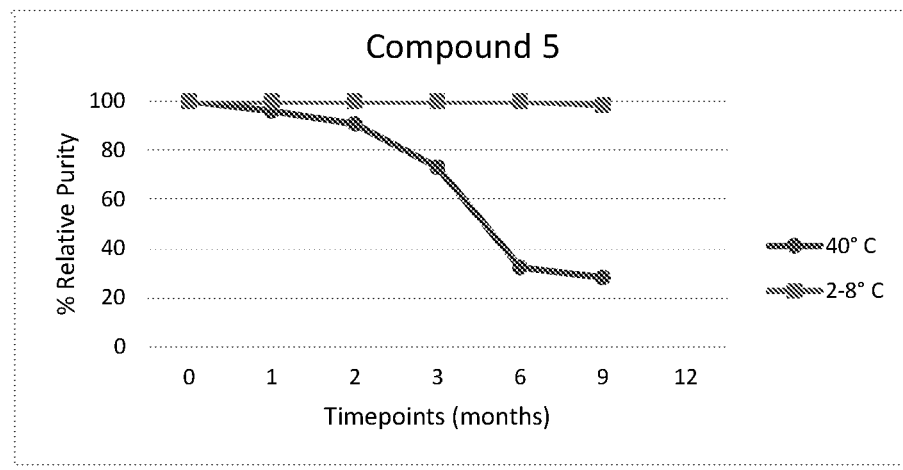
FIG. 13 shows a stability graph of Compound 5 formulated in 2% glycerol, stored at 2-8° C. 25° C. and 40° C., and monitored for degradation by reverse phase-HPLC.
Figure 14:
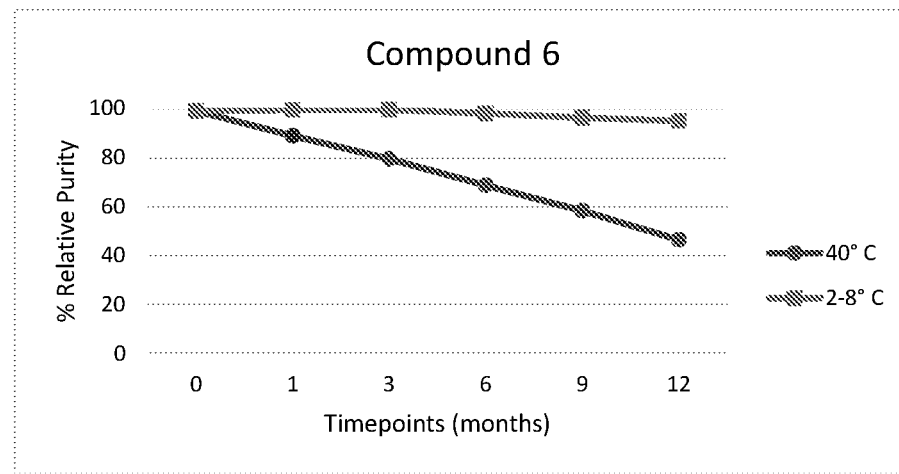
FIG. 14 shows a stability graph of Compound 6 formulated in 2% glycerol, stored at 2-8° C. 25° C. and 40° C., and monitored for degradation by reverse phase-HPLC.

Compound 1 showed good stability with no degradation until T=6 weeks at 40° C. Compound 2 showed exceptional stability with no degradation out to 8 weeks at 40° C. and 12 months at 25° C. when formulated in 2% glycine (FIG. 10A), and less than 10% degradation after 12 months at 40° C. when formulated in 2% glycerol (FIG. 10B). Compound 4 showed great stability with no degradation out to 8 weeks at 40° C. Excellent formulated stability is necessary for reliable safety, potency and reduction on cold chain reliance and increased product shelf-life.

For reasons of completeness, various aspects of the invention are set out in the following numbered clauses:

Clause 1. A compound of formula (II), or a pharmaceutically acceptable salt thereof,

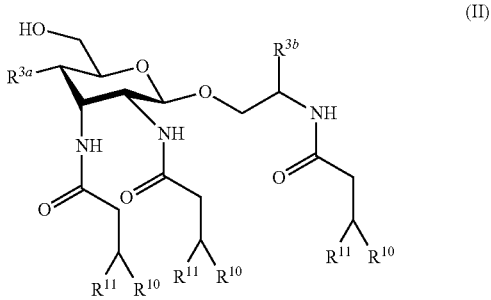

(II)

wherein:

$R^{10}$ is $C_{1-21}$alkyl;

$R^{11}$, at each occurrence, is independently —O—C(=O)$C_{1-15}$alkyl, —O—$C_{2-16}$alkyl, —O—C(=O)$C_{1-15}$alkylene-$Z^2$, or —$X^2$—$C_{2-16}$alkylene-$Z^2$;

$R^{3a}$, is —OP(O)(OH)$_2$, —OSO$_3$H, or —OCH$_2$—P(O)(OH)$_2$;

$R^{3b}$ is H, CO$_2$H, or an ester of the CO$_2$H; and $Z^2$, at each occurrence, is independently phenyl or a 5- to 6-membered heteroaryl, wherein $Z^2$ is optionally substituted with 1-5 substituents independently selected from $C_{1-4}$alkyl, $C_{1-4}$haloalkyl, —O$C_{1-4}$alkyl, —O$C_{1-4}$haloalkyl, cyano, and halogen.

Clause 2. A compound of formula (I), or a pharmaceutically acceptable salt thereof,

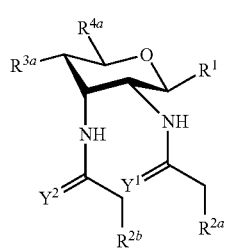

(I)

wherein:
$R^1$ is

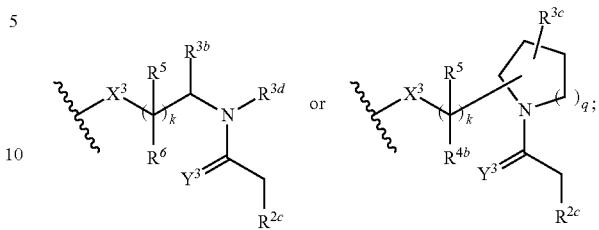

$R^{2a}$, $R^{2b}$, and $R^{2c}$ are each independently $C_{4-22}$alkyl, —$X^1$—$C_{3-21}$alkyl, —CH$_2$—$X^1$—$C_{2-20}$alkyl, or —CH($R^{10}$)($R^{11}$);

$R^{10}$, at each occurrence, is independently $C_{1-21}$alkyl, —$X^1$—$C_{2-20}$alkyl, or —CH$_2$—$X^1$—$C_{1-19}$alkyl;

$R^{11}$, at each occurrence, is independently $C_{3-17}$alkyl, —$X^2$—$C_{2-16}$alkyl, —CH$_2$—$X^2$—$C_{1-15}$alkyl, —$X^2$—C(=$Y^4$)$C_{1-15}$alkyl, —CH$_2$—C(=$Y^4$)$C_{1-15}$alkyl, —$X^2$—C(=$Y^4$)$C_{1-15}$alkylene-$Z^1$—$C_{1-15}$alkyl, —CH$_2$—C(=$Y^4$)$C_{1-15}$alkylene-$Z^1$—$C_{1-15}$alkyl, —$C_{3-17}$alkylene-$Z^1$—$C_{1-15}$alkyl, —$X^2$—$C_{2-16}$alkylene-$Z^1$—$C_{1-15}$alkyl, —CH$_2$—$X^2$—$C_{1-15}$alkylene-$Z^1$—$C_{1-15}$alkyl, —$X^2$—C(=$Y^4$)$C_{1-15}$alkylene-$Z^2$, or —$X^2$—$C_{2-16}$alkylene-$Z^2$;

$R^{3a}$, $R^{3b}$, and $R^{3c}$ are each independently CO$_2$H, —OSO$_3$H, —OP(O)(OH)$_2$, —$C_{1-6}$alkylene-CO$_2$H, —$C_{1-6}$alkylene-OSO$_3$H, —$C_{1-6}$alkylene-OP(O)(OH)$_2$, —O$C_{1-6}$alkylene-P(O)(OH)$_2$, —$C_{1-6}$alkylene-P(O)(OH)$_2$, —$C_{1-6}$haloalkylene-P(O)(OH)$_2$, H, or an ester of the CO$_2$H, —OSO$_3$H, —OP(O)(OH)$_2$, —$C_{1-6}$alkylene-CO$_2$H, —$C_{1-6}$ alkylene-OSO$_3$H, —$C_{1-6}$alkylene-OP(O)(OH)$_2$, —O$C_{1-6}$alkylene-P(O)(OH)$_2$, —$C_{1-6}$alkylene-P(O)(OH)$_2$, or —$C_{1-6}$haloalkylene-P(O)(OH)$_2$;

$R^{3d}$ is CO$_2$H, —SO$_3$H, —P(O)(OH)$_2$, —$C_{1-6}$alkylene-CO$_2$H, —$C_{1-6}$alkylene-OSO$_3$H, —$C_{1-6}$alkylene-OP(O)(OH)$_2$, —O$C_{1-6}$alkylene-P(O)(OH)$_2$, —$C_{1-6}$alkylene-P(O)(OH)$_2$, —$C_{1-6}$haloalkylene-P(O)(OH)$_2$, H, $C_{1-6}$alkyl, $C_{1-6}$haloalkyl, $C_{3-8}$cycloalkyl, or an ester of the CO$_2$H, —OSO$_3$H, —OP(O)(OH)$_2$, —$C_{1-6}$alkylene-CO$_2$H, —$C_{1-6}$ alkylene-OSO$_3$H, —$C_{1-6}$alkylene-OP(O)(OH)$_2$, —O$C_{1-6}$alkylene-P(O)(OH)$_2$, —$C_{1-6}$alkylene-P(O)(OH)$_2$, or —$C_{1-6}$haloalkylene-P(O)(OH)$_2$;

$R^{4a}$ is CO$_2$H, CH$_2$OSO$_3$H, CH$_2$CO$_2$H, CH$_2$P(O)(OH)$_2$, CH$_2$H, H, or an ester of the CO$_2$H, CH$_2$SO$_3$H, CH$_2$CO$_2$H, or CH$_2$P(O)(OH)$_2$;

$R^{4b}$, at each occurrence, is independently CO$_2$H, CH$_2$OSO$_3$H, CH$_2$CO$_2$H, CH$_2$P(O)(OH)$_2$, CH$_2$OH, H, or an ester of the CO$_2$H, CH$_2$SO$_3$H, CH$_2$CO$_2$H, or CH$_2$P(O)(OH)$_2$;

$R^5$ and $R^6$, at each occurrence, are independently H, $C_{1-6}$alkyl, $C_{1-6}$haloalkyl, —O—$C_{1-6}$alkyl, or —$C_{1-6}$alkylene-OH;

$X^1$ and $X^2$, at each occurrence, are independently O, S, or NH;

$X^3$ is O, S, NH, or CH$_2$;

$Y^1$, $Y^2$, and $Y^3$ are independently O, S, NH, or H$_2$;

$Y^4$, at each occurrence, is independently O, S, or NH;

$Z^1$, at each occurrence, is independently phenylene or 5- to 6-membered heteroarylene, the phenylene and heteroarylene being optionally substituted with 1-4 substituents independently selected from $C_{1-4}$alkyl, $C_{1-4}$haloalkyl, —O$C_{1-4}$alkyl, —O$C_{1-4}$haloalkyl, cyano, and halogen;

$Z^2$, at each occurrence, is independently phenyl or a 5- to 6-membered heteroaryl, wherein $Z^2$ is optionally substituted with 1-5 substituents independently selected from $C_{1-4}$alkyl, $C_{1-4}$haloalkyl, —$OC_{1-4}$alkyl, —$OC_{1-4}$haloalkyl, cyano, and halogen; and k and q are each independently an integer from 0-4.

Clause 3. A compound of formula (I), or a pharmaceutically acceptable salt thereof,

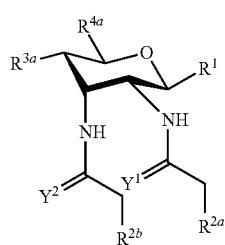

(I)

wherein:
$R^1$ is

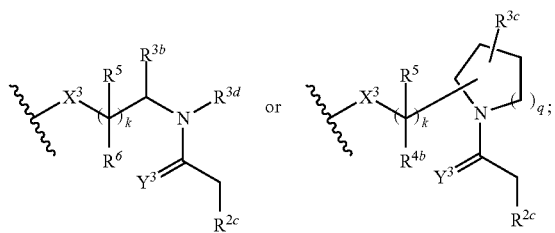

$R^{2a}$, $R^{2b}$, and $R^{2c}$ are each independently $C_{4-22}$alkyl, —$X^1$—$C_{3-21}$alkyl, —$CH_2$—$X^1$—$C_{2-20}$alkyl, or —$CH(R^{10})(R^{11})$;
$R^{10}$ is $C_{1-21}$alkyl, —$X^1$—$C_{2-20}$alkyl, or —$CH_2$—$X^1$—$C_{1-19}$alkyl;
$R^{11}$ is $C_{3-17}$alkyl, —$X^2$—$C_{2-16}$alkyl, —$CH_2$—$X^2$—$C_{1-15}$alkyl, —$X^2$—$C(=Y^4)C_{1-15}$alkyl, —$CH_2$—$C(=Y^4)$ $C_{1-15}$alkyl, —$X^2$—$C(=Y^4)C_{1-15}$alkylene-$Z^1$—$C_{1-15}$alkyl, —$CH_2$—$C(=Y^4)C_{1-15}$alkylene-$Z^1$—$C_{1-15}$alkyl, —$C_{3-17}$alkylene-$Z^1$—$C_{1-15}$alkyl, —$X^2$—$C_{2-16}$alkylene-$Z^1$—$C_{1-15}$alkyl, or —$CH_2$—$X^2$—$C_{1-15}$alkylene-$Z^1$—$C_{1-15}$alkyl;
$R^{3a}$, $R^{3b}$, and $R^{3c}$ are each independently $CO_2H$, —$OSO_3H$, —$OP(O)(OH)_2$, —$C_{1-6}$alkylene-$CO_2H$, —$C_{1-6}$alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, —$C_{1-6}$haloalkylene-$P(O)(OH)_2$, H, or an ester of the $CO_2H$, —$OSO_3H$, —$OP(O)(OH)_2$, —$C_{1-6}$alkylene-$CO_2H$, —$C_{1-6}$ alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, or —$C_{1-6}$haloalkylene-$P(O)(OH)_2$;
$R^{3d}$ is $CO_2H$, —$SO_3H$, —$P(O)(OH)_2$, —$C_{1-6}$alkylene-$CO_2H$, —$C_{1-6}$alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, —$C_{1-6}$haloalkylene-$P(O)(OH)_2$, H, $C_{1-6}$alkyl, $C_{1-6}$haloalkyl, $C_{3-8}$cycloalkyl, or an ester of the $CO_2H$, —$OSO_3H$, —$OP(O)(OH)_2$, —$C_{1-6}$alkylene-$CO_2H$, —$C_{1-6}$ alkylene-$OSO_3H$, —$C_{1-6}$alkylene-$OP(O)(OH)_2$, —$OC_{1-6}$alkylene-$P(O)(OH)_2$, —$C_{1-6}$alkylene-$P(O)(OH)_2$, or —$C_{1-6}$haloalkylene-$P(O)(OH)_2$;
$R^{4a}$ and $R^{4b}$ are each independently $CO_2H$, $CH_2OSO_3H$, $CH_2CO_2H$, $CH_2P(O)(OH)_2$, $CH_2OH$, H, or an ester of the $CO_2H$, $CH_2SO_3H$, $CH_2CO_2H$, or $CH_2P(O)(OH)_2$;

$R^5$ and $R^6$, at each occurrence, are independently H, $C_{1-6}$alkyl, $C_{1-6}$haloalkyl, —O—$C_{1-6}$alkyl, or —$C_{1-6}$alkylene-OH;
$X^1$ and $X^2$ are independently O, S, or NH;
$X^3$ is O, S, NH, or $CH_2$;
$Y^1$, $Y^2$, and $Y^3$ are independently O, S, NH, or $H_2$;
$Y^4$ is O, S, or NH;
$Z^1$ is phenylene or 5- to 6-membered heteroarylene, the phenylene and heteroarylene being optionally substituted with 1-4 substituents independently selected from $C_{1-4}$alkyl, $C_{1-4}$haloalkyl, —$OC_{1-4}$alkyl, —$OC_{1-4}$haloalkyl, cyano, and halogen; and
k and q are each independently an integer from 0-4.

Clause 4. The compound of clause 2 or 3, or a pharmaceutically acceptable salt thereof, wherein
$R^{2a}$, $R^{2b}$, and $R^{2c}$ are each independently —$CH(R^{10})(R^{11})$.

Clause 5. The compound of any of clauses 1-4, or a pharmaceutically acceptable salt thereof, wherein at least one occurrence of $R^{10}$ is $C_{1-19}$alkyl.

Clause 6. The compound of any of clauses 1-5, or a pharmaceutically acceptable salt thereof, wherein at least one occurrence of $R^{10}$ is $C_{3-21}$alkyl.

Clause 7. The compound of any of clauses 1-6, or a pharmaceutically acceptable salt thereof, wherein at least one occurrence of $R^{11}$ is —$C(=O)C_{1-15}$alkyl.

Clause 8. The compound of any of clauses 1-6, or a pharmaceutically acceptable salt thereof, wherein at least one occurrence of $R^{11}$ is —O—$C(=O)C_{1-15}$alkylene-$Z^2$.

Clause 9. The compound of any of clauses 1-6, or a pharmaceutically acceptable salt thereof, wherein at least one occurrence of $R^{11}$ is —O—$C_{2-6}$alkylene-$Z^2$.

Clause 10. The compound of any of clauses 1-6, or a pharmaceutically acceptable salt thereof, wherein at least one occurrence of $R^{11}$ is —O—$C_{2-6}$alkyl.

Clause 11. The compound of any of clauses 1-5 or 7-10, or a pharmaceutically acceptable salt thereof, wherein $R^{11}$ is $C_{1-19}$alkyl.

Clause 12. The compound of any of clauses 1-4 or 6-10, or a pharmaceutically acceptable salt thereof, wherein $R^{11}$ is $C_{3-21}$alkyl.

Clause 13. The compound of any of clauses 2-4 or 7-10, or a pharmaceutically acceptable salt thereof, wherein $R^{11}$ is —$X^1$—$C_{2-20}$alkyl.

Clause 14. The compound of any of clauses 2-4 or 7-10, or a pharmaceutically acceptable salt thereof, wherein $R^{10}$ is —$CH_2$—$X^1$—$C_{1-19}$alkyl.

Clause 15. The compound of any of clauses 2-6 or 11-14, or a pharmaceutically acceptable salt thereof, wherein $R^{11}$ is —$X^2$—$C(=Y^4)C_{1-15}$alkyl.

Clause 16. The compound of any of clauses 2-6 or 11-14, or a pharmaceutically acceptable salt thereof, wherein $R^{11}$ is —$X^2$—$C(=Y^4)C_{1-15}$alkylene-$Z^1$—$C_{1-15}$alkyl.

Clause 17. The compound of any of clauses 2-6 or 11-14, or a pharmaceutically acceptable salt thereof, wherein $R^{11}$ is —$X^2$—$C(=Y^4)C_1$alkylene-$Z^2$.

Clause 18. The compound of any of clauses 2-6 or 11-14, or a pharmaceutically acceptable salt thereof, wherein $R^{11}$ is —$X^2$—$C_{2-16}$alkylene-$Z^2$.

Clause 19. The compound of any of clauses 2-6 or 11-18, or a pharmaceutically acceptable salt thereof, wherein $Y^4$ is O.

Clause 20. The compound of any of clauses 2-6 or 11-14, or a pharmaceutically acceptable salt thereof, wherein $R^{11}$ is —$X^2$—$C_{2-16}$alkyl.

Clause 21. The compound of any of clauses 2-6 or 11-14, or a pharmaceutically acceptable salt thereof, wherein $R^{11}$ is —$CH_2$—$X^2$—$C_{1-15}$alkyl.

Clause 22. The compound of any of clauses 2-6 or 11-21, or a pharmaceutically acceptable salt thereof, wherein $X^2$ is O.

Clause 23. The compound of any of clauses 2-6 or 11-22, or a pharmaceutically acceptable salt thereof, wherein $Y^1$, $Y^2$, and $Y^3$ are O.

Clause 24. The compound of any of clauses 2-23, or a pharmaceutically acceptable salt thereof, wherein $X^3$ is O.

Clause 25. The compound of any of clauses 1-24, or a pharmaceutically acceptable salt thereof, wherein $R^{3a}$ is —OP(O)(OH)$_2$.

Clause 26. The compound of any of clauses 1-24, or a pharmaceutically acceptable salt thereof, wherein $R^{3a}$ is —OSO$_3$H.

Clause 27. The compound of any of clauses 1-24, or a pharmaceutically acceptable salt thereof, wherein $R^{3a}$ is —OCH$_2$P(O)(OH)$_2$.

Clause 28. The compound of any of clauses 2-27, or a pharmaceutically acceptable salt thereof, wherein $R^{4a}$ is CH$_2$OH.

Clause 29. The compound of any of clauses 2-28, or a pharmaceutically acceptable salt thereof, wherein
$R^1$ is $R^{2c}$

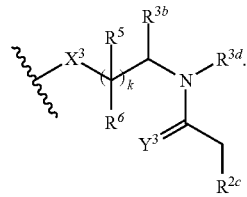

Clause 30. The compound of clause 29, or a pharmaceutically acceptable salt thereof, wherein
k is 1;
$R^{3b}$ is hydrogen or COOH, or an ester thereof, and
$R^{3d}$, $R^5$, and $R^6$ are each hydrogen.

Clause 31. The compound of any of clauses 2-28, or a pharmaceutically acceptable salt thereof, wherein
$R^1$ is

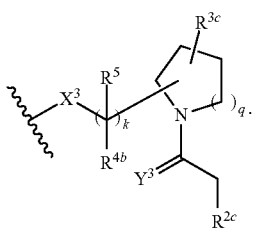

Clause 32. The compound of clause 1, selected from the group consisting of

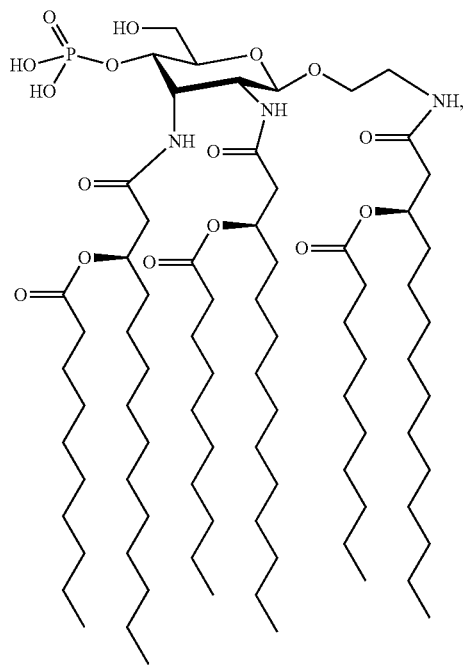

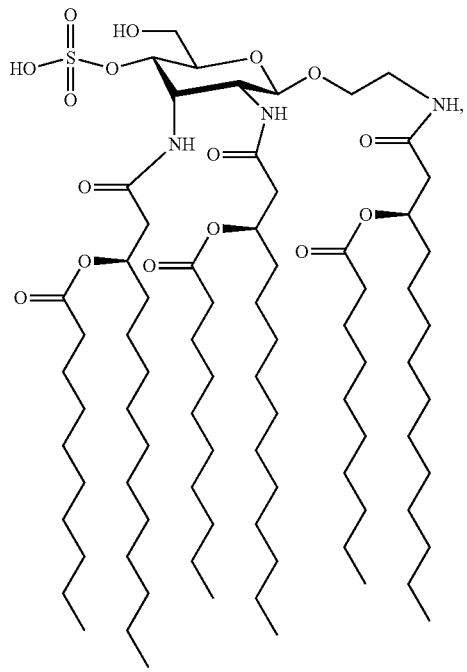

85
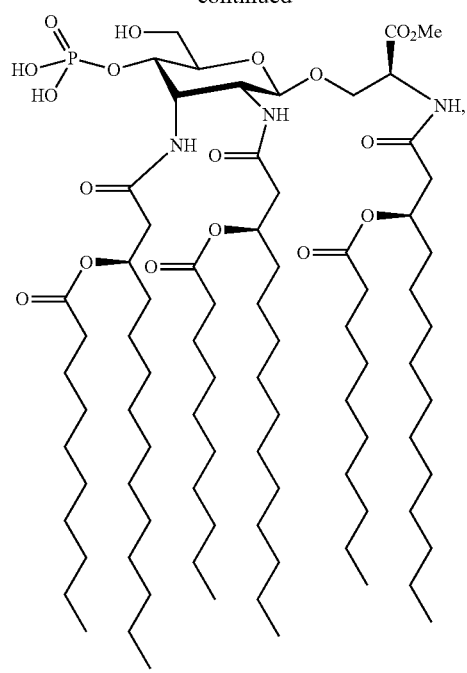
86
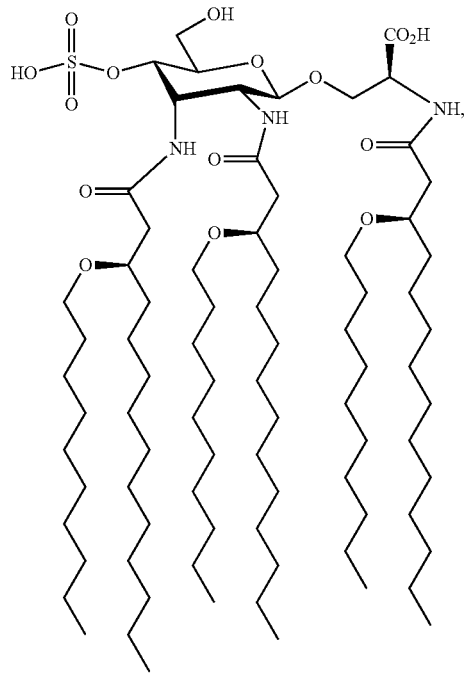
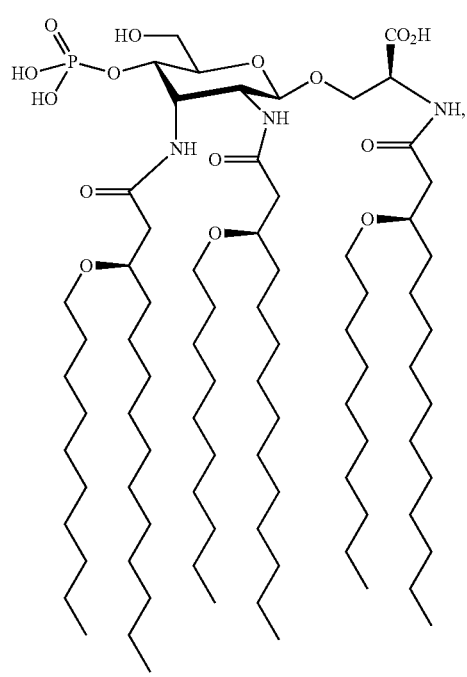
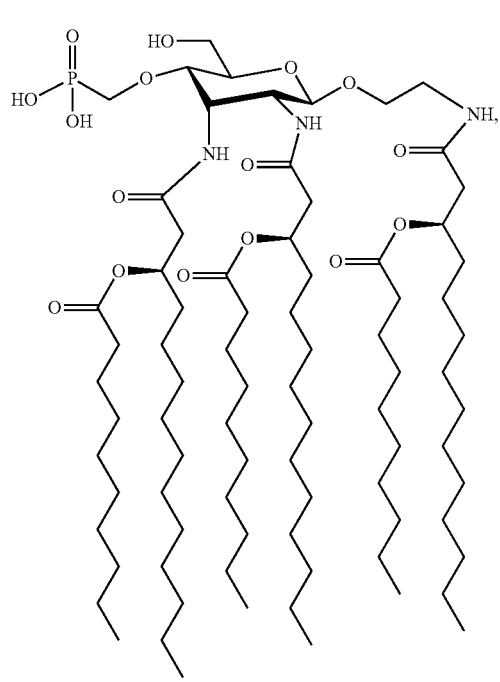

87
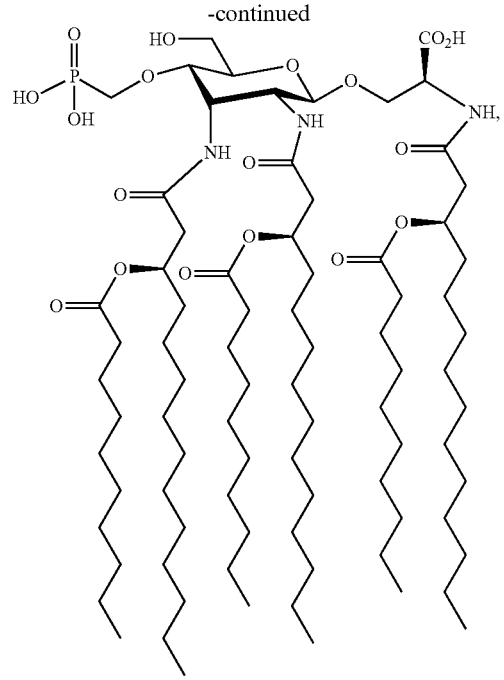
88
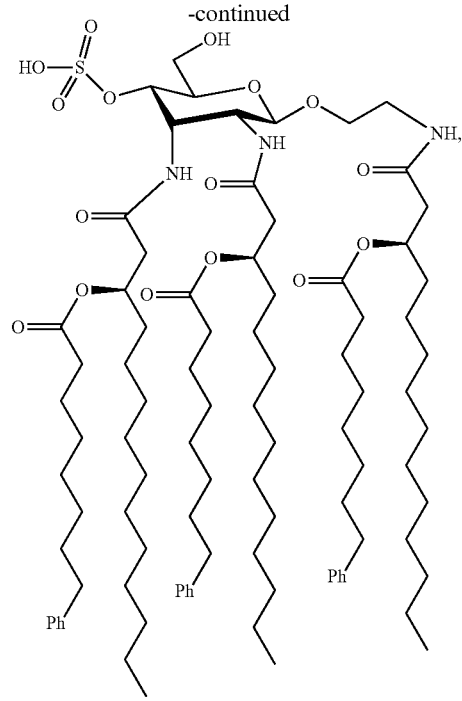
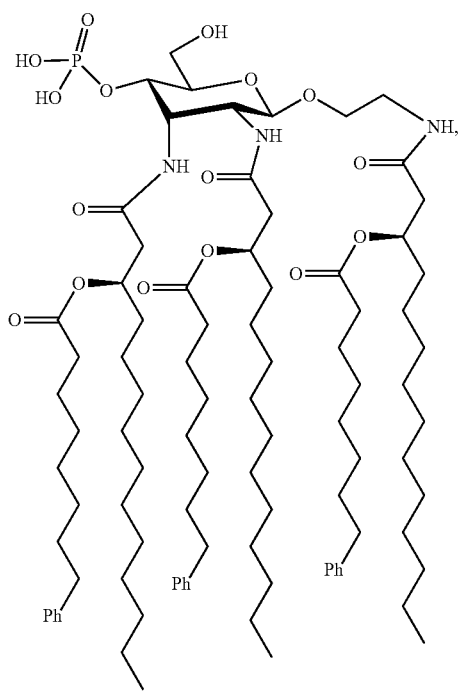
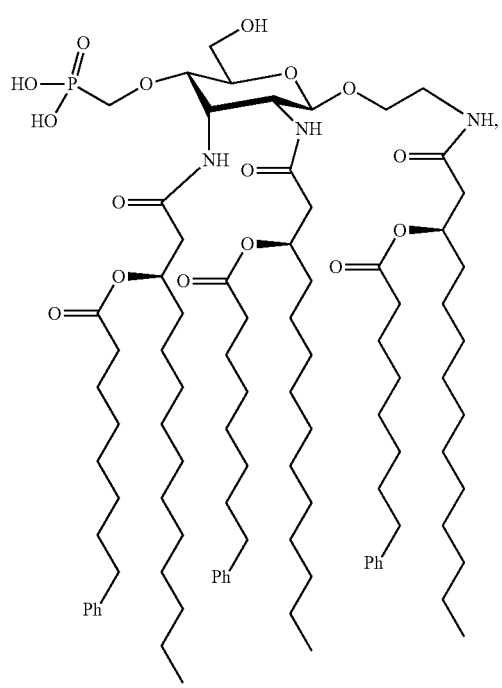

89

-continued

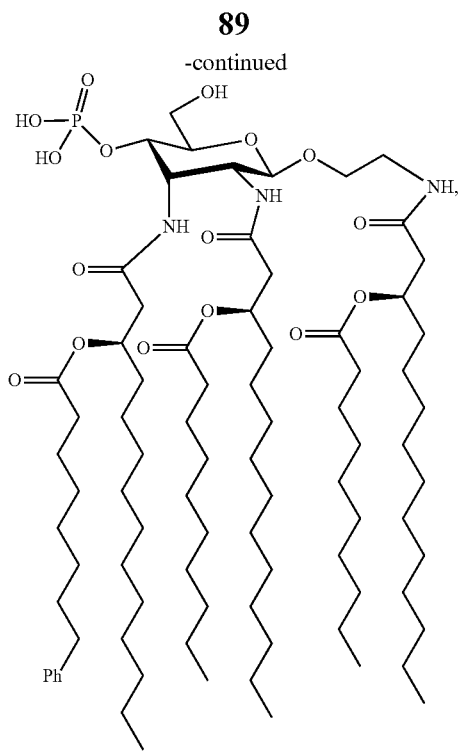

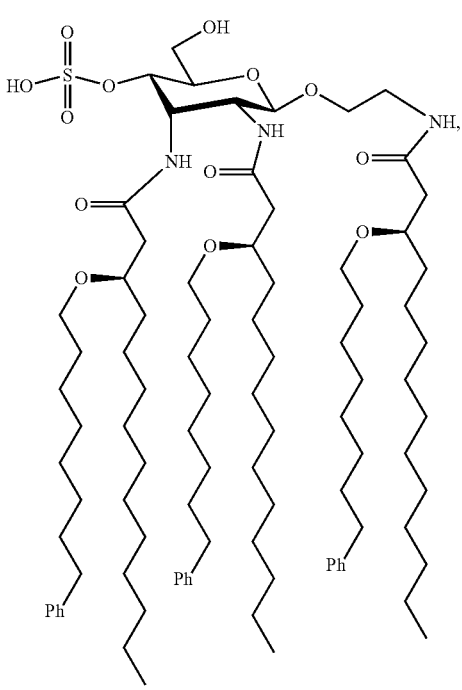

90

-continued

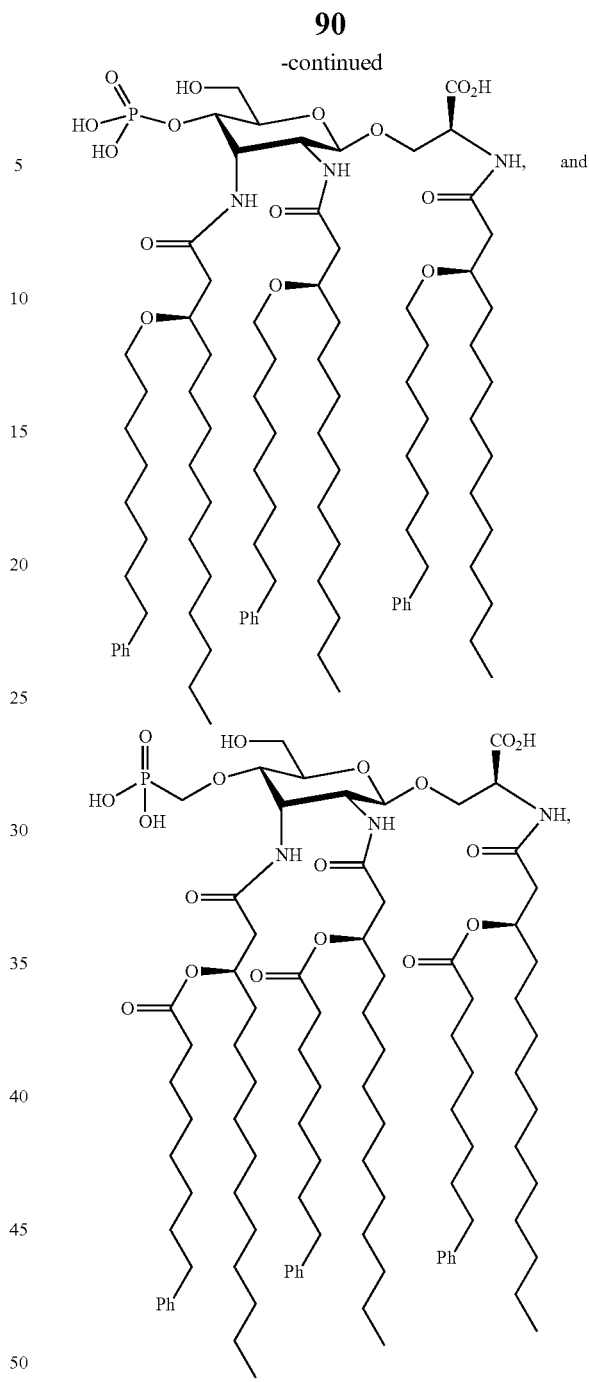

or a pharmaceutically acceptable salt thereof.

Clause 33. The compound of any of clauses 1-32, or a pharmaceutically acceptable salt thereof, wherein the compound is a TLR4 antagonist.

Clause 34. The compound of any of clauses 1-32, or a pharmaceutically acceptable salt thereof, wherein the compound is a TLR4 agonist.

Clause 35. A pharmaceutical composition comprising the compound of any of clauses 1-34, or a pharmaceutically acceptable salt thereof, and a pharmaceutically acceptable carrier.

Clause 36. The pharmaceutical composition of clause 35, further comprising an antigen.

Clause 37. The pharmaceutical composition of clause 36 comprising an immunogenic quantity of the antigen.

Clause 38. The pharmaceutical composition of clause 36 or 37, wherein the antigen is derived from a bacterium, virus, fungus, prion, neoplasm, autoantigen, animal, plant, recombinant or synthetic material.

Clause 39. The pharmaceutical composition of any of clauses 36-38, wherein the antigen is in the form of a polypeptide.

Clause 40. The pharmaceutical composition of any of clauses 36-38, wherein the antigen is an allergen.

Clause 41. The pharmaceutical composition of any of clauses 35-40, wherein the composition is a vaccine.

Clause 42. The pharmaceutical composition of clause 35 further comprising an additional therapeutic agent selected from a chemotherapeutic agent and an immune modulatory agent such as an immune checkpoint inhibitor or tumor phagocytosis-inducing agent.

Clause 43. The pharmaceutical composition of any of clauses 35-42, wherein the composition is a TH1-inducing adjuvant.

Clause 44. The pharmaceutical composition of any of clauses 35-43, wherein the composition is in the form of an aqueous solution, an emulsion, liposomes, a nanoparticle, adsorbed to an inorganic or organic substrate, a gel, a capsule, a lozenge or a tablet.

Clause 45. A method of eliciting or enhancing, or modifying an immune response in a subject comprising administering to a subject in need thereof a therapeutically effective amount of the compound of any of clauses 1-34, or a pharmaceutically acceptable salt thereof, or the pharmaceutical composition of any of clauses 35-44.

Clause 46. The method of clause 45, wherein the immune response treats a cancer in the subject.

Clause 47. The method of clause 45, wherein the immune response treats an infectious disease in the subject.

Clause 48. The method of clause 47, wherein the infectious disease is a bacterial, viral, fungal or prion infection.

Clause 49. The method of clause 45, wherein the immune response treats an allergy in the subject.

Clause 50. A method of treating, preventing, or reducing the susceptibility to cancer in a subject comprising administering to a subject in need thereof a therapeutically effective amount of the compound of any of clauses 1-34, or a pharmaceutically acceptable salt thereof, or the pharmaceutical composition of any of clauses 35-44.

Clause 51. A method of treating, preventing, or reducing the susceptibility to an infectious disease in a subject comprising administering to a subject in need thereof a therapeutically effective amount of the compound of any of clauses 1-34, or a pharmaceutically acceptable salt thereof, or the pharmaceutical composition of any of clauses 35-44.

Clause 52. The method of clause 51, wherein the infectious disease is a bacterial, viral, fungal or prion infection.

Clause 53. A method of treating, preventing, or reducing the susceptibility to an allergy in a subject comprising administering to a subject in need thereof a therapeutically effective amount of the compound of any of clauses 1-34, or a pharmaceutically acceptable salt thereof, or the pharmaceutical composition of any of clauses 35-44.

Clause 54. A method of treating, preventing, or reducing the susceptibility to an autoimmune condition in a subject comprising administering to a subject in need thereof a therapeutically effective amount of the compound of any of clauses 1-34, or a pharmaceutically acceptable salt thereof, or the pharmaceutical composition of any of clauses 35-44.

Clause 55. A method of treating, preventing, or reducing the susceptibility in a subject to bacterial, viral, prion infection, autoimmunity, cancer or allergy comprising administering to a subject in need thereof a therapeutically effective amount of the compound of any of clauses 1-34, or a pharmaceutically acceptable salt thereof, or the pharmaceutical composition of any of clauses 35-44.

Clause 56. The method of any of clauses 45-55, wherein the administering to the subject is by intramuscular, intradermal, subcutaneous, topical, intravenous or mucosal administration.

Clause 57. The method of any of clauses 45-56, further comprising administering to the subject a therapeutically effective amount of radiation therapy or an additional therapeutic agent selected from a chemotherapeutic agent and an immune modulatory agent such as an immune checkpoint inhibitor or tumor phagocytosis-inducing agent.

Clause 58. The method of any of clauses 45-57, further comprising administering to the subject an immunogenic quantity of an antigen.

Clause 59. The method according to any of clauses 45-58, wherein the method produces an IgA immune response.

Clause 60. The method according to any of clauses 45-59, wherein the method produces an IgG immune response.

Clause 61. A method of treating or preventing or reducing the susceptibility to autoimmunity, allergy, ischemia reperfusion or sepsis in a subject comprising administering to a subject in need thereof a therapeutically effective amount of the compound of any of clauses 1-34, or a pharmaceutically acceptable salt thereof, or the pharmaceutical composition of clauses 35-44.

Clause 62. A method of treating or preventing or reducing the severity of epileptic seizures comprising administering to a subject in need thereof a therapeutically effective amount of the compound of any of clauses 1-34, or a pharmaceutically acceptable salt thereof, or the pharmaceutical composition of clauses 35-44.

Clause 63. A method of treating or preventing or reducing the susceptibility to ocular diseases such as macular degeneration, ocular hypertension, and ocular infection comprising administering to a subject in need thereof a therapeutically effective amount of the compound of any of clauses 1-34, or a pharmaceutically acceptable salt thereof, or the pharmaceutical composition of clauses 35-44.

Clause 64. A kit comprising: the compound of any of clauses 1-34, or a pharmaceutically acceptable salt thereof, or the pharmaceutical composition of any of clauses 35-44; and instructions for use of the pharmaceutical composition.

The foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

We claim:

1. A compound of formula (I), or a pharmaceutically acceptable salt thereof,

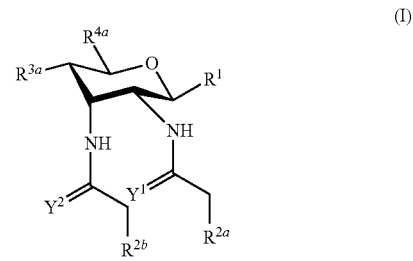

wherein:

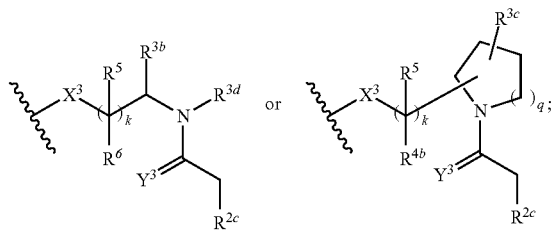

R$^1$ is

R$^{2a}$, R$^{2b}$, and R$^{2c}$ are each independently C$_{4-22}$ alkyl, —X$^1$—C$_{3-21}$ alkyl, —CH$_2$—X$^1$—C$_{2-20}$ alkyl, or —CH(R$^{10}$)(R$^{11}$);

R$^{10}$, at each occurrence, is independently C$_{1-21}$ alkyl, —X$^1$—C$_{2-20}$ alkyl, or —CH$_2$—X$^1$—C$_{1-19}$ alkyl;

R$^{11}$, at each occurrence, is independently C$_{3-17}$ alkyl, —X$^2$—C$_{2-16}$ alkyl, —CH$_2$—X$^2$—C$_{1-15}$ alkyl, —X$^2$—C(=Y$^4$)C$_{1-15}$ alkyl, —CH$_2$—C(=Y$^4$)C$_{1-15}$ alkyl, —X$^2$—C(=Y$^4$)C$_{1-15}$ alkylene-Z$^1$—C$_{1-15}$ alkyl, —CH$_2$—C(=Y$^4$)C$_{1-15}$ alkylene-Z$^1$—C$_{1-15}$ alkyl, —C$_{3-17}$ alkylene-Z$^1$—C$_{1-15}$ alkyl, —X$^2$—C$_{2-16}$ alkylene-Z$^1$—C$_{1-15}$ alkyl, —CH$_2$—X$^2$—C$_{1-15}$ alkylene-Z$^1$—C$_{1-15}$ alkyl, —X$^2$—C(=Y$^4$)C$_{1-15}$ alkylene-Z$^2$, or —X$^2$—C$_{2-16}$ alkylene-Z$^2$;

R$^{3a}$, R$^{3b}$, and R$^{3c}$ are each independently CO$_2$H, —OSO$_3$H, —OP(O)(OH)$_2$, —C$_{1-6}$ alkylene-CO$_2$H, —C$_{1-6}$ alkylene-OSO$_3$H, —C$_{1-6}$ alkylene-OP(O)(OH)$_2$, —OC$_{1-6}$ alkylene-P(O)(OH)$_2$, —C$_{1-6}$ alkylene-P(O)(OH)$_2$, —C$_{1-6}$ haloalkylene-P(O)(OH)$_2$, H, or an ester of the CO$_2$H, —OSO$_3$H, —OP(O)(OH)$_2$, —C$_{1-6}$ alkylene-CO$_2$H, —C$_{1-6}$ alkylene-OSO$_3$H, —C$_{1-6}$ alkylene-OP(O)(OH)$_2$, —OC$_{1-6}$ alkylene-P(O)(OH)$_2$, —C$_{1-6}$ alkylene-P(O)(OH)$_2$, or —C$_{1-6}$haloalkylene-P(O)(OH)$_2$, ;

R$^{3d}$ is CO$_2$H, —SO$_3$H, —P(O)(OH)$_2$, —C$_{1-6}$ alkylene-CO$_2$H, —C$_{1-6}$ alkylene-OSO$_3$H, —C$_{1-6}$ alkylene-OP(O)(OH)$_2$, —OC$_{1-6}$ alkylene-P(O)(OH)$_2$, —C$_{1-6}$ alkylene-P(O)(OH)$_2$, —C$_{1-6}$ haloalkylene-P(O)(OH)$_2$, H, C$_{1-6}$ alkyl, C$_{1-6}$ haloalkyl, C$_{3-8}$ cycloalkyl, or an ester of the CO$_2$H, —OSO$_3$H, —OP(O)(OH)$_2$, —C$_{1-6}$ alkylene-CO$_2$H, —C$_{1-6}$ alkylene-OSO$_3$H, —C$_{1-6}$ alkylene-OP(O)(OH)$_2$, —OC$_{1-6}$ alkylene-P(O)(OH)$_2$, —C$_{1-6}$ alkylene-P(O)(OH)$_2$, or —C$_{1-6}$ haloalkylene-P(O)(OH)$_2$;

R$^{4a}$ is CO$_2$H, CH$_2$OSO$_3$H, CH$_2$CO$_2$H, CH$_2$P(O)(OH)$_2$, CH$_2$OH, H, or an ester of the CO$_2$H, CH$_2$SO$_3$H, CH$_2$CO$_2$H, or CH$_2$P(O)(OH)$_2$;

R$^{4b}$, at each occurrence, is independently CO$_2$H, CH$_2$OSO$_3$H, CH$_2$CO$_2$H, CH$_2$P(O)(OH)$_2$, CH$_2$OH, H, or an ester of the CO$_2$H, CH$_2$SO$_3$H, CH$_2$CO$_2$H, or CH$_2$P(O)(OH)$_2$;

R$^5$ and R$^6$, at each occurrence, are independently H, C$_{1-6}$ alkyl, C$_{1-6}$ haloalkyl, —O—C$_{1-6}$ alkyl, or —C$_{1-6}$ alkylene-OH;

X$^1$ and X$^2$, at each occurrence, are independently O, S, or NH;

X$^3$ is O, S, NH, or CH$_2$;

Y$^1$, Y$^2$, and Y$^3$ are independently O, S, NH, or H$_2$;

Y$^4$, at each occurrence, is independently O, S, or NH;

Z$^1$, at each occurrence, is independently phenylene or 5- to 6-membered heteroarylene, the phenylene and heteroarylene being optionally substituted with 1-4 substituents independently selected from C$_{1-4}$ alkyl, C$_{1-4}$ haloalkyl, —OC$_{1-4}$ alkyl, —OC$_{1-4}$ haloalkyl, cyano, and halogen;

Z$^2$, at each occurrence, is independently phenyl or a 5- to 6-membered heteroaryl, wherein Z$^2$ is optionally substituted with 1-5 substituents independently selected from C$_{1-4}$ alkyl, C$_{1-4}$ haloalkyl, —OC$_{1-4}$ alkyl, —OC$_{1-4}$ haloalkyl, cyano, and halogen; and k and q are each independently an integer from 0-4.

2. The compound of claim 1, or a pharmaceutically acceptable salt thereof, wherein R$^{2a}$, R$^{2b}$, and R$^{2c}$ are each independently —CH(R$^{10}$)(R$^{11}$).

3. The compound of claim 2, or a pharmaceutically acceptable salt thereof, wherein at least one occurrence of R$^{10}$ is C$_{1-21}$ alkyl.

4. The compound of claim 3, or a pharmaceutically acceptable salt thereof, wherein at least one occurrence of R$^{11}$ is —X$^2$—C(=Y$^4$)C$_{1-15}$ alkyl, —X$^2$—C(=Y$^4$)C$_{1-15}$ alkylene-Z$^2$, —X$^2$—C$_{2-16}$ alkylene-Z$^2$, —X$^2$—C$_{2-16}$ alkyl, or —CH$_2$—X$^2$—C$_{1-15}$ alkyl.

5. The compound of claim 4, or a pharmaceutically acceptable salt thereof, wherein Y$^4$ is O.

6. The compound of claim 5, or a pharmaceutically acceptable salt thereof, wherein X$^2$ is O.

7. The compound of claim 6, or a pharmaceutically acceptable salt thereof, wherein Y$^1$, Y$^2$, and Y$^3$ are O.

8. The compound of claim 7, or a pharmaceutically acceptable salt thereof, wherein X$^3$ is O.

9. The compound of claim 8, or a pharmaceutically acceptable salt thereof, wherein R$^{3a}$ is —OP(O)(OH)$_2$, —OSO$_3$H, or —OCH$_2$P(O)(OH)$_2$.

10. The compound of claim 8, or a pharmaceutically acceptable salt thereof, wherein R$^{4a}$ is CH$_2$OH.

11. The compound of claim 8, or a pharmaceutically acceptable salt thereof, wherein R$^1$ is

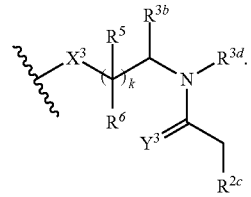

k is 1;
R$^{3b}$ is hydrogen or COOH, or an ester thereof; and
R$^{3d}$, R$^5$, and R$^6$ are each hydrogen.

12. The compound of claim 8, or a pharmaceutically acceptable salt thereof, wherein R$^1$ is

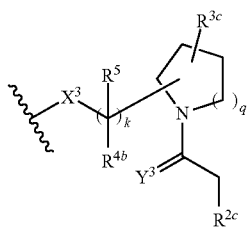

13. The compound of claim 1, selected from the group consisting of
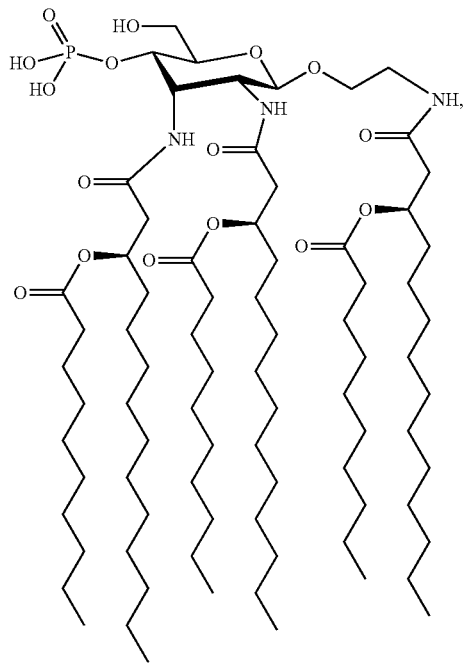
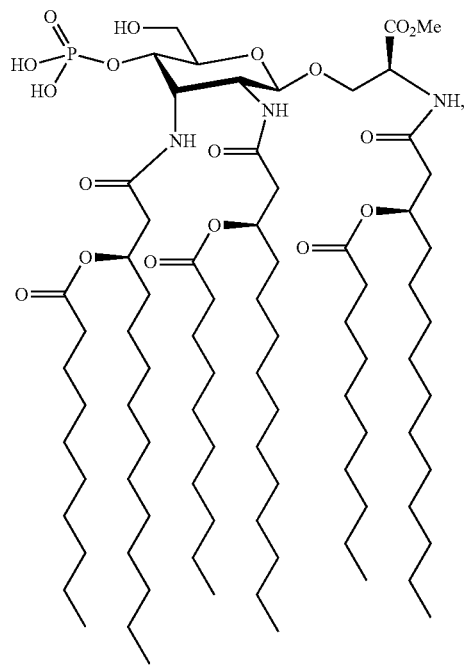
-continued
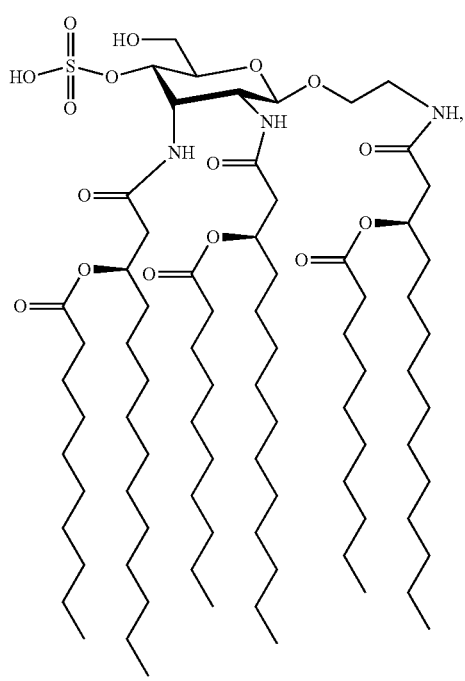
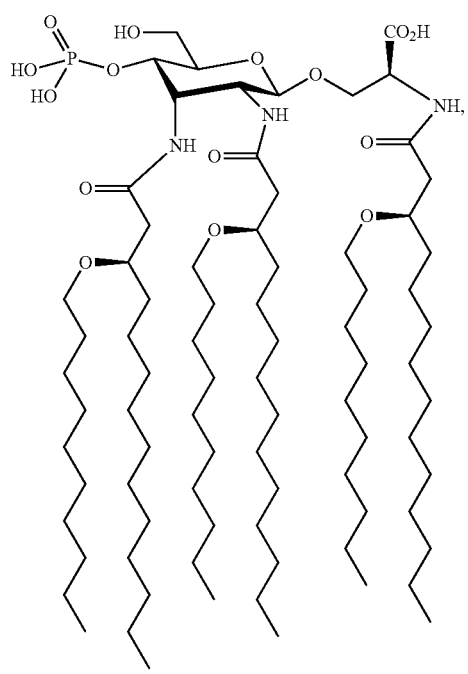

-continued
97
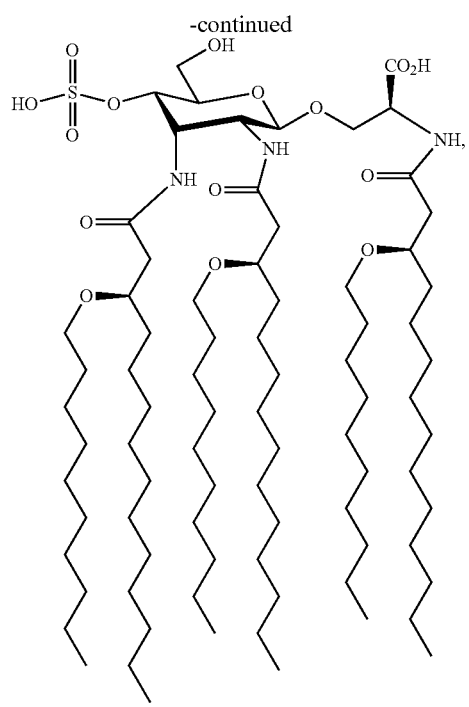
98
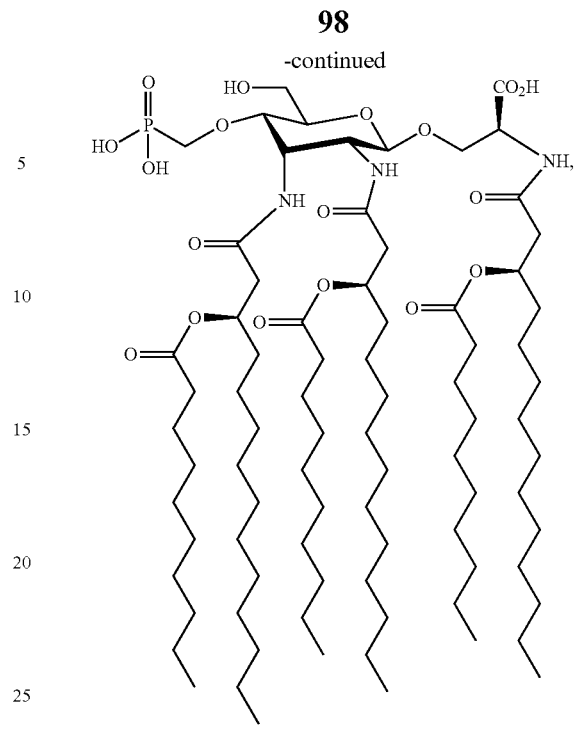
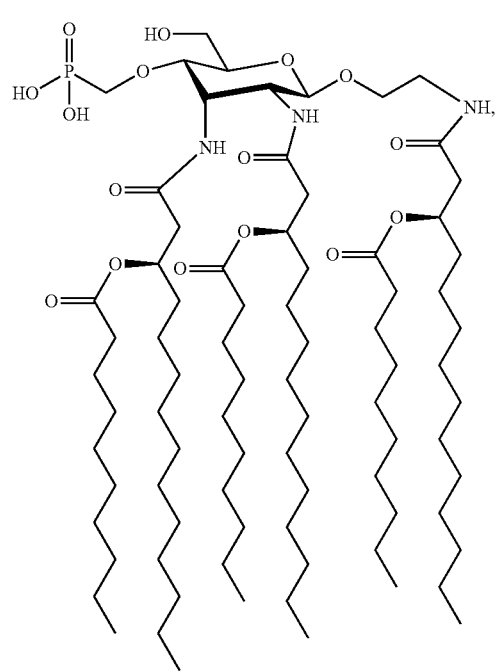
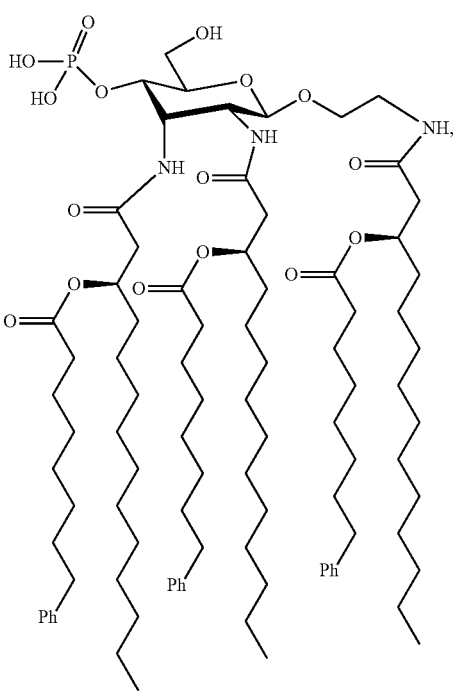

99
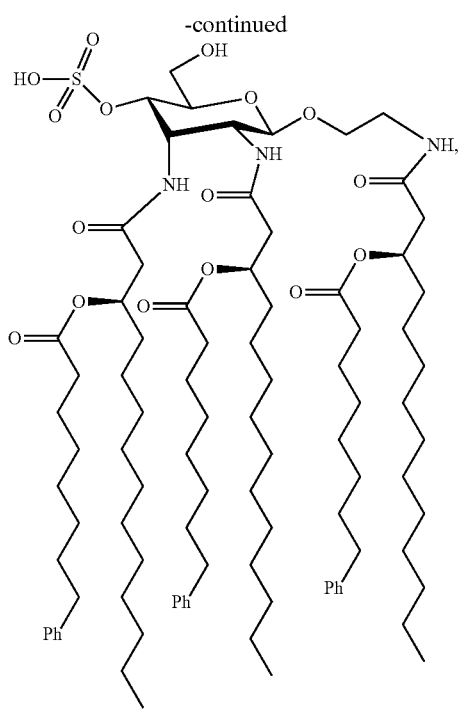
100
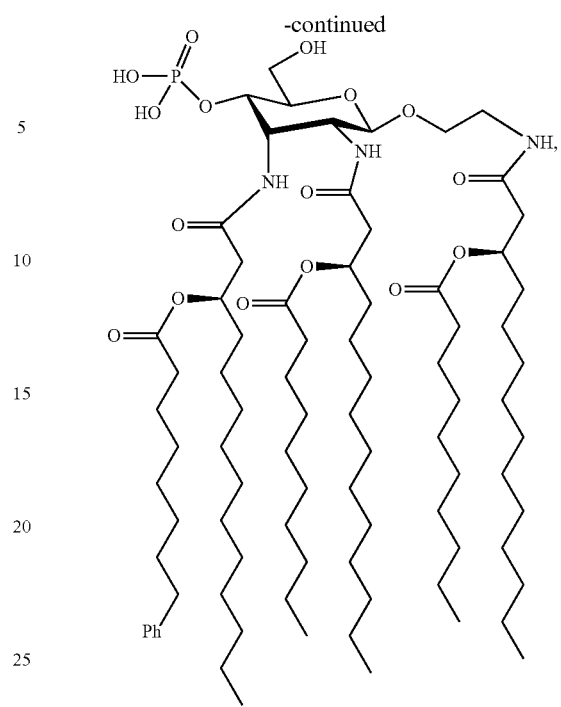
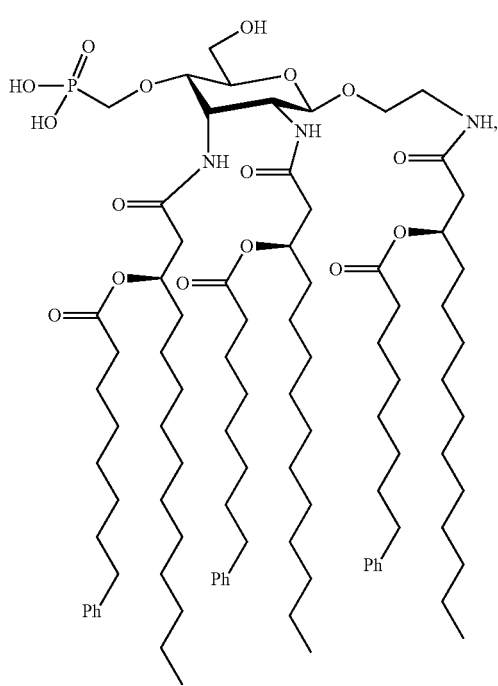
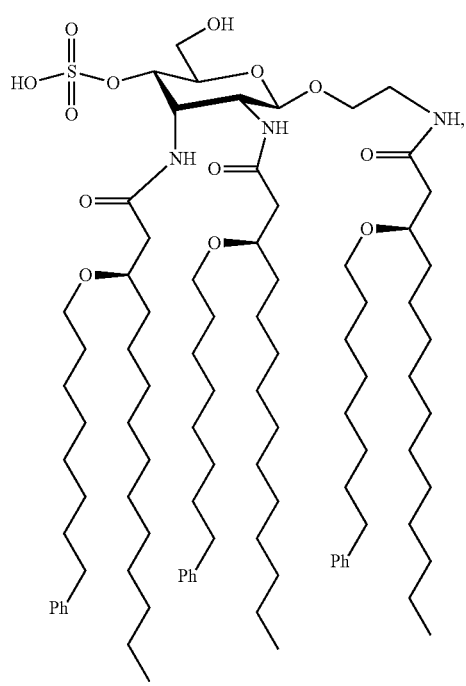

-continued

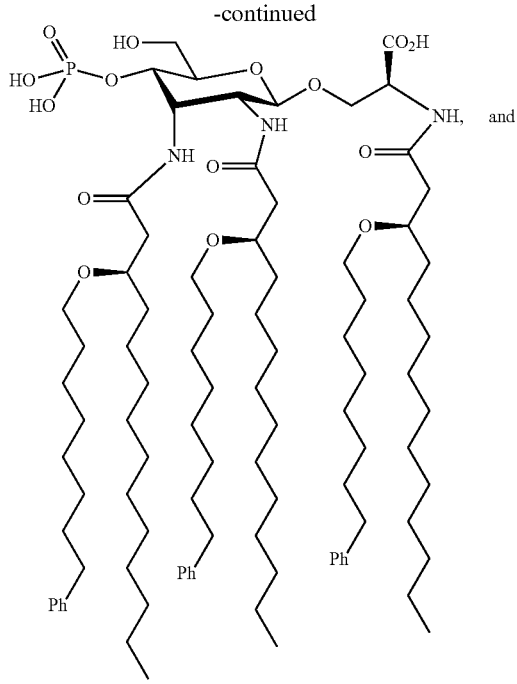

and

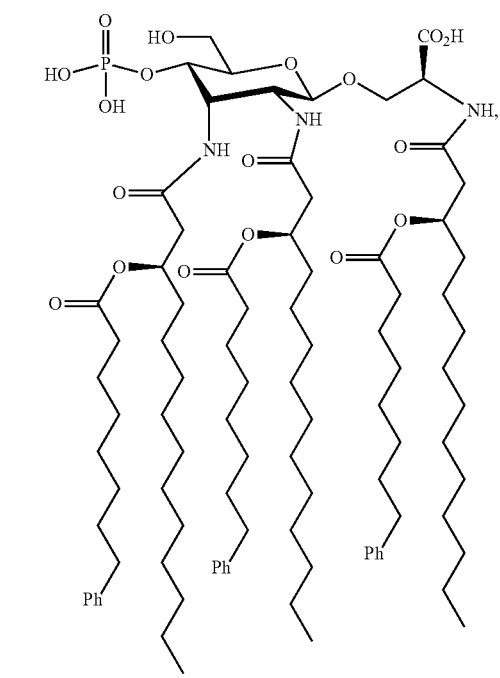

or a pharmaceutically acceptable salt thereof.

14. A pharmaceutical composition comprising the compound of claim 1, or a pharmaceutically acceptable salt thereof, and a pharmaceutically acceptable carrier.

15. A kit comprising:
the compound of claim 1, or a pharmaceutically acceptable salt thereof; and
instructions for use.

16. The compound of claim 11 of formula (I-a), or a pharmaceutically acceptable salt thereof

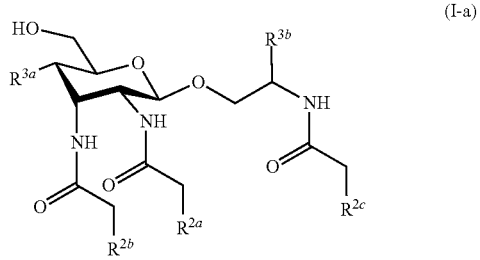

(I-a)

wherein $R^{3a}$ is —OP(O)(OH)$_2$, —OSO$_3$H, or —OCH$_2$P(O)(OH)$_2$.

17. The compound of claim 16, or a pharmaceutically acceptable salt thereof, wherein $R^{10}$, at each occurrence, is independently C$_{8-14}$ alkyl.

18. The compound of claim 17, or a pharmaceutically acceptable salt thereof, wherein $R^{10}$, at each occurrence, is independently C$_{11}$ alkyl.

19. The compound of claim 18, or a pharmaceutically acceptable salt thereof, wherein $R^{10}$, at each occurrence, is independently straight chain C$_{11}$ alkyl.

20. The compound claim 18, or a pharmaceutically acceptable salt thereof, wherein $R^{11}$, at each occurrence, is independently —O—C(=O)C$_9$ alkyl, —O—C$_{10}$ alkyl, O—C(=O)C$_7$ alkylene-Z$^2$, or —O—C$_{8-9}$ alkylene-Z$^2$.

21. The compound of claim 20, or a pharmaceutically acceptable salt thereof, wherein
—CH(R$^{10}$)(R$^{11}$) is

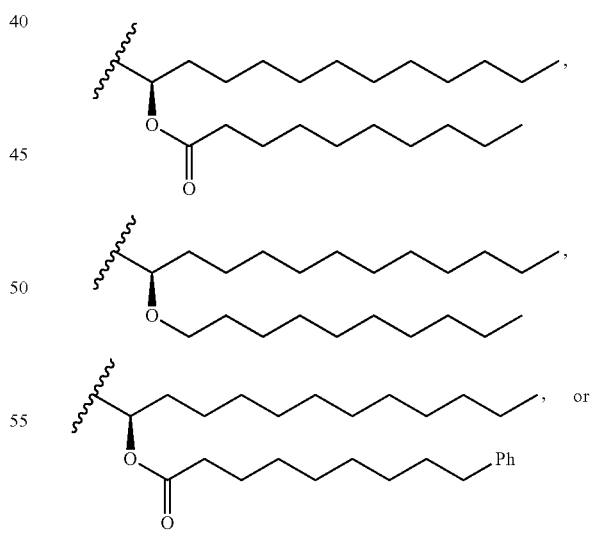

22. The compound or pharmaceutically acceptable salt thereof, of claim 13, wherein
the compound is
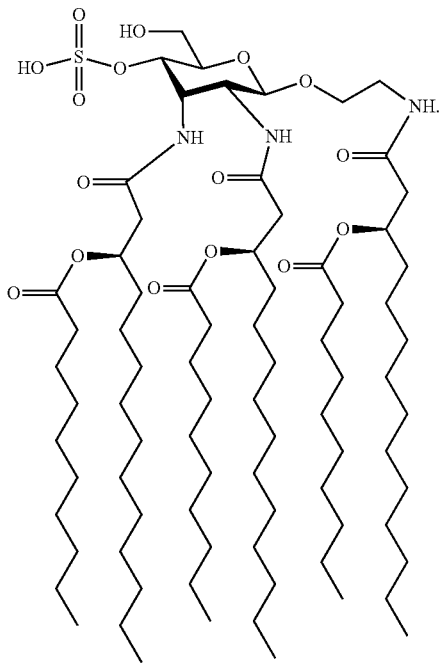
23. The compound, or pharmaceutically acceptable salt thereof, of claim 13, wherein
the compound is
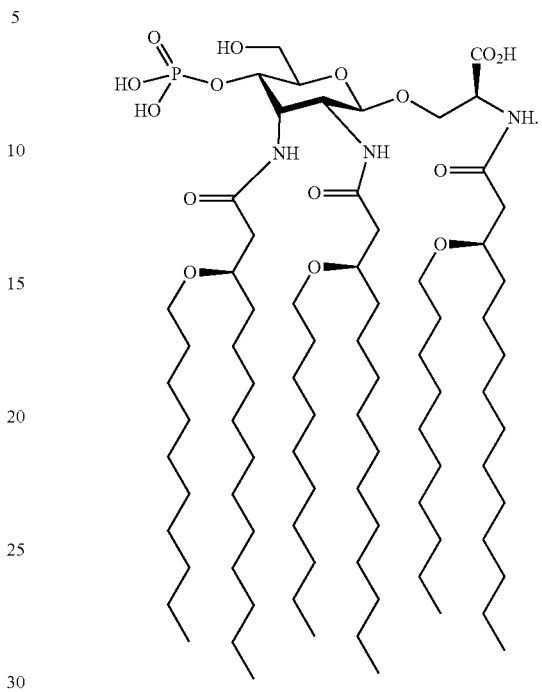
\* \* \* \* \*